(12) United States Patent
Fujii et al.

(10) Patent No.: US 7,854,797 B2
(45) Date of Patent: Dec. 21, 2010

(54) PORPHYRAZINE COLORING MATTER, INK, INK SET, AND COLORED PRODUCT

(75) Inventors: Takafumi Fujii, Tokyo (JP); Takashi Yoneda, Tokyo (JP); Yasuo Kuroda, Tokyo (JP); Yoshiaki Kawaida, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/450,127

(22) PCT Filed: Mar. 13, 2008

(86) PCT No.: PCT/JP2008/054584

§ 371 (c)(1),
(2), (4) Date: Sep. 11, 2009

(87) PCT Pub. No.: WO2008/111635

PCT Pub. Date: Sep. 18, 2008

(65) Prior Publication Data

US 2010/0112218 A1 May 6, 2010

(30) Foreign Application Priority Data

Mar. 14, 2007 (JP) .............................. 2007-064591

(51) Int. Cl.
*C09D 11/02* (2006.01)
*C07D 487/22* (2006.01)
*B41J 2/01* (2006.01)

(52) U.S. Cl. .................. 106/31.47; 540/124; 540/125; 540/126; 347/100

(58) Field of Classification Search .............. 106/31.47; 540/124, 125, 126; 347/100; 428/195.1
See application file for complete search history.

(56) References Cited

U.S. PATENT DOCUMENTS

| | | | |
|---|---|---|---|
| 6,238,827 B1 | 5/2001 | Nakazawa et al. ............. 430/7 |
| 7,097,701 B2 | 8/2006 | Tateishi et al. ........... 106/31.47 |
| 7,132,012 B2 | 11/2006 | Tateishi et al. ........... 106/31.47 |
| 7,270,701 B2 | 9/2007 | Jinnou et al. ............. 106/31.47 |
| 7,282,090 B2 | 10/2007 | Osumi et al. ............. 106/31.47 |
| 7,419,537 B2 | 9/2008 | Fujii et al. ............... 106/31.47 |
| 7,566,362 B2 * | 7/2009 | Mori et al. ............... 106/31.47 |
| 7,585,361 B2 * | 9/2009 | Yoneda et al. ........... 106/31.47 |
| 7,591,888 B2 * | 9/2009 | Fujii et al. ............... 106/31.47 |
| 2002/0128249 A1 | 9/2002 | Cook ........................ 540/124 |
| 2006/0201382 A1 | 9/2006 | Ozawa et al. ............ 106/31.47 |
| 2006/0268086 A1 | 11/2006 | Kawakami et al. .......... 347/100 |
| 2007/0006772 A1 * | 1/2007 | Fujii et al. ............... 106/31.49 |
| 2008/0274286 A1 | 11/2008 | Yamashita et al. ........ 106/31.47 |
| 2009/0029120 A1 | 1/2009 | Fujii et al. ............... 428/195.1 |
| 2009/0047430 A1 | 2/2009 | Mori et al. ................. 347/100 |
| 2009/0151599 A1 | 6/2009 | Fujii et al. ............... 106/31.47 |
| 2009/0202798 A1 * | 8/2009 | Patel ........................ 540/126 |
| 2010/0126377 A1 * | 5/2010 | Yoneda et al. ........... 106/31.49 |

FOREIGN PATENT DOCUMENTS

| | | |
|---|---|---|
| EP | 1 741 756 | 1/2007 |
| JP | 2004-75986 | 3/2004 |
| JP | 2004-323605 | 11/2004 |
| JP | 2006-45535 | 2/2006 |
| JP | 2007-23251 | 2/2007 |
| JP | 2007-277416 | 10/2007 |
| JP | 2008-13706 | 1/2008 |
| WO | 2005/021658 | 3/2005 |
| WO | 2007/091631 | 8/2007 |
| WO | 2007/116933 | 10/2007 |

OTHER PUBLICATIONS

The International Search Report dated Apr. 22, 2008.
The International Search Report dated May 15, 2007 in co-pending US Patent 7,591,888.
NOA dated Jul. 10, 2009 in U.S. Appl. No. 12/223,559 (USPatent. 7,591,888).
The International Search Report dated Jul. 10, 2007 in co-pending US Patent 7,585,361.
NOA dated Jun. 26, 2009 in U.S. Appl. No. 12/226,043 (USPatent. 7,585,361).

* cited by examiner

*Primary Examiner*—Helene Klemanski
(74) *Attorney, Agent, or Firm*—Nields, Lemack & Frame, LLC

(57) ABSTRACT

The present invention relates to a porphyrazine coloring matter represented by the following formula (1) or a salt thereof;

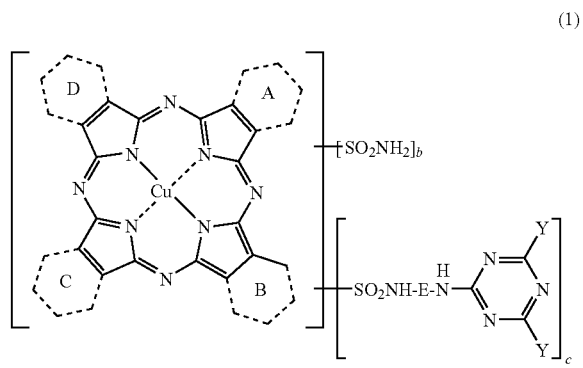

(1)

wherein, each of the rings A to D independently represents a benzene ring or a 6-membered nitrogen-containing heteroaromatic ring, at least one or more thereof is a benzene ring, at least one of the rest is a nitrogen-containing heteroaromatic ring, E represents alkylene, X is an anilino group having a substituent and the like, Y represents an amino group; a hydroxy group; a mono- or di-alkylamino group or a nitrogen-containing heterocyclic group which may have a substituent, excepting for the combination in which Y is an amino group or a hydroxy group and X is a substituted anilino group, b is 0 to 2.9, c is 0.1 to 3, and the sum of b and c is 1 to 3. According to the present invention, a porphyrazine coloring matter suitable for inkjet recording which has a good hue as a cyan ink, is excellent in light fastness, ozone fastness and moisture fastness, and causes no bronze phenomenon can be provided.

25 Claims, No Drawings

PORPHYRAZINE COLORING MATTER, INK, INK SET, AND COLORED PRODUCT

TECHNICAL FIELD

The present invention relates to a novel porphyrazine coloring matter, an ink, an ink set, and an inkjet recording method using ink thereof or ink set thereof, and a colored product.

BACKGROUND ART

Recently, as an image recording material, recording materials used for the inkjet method, image recording materials for the thermal transfer, recording materials used for the electrophotographic method, halogenated silver photosensitive materials for transcription, printing inks, inks for recording pens, and the like are extensively used. Many of the recent recorded images are color images and a material for forming said color images is the mainstream. In addition, color filters are used in electronic parts such as LCD (liquid crystal display) or PDP (plasma display panel) for color and CCD (charge coupled device), where materials for forming color images are also used. In them, full color images are reproduced or recorded by so-called additive or subtractive color process, and coloring matters (dyes or pigments) of 3 primary colors are used as materials thereof. However, it is the case that there is no coloring matter having absorption characteristics which can provide preferable color reproduction areas and having sufficient fastnesses in various use conditions, so improvement of coloring matters is strongly required.

The inkjet recording method has been rapidly prevailing and further developing due to its low material cost, possibility of rapid recording, less noise in recording and also easiness of color recording. The inkjet recording method includes the continuous method of continuously flying ink droplets and the on-demand method of flying ink droplets responding to an image information signal, and the discharging method includes a method of discharging ink droplets by applying pressure with piezoelectric elements, a method of discharging ink droplets by generating bubbles in ink by heat, a method by using ultrasonic waves, a method of sucking and discharging ink droplets by electrostatic force, or the like. In addition, examples of the ink suitable for inkjet recording include water-based inks, oil-based inks, solid (melting-type) inks and the like.

The requirements for the coloring matter used for inks suitable for such inkjet recording include good solubility or dispersibility in solvents, ability of high density recording, good hue, good fastness to light, heat and active gases (oxidizing gas such as NOx and ozone, SOx and the like) in the environment, excellent durability against water and chemicals, good fixation to record-receiving materials in order not to bleed, excellent storage stability as an ink, no toxicity, and also inexpensive availability, and the like. In particular, strongly required is a cyan coloring matter which has a good cyan hue, is excellent in light fastness (durability against light), ozone fastness (durability against ozone gas) and moisture fastness (durability under high humidity), and causes no bronze phenomenon (also referred to as bronzing phenomenon). Bronze phenomenon means glare phenomenon that glossy paper has a metallic luster because coloring matter is aggregated on its surface due to association and aggregation of coloring matter, malabsorption of ink to the media, or the like. This phenomenon leads to inferiority in all respects such as glossiness, print quality and print density.

As a water-soluble cyan coloring matter used for inks suitable for inkjet recording, a phthalocyanine-based coloring matter and a triphenylmethane-based coloring matter are typical. The typical phthalocyanine-based coloring matter reported and used in the widest range includes phthalocyanine derivatives classified into the following A to H:

A: known phthalocyanine-based coloring matter such as Direct Blue 86, Direct Blue 87, Direct Blue 199, Acid Blue 249, Reactive Blue 71 or the like;

B: phthalocyanine-based coloring matter described in Patent Literatures 1 to 3 and the like (for example, a mixture of $Cu-Pc-(SO_3Na)_m(SO_2NH_2)n:m+n=1$ to 4);

C: phthalocyanine-based coloring matter described in Patent Literature 4 and the like (for example, $Cu-Pc-(CO_2H)m(CONR^1R^2)n:m+n=$a number of 0 to 4);

D: phthalocyanine-based coloring matter described in Patent Literature 5 and the like (for example, $Cu-Pc-(SO_3H)m(SO_2NR^1R^2)n:m+n=$a number of 0 to 4, and $m \neq 0$);

E: phthalocyanine-based coloring matter described in Patent Literature 6 and the like (for example, $Cu-Pc-(SO_3H)l(SO_2NH_2)m(SO_2NR^1R^2)n:l+m+n=$a number of 0 to 4);

F: phthalocyanine-based coloring matter described in Patent Literature 7 and the like (for example, $Cu-Pc-(SO_2NR^1R^2)n:n=$a number of 1 to 5);

G: phthalocyanine-based coloring matter described in Patent Literatures 8, 9 and 12 and the like (phthalocyanine compound in which the substitution position of the substituent is controlled and phthalocyanine-based coloring matter in which a substituent is introduced at the beta-position);

H: benzo pyridoporphyrazine-based coloring matter having a pyridine ring and a benzene ring, described in Patent Literatures 10, 13 and 14, and the like.

The phthalocyanine-based coloring matter typified by Direct Blue 86 or Direct Blue 199 which are usually used widely at present has a characteristic of being excellent in light fastness compared with magenta coloring matters and yellow coloring matters which are generally known. The phthalocyanine-based coloring matter has a greenish hue under acidic conditions, whereby it is not very preferable as a cyan ink. Therefore, it is preferable that these coloring matters are used under neutral to alkaline conditions when used as a cyan ink. However, although the ink to be used is neutral to alkaline, the hue of a printed matter may be greatly changed when the record-receiving material to be used is an acidic paper.

In addition, when the phthalocyanine-based coloring matter is used as a cyan ink, the hue of a printed matter is discolored greenish and also color fading occurs due to oxidizing gases such as nitrogen oxide gas and ozone which are often concerned nowadays as an environmental problem, whereby the print density is concurrently reduced.

On the other hand, the triphenylmethane-based coloring matter has a good hue but is very inferior in light fastness, ozone fastness and moisture fastness.

From here on, when the application field of inkjet recording is widespread and inkjet recording is widely used in articles on exhibition for advertisement and the like, the coloring matter and the ink used there will be more and more strongly required to have a good hue and to be inexpensive, and further, in particular to have a good hue and to be excellent in light fastness, fastness to active gases in the environment (oxidizing gases such as NOx and ozone and in addition SOx, and the like) and moisture fastness because they will be more often exposed to light and active gases in the environment. However, it is difficult to develop a cyan coloring matter (for example, phthalocyanine-based coloring matter) and a cyan ink which satisfy these requirements at a high level. In the past, although phthalocyanine-based coloring matters to which fastness to active gases is imparted are disclosed in Patent Literatures 3, 8 to 12, and 14, and the like, a cyan coloring matter and a cyan ink have not yet been obtained which satisfy all the qualities such as hue, light fastness, ozone fastness, moisture fastness and no bronze phenomenon, and further which can be produced inexpensively. Therefore, the requirements of the market have not been sufficiently satisfied.

Patent Literature 1: JP S62-190273 A

Patent Literature 2: JP H7-138511 A

Patent Literature 3: JP 2002-105349 A

Patent Literature 4: JP H5-171085 A

Patent Literature 5: JP H10-140063 A

Patent Literature 6: JP H11-515048 A

Patent Literature 7: JP S59-22967 A

Patent Literature 8: JP 2000-303009 A

Patent Literature 9: JP 2002-249677 A

Patent Literature 10: JP 2003-34758 A

Patent Literature 11: JP 2002-80762 A

Patent Literature 12: WO 2004087815 A

Patent Literature 13: WO 2002034844 A

Patent Literature 14: JP 2004-75986 A

DISCLOSURE OF THE INVENTION

Problems to Be Solved by the Invention

It is a subject of the present invention to solve the above problems to provide a novel coloring matter which has a good hue as a cyan ink, is excellent light fastness, ozone fastness and moisture fastness and causes no bronze phenomenon, and further to provide an ink suitable for inkjet and an inkjet recording method by using said coloring matter.

Means of Solving the Problems

The present inventors have closely studied on a coloring matter having a good hue and high light and ozone fastnesses and causing no bronze phenomenon, and found that a particular porphyrazine coloring matter represented by the following formula (1) can solve the above problems, and thus the present invention has been completed. That is, the present invention relates to:

(1) A porphyrazine coloring matter represented by the following formula (1) or a salt thereof:

Formula (1)

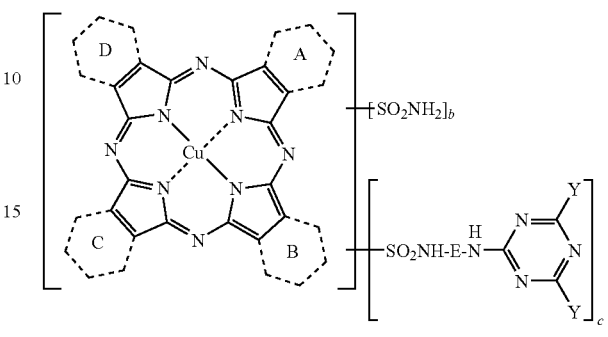

(wherein:

each of the rings A to D independently represents a benzene ring or a 6-membered nitrogen-containing heteroaromatic ring, at least one or more thereof is a benzene ring and at least one of the rest is a nitrogen-containing heteroaromatic ring, E represents alkylene, X is an anilino group or a naphthylamino group, having at least one sulfo, carboxy or phosphono group, as a substituent, said anilino group or said naphthylamino group may be further substituted by one or more kinds of substituents selected from the group consisting of a sulfo group, a carboxy group, a phosphono group, a sulfamoyl group, a carbamoyl group, a hydroxy group, an alkoxy group, an amino group, a mono- or di-alkylamino group, a mono- or di-arylamino group, an acetylamino group, an ureide group, an alkyl group, a nitro group, a cyano group, a halogen atom, an alkylsulfonyl group and an alkylthio group, Y represents an amino group; a hydroxy group; a mono- or di-alkylamino group or a nitrogen-containing heterocyclic group, which may have one or more kinds of substituents selected from the group consisting of a sulfo group, a carboxy group, a phosphono group, a sulfamoyl group, a carbamoyl group, a hydroxy group, an alkoxy group, an amino group, a mono- or di-alkylamino group, a mono- or di-arylamino group, an acetylamino group, an ureide group, an alkyl group, a nitro group, a cyano group, a halogen atom, an alkylsulfonyl group and an alkylthio group; however, excepting for the combination in which Y is an amino group or a hydroxy group and X is a substituted anilino group, b is from 0 to 2.9, c is from 0.1 to 3, and the sum of b and c is from 1 to 3), (2) The porphyrazine coloring matter or a salt thereof according to the above (1), wherein the 6-membered nitrogen-containing heteroaromatic ring represented by the rings A to D is a pyridine ring or a pyrazine ring, (3) The porphyrazine coloring matter or a salt thereof according to the above (1) or the above (2), which is obtained by reacting a porphyrazine compound represented by the following formula (3) with an organic amine represented by the following formula (4) in the presence of ammonia:

Formula (3)

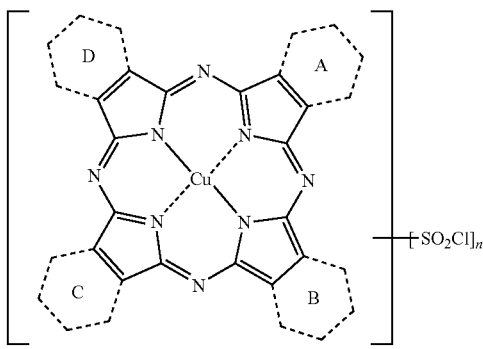

(wherein, the rings A to D have the same meanings as those described in the above (1), and n is from 1 to 3), Formula (4)

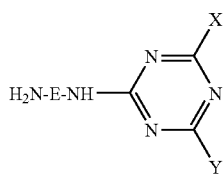

(wherein, E, X and Y have the same meanings as those described in the above (1)), (4) The porphyrazine coloring matter or a salt thereof according to the above (2), wherein, among the rings A to D, 1 to 3 rings is a pyridine ring or a pyrazine ring, E represents C2 to C4 alkylene, X is an anilino group or a naphthylamino group, having at least one sulfo or carboxy group, as a substituent; or a phosphono-substituted anilino group, said substituted anilino and naphthylamino groups may further have 0 to 3 of one or more kinds of substituents selected from the group consisting of a sulfo group, a carboxy group, a phosphono group, a hydroxy group, an alkoxy group, an ureide group, an acetylamino group, a nitro group and a chlorine atom, Y is an amino group; a hydroxy group; a mono- or di-alkylamino group or a nitrogen-containing heteroaromatic ring group, which may be substituted by a hydroxy group, a sulfo group, a carboxy group or a phosphono group; however, excepting for the combination in which Y is an amino group or a hydroxy group and X is a substituted anilino group, b is from 0 to 2.9, c is from 0.1 to 3, and the sum of b and c is from 1 to 3, (5) The porphyrazine coloring matter or a salt thereof according to the above (4), wherein, E represents ethylene or propylene, X is a sulfo-substituted anilino group; a carboxy-substituted anilino group; or a sulfo-substituted naphthylamino group, Y is an amino group; a hydroxy group; or a mono- or di-alkylamino group or a nitrogen-containing heteroaromatic ring group, which may be substituted by a hydroxy group, a sulfo group, a carboxy group; however, excepting for the combination in which Y is an amino group or a hydroxy group and X is a substituted anilino group, b is from 0 to 2.9, c is from 0.1 to 3, and the sum of b and c is from 1 to 3), (6) The porphyrazine coloring matter or a salt thereof according to the above (1), wherein, the ring A is a pyridine ring fused at the 2-position and the 3-position or at the 3-position and the 4-position, or a pyrazine ring fused at the 2-position and the 3-position, the ring B is a pyridine ring fused at the 2-position and the 3-position or at the 3-position and the 4-position, or a pyrazine ring fused at the 2-position and the 3-position, or a benzene ring, the ring C is a pyridine ring fused at the 2-position and the 3-position or at the 3-position and the 4-position, or a pyrazine ring fused at the 2-position and the 3-position, or a benzene ring, the ring D is a benzene ring, E is C2 to C4 alkylene, X is an anilino group or a naphthylamino group, having 1 to 3 substituents selected from the group consisting of a sulfo group, a carboxy group, a methoxy group, a nitro group, a chlorine atom, a hydroxy group, Y is an amino group; a hydroxy group; a mono- or di-C1 to C4 alkylamino group or a 5 to 7-membered nitrogen-containing heterocyclic group, which may be substituted by a hydroxy group, a sulfo group or a carboxy group; however, excepting for the combination in which Y is an amino group or a hydroxy group and X is a substituted anilino group, b is from 0 to 2.9 and c is from 0.1 to 3, (7) The porphyrazine coloring matter or a salt thereof according to the above (1) or the above (2), which is represented by the following formula (2):

Formula (2)

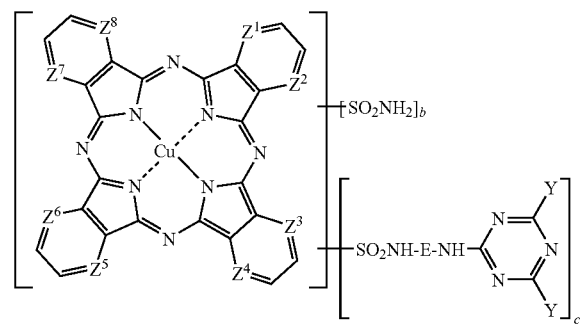

(wherein, each of $Z^1$ to $Z^8$ independently represents a nitrogen atom or a carbon atom, at least one among the combinations of $Z^1$ and $Z^2$, $Z^3$ and $Z^4$, $Z^5$ and $Z^6$, and $Z^7$ and $Z^8$ is a combination of carbon atoms, and E, X, Y, b and c have the same meanings as those described in (1)), (8) The porphyrazine coloring matter or a salt thereof according to the above (7), which is obtained by reacting a porphyrazine coloring matter represented by the following formula (5) with an organic amine represented by the formula (4) described in the above (3) in the presence of ammonia:

Formula (5)

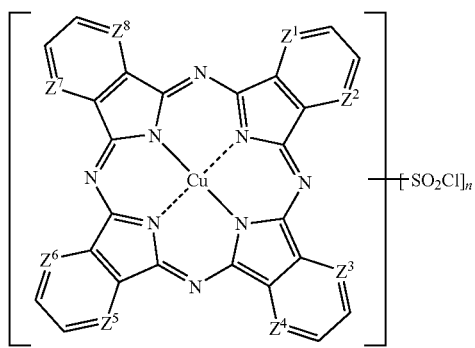

(5)

(wherein, $Z^1$ to $Z^8$ have the same meanings as those described in the above (7) and n is from 1 to 3), (9) The porphyrazine coloring matter or a salt thereof according to the above (1), which is a mixture of a porphyrazine coloring matter in which one of the rings A to D is a nitrogen-containing heteroaromatic ring and the other three are benzene rings and a porphyrazine coloring matter in which two of the rings A to D are nitrogen-containing heteroaromatic rings and the other two are benzene rings,

(10) The porphyrazine coloring matter or a salt thereof according to the above (9) wherein the nitrogen-containing heteroaromatic ring is a pyridine ring,

(11) A mixture of coloring matters containing the porphyrazine coloring matter or a salt thereof according to any one of the above (1) to the above (10),

(12) A mixture of coloring matter of the porphyrazine coloring matter or a salt thereof according to any one of the above (1) to the above (10) and a phthalocyanine coloring matter,

(13) An ink characterized by containing at least one kind of the porphyrazine coloring matter or a salt thereof according to any one of the above (1) to the above (10) as a coloring matter component,

(14) The ink according to the above (13), containing an organic solvent together with the porphyrazine coloring matter,

(15) The ink according to the above (13) or the above (14), which is for inkjet recording,

(16) An inkjet recording method characterized by discharging ink droplets of the ink according to any one of the above (13) to the above (15) responding to a recording signal to carry out recording on a record-receiving material,

(17) The inkjet recording method according to the above (16), wherein the record-receiving material is a communication sheet,

(18) The inkjet recording method according to the above (17), wherein the communication sheet is a sheet subjected to surface treatment and has an ink image receiving layer containing white inorganic pigment particles on a support thereof,

(19) A container containing the ink according to any one of the above (13) to the above (15),

(20) An inkjet printer having the container according to the above (19),

(21) A colored product colored with the ink according to any one of the above (13) to the above (15),

(22) The porphyrazine coloring matter or a salt thereof according to the above (1), wherein, among the rings A to D, 1 to 2 rings is a pyridine ring or a pyrazine ring and the rest are benzene rings, as an average value, E represents C2 to C4 alkylene, and (i) X is a mono- or disulfo-substituted anilino group; a dicarboxy-substituted anilino group; or a mono- or disulfo-substituted naphthylamino group, Y is a mono- or di(C1 to C4 alkyl)amino group having a group selected from the group consisting of a hydroxy group, a sulfo group, a carboxy group and a C1 to C4 alkoxy group (which may be substituted with a hydroxy group) as a substituent; or a 5 to 7-membered nitrogen-containing heterocyclic group which may have a group selected from the group consisting of methyl, ethyl, sulfo, and carboxy group and hydroxy group as a substituent, or (ii) X is a sulfo-substituted naphthylamino group and Y is an amino group,

(23) The porphyrazine coloring matter or a salt thereof according to the above (1), wherein Y is 2-sulfoethylamino, 2-carboxyethylamino, carboxymethylamino, 2-hydroxyethylamino, 2-ethoxy-2-ethylamino, 1-hydroxy-butylamino, 5-carboxy-pentylamino, 2-methoxy-ethylamino, 2-ethoxyethylamino, (2-hydroxy)ethoxyethylamino, di(2-hydroxyethyl)amino or di(2-carboxyethyl)amino,

(24) The porphyrazine coloring matter or a salt thereof according to the above (1), wherein Y is 2-sulfoethylamino, bis(2-carboxyethyl)amino, 2-hydroxyethylamino, 2-hydroxyethoxyethylamino, morpholinyl, piperidinyl, pyrrolidinyl, 2-carboxypyrrolidinyl, 4-ethylpiperazinyl, 2-ethylpiperidinyl or 3-methylpyrrolidinyl.

EFFECT OF THE INVENTION

The ink using the compound of the present invention is an ink having a good hue as a cyan ink and being excellent in light fastness, ozone fastness and moisture fastness. In addition, it has no crystal precipitation, no change in physical properties and no color change after storage for a long period of time, and thus its storage stability is good. Further, by using a magenta ink and a yellow ink other than it, it can exhibit a color tone in a wide visible region. Therefore, the cyan ink using the porphyrazine coloring matter of the present invention is extremely useful as an ink for inkjet recording.

BEST MODE FOR CARRYING OUT THE INVENTION

The present invention will be explained more specifically. The ink suitable for inkjet recording of the present invention is characterized by containing the porphyrazine coloring matter of the above formula (1). That is, it has been found that the porphyrazine coloring matter using porphyrazine in which 1 to 3 from 4 benzo(benzene) rings of tetrabenzoporphyrazine (usually, referred to as phthalocyanine) is replaced by a 6-membered nitrogen-containing heteroaromatic ring as the mother nucleus of the coloring matter and introducing an unsubstituted sulfamoyl group and a particular substituted sulfamoyl group is very suitable for an ink for inkjet, and that recorded matters with an ink using said coloring matter have an extremely excellent fastness to ozone gas and hardly cause bronze phenomenon.

In the above formula (1), the nitrogen-containing heteroaromatic ring for the rings A, B, C and/or D includes, for example, a 6-membered nitrogen-containing heteroaromatic ring containing 1 to 2 nitrogen atoms, such as a pyridine ring, a pyrazine ring, a pyrimidine ring and/or a pyridazine ring. Among them, a pyridine ring or a pyrazine ring is preferable and a pyridine ring is the most preferable. 1 to 3 of A, B, C and D is a nitrogen-containing heteroaromatic ring and the rest are benzene rings. There is a tendency that as the number of said nitrogen-containing heteroaromatic ring is increased, ozone fastness is improved but bronzing is apt to occur, whereby it is advisable to select a well balanced ratio by appropriately controlling the number of said nitrogen-containing heteroaromatic ring in view of ozone fastness and bronzing. The number of said nitrogen-containing heteroaromatic ring depends on the kind of the heterocyclic ring and thus it is not appropriate to limit without variation, but usually the number is preferably in the range of 1 to 2 rings, more preferably in the range of 1.1 to 1.75 rings and further preferably in the range of 1.1 to 1.5 rings, as an average value. The rest are benzene rings. When the number of the nitrogen-containing heteroaromatic ring is more than 1 and less than 2, the number is the average number of the heterocycle in a mixture of a compound having one said nitrogen-containing heteroaromatic rings with a compound having two said nitrogen-containing heteroaromatic rings.

When the number of the heterocycle is 2, it is considered that both a compound in which the two heterocycle are next to each other (for example, A and B) and a compound in which the two heterocycle are opposite each other in a diagonal position (for example, A and C) are produced. When the compound is described by using its structural formula in the explanation of the production method or in the examples, a structural formula of the compound in which two of A and C are heterocycle and B and D are benzene rings is described for convenience, unless otherwise noted, which stands for both the compounds produced as the above, because it is complicated and confusing to describe all the structures and also it is unnecessary to bother to distinguish them in the present invention.

b is from 0 to 2.9, c is from 0.1 to 3, and the sum of b and c is from 1 to 3. There is a tendency that as b is larger, ozone fastness is improved but bronzing is apt to occur, whereby it is advisable to select a well balanced ratio by appropriately controlling the numbers of b and c in view of ozone fastness and bronzing. Usually, it is preferable that b is in the range of 0.5 to 2.5, c is in the range of 0.1 to 1.5 and b+c is in the range of 1.5 to 3, and it is more preferable that b is in the range of 1 to 2.5, c is in the range of 0.5 to 1 and b+c is in the range of 2.0 to 3.0.

The alkylene in E includes, for example, alkylene having 2 to 12 carbon atoms, more preferably alkylene having 2 to 6 carbon atoms and further preferably alkylene having 2 to 4 carbon atoms. Specific examples thereof include ethylene, propylene, butylene, pentylene, hexylene, cyclopropylene-diyl, 1,2- or 1,3-cyclopentylenediyl, and 1,2-, 1,3- or 1,4-cyclohexylene. Preferable is ethylene, propylene or butylene. More preferable is ethylene.

X is an anilino group or a naphthylamino group, having at least one group selected from the group consisting of a sulfo group, a carboxy group and a phosphono group, as a substituent.

Said anilino group or said naphthylamino group may further have a substituent described below. The number of said substituent which they may further have is usually 0 to 4 and preferably 0 to 3.

Examples of the substituent which they may further have include a group selected from the group consisting of sulfo, carboxy, phosphono group, sulfamoyl, carbamoyl, hydroxy, alkoxy, amino, mono- or di-alkylamino, mono- or di-arylamino, acetylamino, ureide, alkyl, nitro, cyano and a halogen atom. In addition, further as said substituent, allyloxy, a heterocycle residual group or the like may be included.

Among the above substituents, preferable examples of the substituent include sulfo, carboxy, and a hydroxy group. In addition, when X is a naphthylamino group, sulfo and a hydroxy group are preferable among the above substituents.

Examples of a preferable group as X can include mono- or di-sulfo-substituted anilino or dicarboxy-substituted anilino, mono- or di-sulfo-substituted naphthylamino, and more preferably mono- or di-sulfo-substituted anilino or disulfo-substituted naphthylamino.

Specific examples thereof include 2,5-disulfoanilino, 2-sulfoanilino, 3-sulfoanilino, 4-sulfoanilino, 2-carboxyanilino, 4-carboxyanilino, 4-ethoxy-2-sulfoanilino, 2-methyl-5-sulfoanilino, 2-methoxy-4-nitro-5-sulfoanilino, 2-chloro-5-sulfoanilino, 3-carboxy-4-hydroxyanilino, 3-carboxy-4-hydroxy-5-sulfoanilino, 2-hydroxy-5-nitro-3-sulfoanilino, 4-acetylamino-2-sulfoanilino, 4-anilino-3-sulfoanilino, 3,5-dichloro-4-sulfoanilino, 3-phosphonoanilino, 3,5-dicarboxyanilino, 2-carboxy-4-sulfoanilino, 2-carboxy-5-sulfoanilino, 5,7-disulfonaphthalen-2-ylamino, 6,8-disulfonaphthalen-2-ylamino, 3,6-disulfonaphthalen-1-ylamino, 3,6,8-trisulfonaphthalen-1-ylamino, 8-hydroxy-3,6-disulfonaphthalen-1-ylamino, 4,8-disulfonaphthalen-2-ylamino, 3,6,8-trisulfonaphthalen-2-ylamino, 4,6,8-trisulfonaphthalen-2-ylamino, 8-chloro-3,6-disulfonaphthalen-1-ylamino, 8-hydroxy-6-sulfonaphthalen-2-ylamino, 5-hydroxy-7-sulfonaphthalen-2-ylamino and the like. Among them, preferable examples of the group can include 2,5-disulfoanilino, 2-sulfoanilino, 3-sulfoanilino, 4-sulfoanilino, 2-carboxyanilino, 4-carboxyanilino, 3,5-dicarboxyanilino, 5,7-disulfonaphthalen-2-ylamino, 6,8-disulfonaphthalen-2-ylamino, 3,6-disulfonaphthalen-1-ylamino and the like.

Y represents an amino group; a hydroxy group; a mono- or di-alkylamino group or a nitrogen-containing heterocyclic group, which may have a substituent. More preferable is a mono- or di-alkylamino group or a nitrogen-containing heterocyclic group, which may have a substituent.

When Y is a mono- or di-alkylamino group or a nitrogen-containing heterocyclic group, which may have a substituent, examples of said substituent include sulfo, carboxy, a phosphono group, sulfamoyl, carbamoyl, a hydroxy group, alkoxy (which may be substituted by a hydroxy group), amino, mono- or di-alkylamino, mono- or di-arylamino, acetylamino, ureide, alkyl, nitro, cyano, a halogen atom, alkylsulfonyl and alkylthio. Therefore, said mono- or di-alkylamino group or said nitrogen-containing heterocyclic group may have one or more kinds of the groups selected from among them, as a substituent. Further, examples of said substituent can include a heterocyclic group or an allyloxy group in addition to the above. Said mono- or di-alkylamino group or said nitrogen-containing heterocyclic group may have usually 1 to 4 and preferably 1 to 3 of one or more kinds of substituents among them.

Examples of the above alkoxy group can usually include (C1 to C8) alkoxy, preferably (C1 to C6) alkoxy and more preferably (C1 to C4) alkoxy.

Among the above substituents, examples of preferable groups include a sulfo group, a carboxy group, an alkoxy group (which may be substituted by a hydroxy group) and a hydroxy group.

Examples of the alkyl of the mono- or di-alkylamino group can usually include (C1 to C8) alkyl, preferably (C1 to C6) alkyl and more preferably (C1 to C4) alkyl.

Examples of the mono-alkylamino group which may have a substituent as Y, can preferably include (C1 to C4) alkylamino substituted by a substituent selected from the group consisting of a sulfo group, a carboxy group, a (C1 to C4) alkoxy group (which may be substituted by a hydroxy group) and a hydroxy group as substituent, more preferably a (C2 to C3) alkylamino substituted by a substituent selected from the group consisting of a sulfo group, a (C2 to C3) alkoxy group (which may be substituted by a hydroxy group) and a hydroxy group, and further preferably an ethylamino group substituted by a group selected from the group consisting of a sulfo group, a hydroxyethoxy group and a hydroxy group.

Preferable examples of a substituent in the di-alkylamino group which may have a substituent as Y, can include a group selected from the group consisting of sulfo, carboxy, ureide, alkyl, alkoxy, a hydroxy group, cyano, nitro, a halogen atom and a heterocyclic group. Said di-alkylamino group may have 1 to 4 substituents and preferably 1 to 3 substituents of one or more kinds of substituents among them. More preferable substituents are sulfo, carboxy and a hydroxy group.

Preferable examples of the di-alkylamino group which may have a substituent can include a di(C1 to C4) alkylamino group in which either or both of the alkyl groups are substituted by a group selected from the group consisting of sulfo, carboxy and a hydroxy group, as a substituent, and can more preferably include a di(2-carboxyethyl) amino group.

Specific examples of the above mono- or di-alkylamino group include 2-sulfoethylamino, 2-carboxyethylamino, carboxymethylamino, 2-hydroxyethylamino, 2-ethoxy-2-ethylamino, 1-hydroxy-butylamino, 5-carboxy-pentylamino, 2-methoxy-ethylamino, 2-ethoxyethylamino, (2-hydroxy) ethoxyethylamino, di(2-hydroxyethyl)amino, di(2-carboxyethyl)amino and the like.

Preferable examples of the substituent in the nitrogen-containing heterocyclic group which may have a substituent include sulfo, carboxy, ureide, alkyl, alkoxy, a hydroxy group, cyano, nitro, a halogen atom and a heterocyclic group. Said nitrogen-containing heterocyclic group may have 1 to 4 substituents and preferably 1 to 3 substituents of one or more kinds of substituents among them. Specific more preferable examples of the substituent include methyl, ethyl, sulfo, carboxy and a hydroxy group.

In addition, preferable examples of the nitrogen-containing heterocyclic group as Y can include a 5 to 7-membered nitrogen-containing heterocyclic group which may have a group selected from the group consisting of methyl, ethyl, sulfo, carboxy and a hydroxy group and preferably from the group consisting of sulfo, carboxy and a hydroxy group, as a substituent. Examples thereof can include piperidino (piperidinyl), pyrrolidino (pyrrolidinyl) or piperazino, or unsubstituted morpholino. The porphyrazine coloring matter or a salt thereof according to claim 1 having morpholino (morpholinyl), 4-methylpiperidino, piperidino, pyrrolidino, pyrazinyl, 2-carboxypyrrolidino and 4-ethylpiperazino (4-ethylpiperazinyl), 2-sulfoethylamino, bis(2-carboxyethyl) amino, 2-hydroxyethylamino, 2-hydroxyethoxyethylamino, 2-ethylpiperidinyl, 3-methylpyridinyl, 3-methylpyrrolidinyl and the like as specific examples of those can described.

Preferable examples of the combination of X and Y include the following (1) or (2):

(1) When Y is an amino group or a hydroxy group (preferably, amino group), X is a naphthyl group having, sulfo, carboxy or a phosphono group as a substituent, preferably a naphthyl group having 1 to 3 sulfo groups and more preferably a naphthyl group having 2 sulfo groups;

(2) When Y is a mono- or di-(C1 to C4 alkyl)amino group having a group selected from the group consisting of sulfo, carboxy and a hydroxy group as a substituent, or a 5 to 7-membered nitrogen-containing heterocyclic group (preferably 5 to 6-membered nitrogen-containing heterocyclic group and further preferably morpholino group) having, as a substituent, a group selected from the group consisting of methyl, ethyl, sulfo, carboxy and a hydroxy group, preferably from the group consisting of sulfo, carboxy and a hydroxy group, X is an anilino group or a naphthylamino group having, as a substituent, at least one group selected from the group consisting of a sulfo group, a carboxy group, a methoxy group, a nitro group, a chlorine atom, and a hydroxy group, preferably from the group consisting of sulfo, carboxy and a hydroxy group, said naphthylamino group being preferably a naphthylamino group having, a group selected from the group consisting of sulfo and a hydroxy group, as a substituent.

It is more preferable to combine this preferable combination of X and Y with further preferable E, for example, C2 to C4 alkylene, more preferably ethylene ($-C_2H_4-$) or propylene ($-C_3H_6-$). In this case, it is further preferable that the 6-membered nitrogen-containing aromatic ring represented by the rings A to D in the formula (1) is a pyridine ring or a pyrazine ring, more preferably a pyridine ring.

Preferable examples of the compound of the formula (1) of the present invention can include the compounds named in (4) to (6) described in the foregoing section of "Means of Solving the Problems"

The compound of the above formula (1) can also form a salt by using sulfo, carboxy and phosphono group and the like contained in its molecule. When the compound of the formula (1) forms a salt, it is preferable that the salt is formed with each cation of an inorganic metal, ammonium or an organic base.

Examples of the inorganic metal include an alkali metal and an alkali earth metal. Examples of the alkali metal include lithium, sodium, potassium and the like. The alkali earth metal includes, for example, calcium, magnesium and the like.

Examples of the organic base particularly include an organic amine, for example, lower alkyl amines having 1 to 3 carbon atoms such as methylamine and ethylamine and mono-, di- or tri(lower alkanol amines having 1 to 4 carbon atoms)amine such as monoethanolamine, diethanolamine, triethanolamine, monoisopropanolamine, diisopropanolamine and triisopropanolamine.

Among them, particularly preferable examples of the salt include alkali metal salts such as sodium, potassium and lithium, onium salts of mono-, di- or tri(lower alkanol having 1 to 4 carbon atoms)amine such as monoethanolamine, diethanolamine, triethanolamine, monoisopropanolamine, diisopropanolamine and triisopropanolamine, and ammonium salts.

Specific examples of A, B, C, D, E, X and Y and the numbers b and c in the porphyrazine coloring matter represented by the above formula (1) of the present invention are shown in the table 1.

The following examples show typical compounds in order to specifically explain the coloring matter of the present invention, and it is not limited to them.

In addition, in the case that the nitrogen-containing heteroaromatic ring of A, B, C or D is a pyridine ring, the compound is obtained as a mixture of isomers when synthesized because positional isomers or the like of the nitrogen atom are present as described later. It is difficult to isolate these isomers and it is also difficult to identify them by analysis. For this reason, the mixture is usually used as it is, and only a structural formula is described, for convenience as described above, in the representation of structural formulas without distinguishing these isomers because no problem arises in the present invention even though the compound is a mixture of isomers thereof.

TABLE 1

| No. | A | B | C | D | E | X | Y | b | c |
|---|---|---|---|---|---|---|---|---|---|
| 1 | 2,3-Pyrido | Benzo | Benzo | Benzo | Ethylene | 4-Sulfoanilino | 2-Hydroxyethylamino | 2 | 1 |
| 2 | 2,3-Pyrido | Benzo | Benzo | Benzo | Ethylene | 6-Sulfo-1-naphthylamino | 2-Sulfoethylamino | 2 | 1 |
| 3 | 2,3-Pyrido | Benzo | Benzo | Benzo | Ethylene | 3,8-Disulfo-1-naphthylamino | Amino | 2 | 1 |
| 4 | 2,3-Pyrido | Benzo | Benzo | Benzo | Ethylene | 3,6-Disulfo-1-naphthylamino | 2-Hydroxyethoxyethylamino | 2 | 1 |
| 5 | 2,3-Pyrido | Benzo | Benzo | Benzo | Ethylene | 4-Sulfoanilino | 2-Hydroxyethoxyethylamino | 2 | 1 |
| 6 | 2,3 Pyrido | Benzo | Benzo | Benzo | Ethylene | 3,8-Disulfo-1-naphthylamino | Morpholino | 2 | 1 |
| 7 | 2,3-Pyrido | Benzo | Benzo | Benzo | Ethylene | 6,8-Disulfo-2-naphthylamino | Morpholino | 2 | 1 |
| 8 | 2,3-Pyrido | Benzo | Benzo | Benzo | Ethylene | 6-Sulfo-1-naphthylamino | 2-Sulfoethylamino | 2 | 1 |
| 9 | 2,3-Pyrido | Benzo | Benzo | Benzo | Ethylene | 3,8-Disulfo-1-naphthylamino | Amino | 2 | 1 |
| 10 | 2,3-Pyrido | Benzo | Benzo | Benzo | Ethylene | 3,6-Disulfo-1-naphthylamino | 2-Hydroxyethoxyethylamino | 2 | 1 |
| 11 | 2,3-Pyrido | Benzo | Benzo | Benzo | Ethylene | 4-Sulfoanilino | 2-Hydroxyethoxyethylamino | 2 | 1 |
| 12 | Benzo | Benzo | 2,3-Pyrido | Benzo | Ethylene | 3,8-Disulfo-1-naphthylamino | Morpholino | 2 | 1 |
| 13 | Benzo | Benzo | 2,3-Pyrido | Benzo | Ethylene | 6,8-Disulfo-2-naphthylamino | Morpholino | 2 | 1 |
| 14 | 2,3-Pyrido | Benzo | Benzo | Benzo | Ethylene | 2,5-Disulfoanilino | Morpholino | 2 | 1 |
| 15 | 2,3-Pyrido | Benzo | Benzo | Benzo | Ethylene | 2,4-Disulfoanilino | Morpholino | 2 | 1 |

TABLE 2

| No. | A | B | C | D | E | X | Y | b | c |
|---|---|---|---|---|---|---|---|---|---|
| 16 | 2,3-Pyrido | Benzo | Benzo | Benzo | Ethylene | 3-Sulfoanilino | 2-Sulfoethylamino | 2 | 1 |
| 17 | 2,3-Pyrido | Benzo | Benzo | Benzo | Ethylene | 4-Sulfoanilino | 2-Sulfoethylamino | 2 | 1 |
| 18 | 2,3-Pyrido | Benzo | Benzo | Benzo | Ethylene | 4-Sulfoanilino | Bis(2-carboxyethyl)amino | 2 | 1 |
| 19 | 2,3-Pyrido | Benzo | Benzo | Benzo | Ethylene | 3,5-Dicarboxyanilino | 2-Sulfoethylamino | 2 | 1 |
| 20 | 2,3-Pyrido | Benzo | Benzo | Benzo | Ethylene | 2,5-Disulfoanilino | 4-Ethylpiperazino | 2 | 1 |
| 21 | 2,3-Pyrido | Benzo | Benzo | Benzo | Ethylene | 2,5-Disulfoanilino | 2-Ethylpiperidino | 2 | 1 |
| 22 | 2,3-Pyrido | Benzo | Benzo | Benzo | Ethylene | 2,5-Disulfoanilino | 3-Methylpyrrolidino | 2 | 1 |
| 23 | 2,3-Pyrido | Benzo | Benzo | Benzo | Ethylene | 2,5-Disulfoanilino | 2-Carboxypyrrolidino | 2 | 1 |
| 24 | 2,3-Pyrido | Benzo | Benzo | Benzo | Ethylene | 2,5-Disulfoanilino | Pyrrolidino | 2 | 1 |
| 25 | 2,3-Pyrido | 2,3-Pyrido | Benzo | Benzo | Ethylene | 3,8-Disulfo-1-naphthylamino | Amino | 1 | 1 |
| 26 | 2,3-Pyrido | Benzo | 2,3-Pyrido | Benzo | Ethylene | 3,6-Disulfo-1-naphthylamino | 2-Hydroxyethoxyethylamino | 1 | 1 |
| 27 | 2,3-Pyrido | 2,3-Pyrido | Benzo | Benzo | Ethylene | 4-Sulfoanilino | 2-Hydroxyethoxyethylamino | 1 | 1 |

TABLE 2-continued

| No. | A | B | C | D | E | X | Y | b | c |
|---|---|---|---|---|---|---|---|---|---|
| 28 | 2,3-Pyrido | 2,3-Pyrido | Benzo | Benzo | Ethylene | 3,8-Disulfo-1-naphthylamino | Morpholino | 1 | 1 |
| 29 | 2,3-Pyrido | 2,3-Pyrido | Benzo | Benzo | Ethylene | 6,8-Disulfo-2-naphthylamino | Morpholino | 1 | 1 |
| 30 | 2,3-Pyrido | Benzo | 2,3-Pyrido | Benzo | Ethylene | 2,5-Disulfoanilino | Morpholino | 1 | 1 |
| 31 | 2,3-Pyrido | Benzo | 2,3-Pyrido | Benzo | Ethylene | 2,4-Disulfoanilino | Morpholino | 1 | 1 |

TABLE 3

| No. | A | B | C | D | E | X | Y | b | c |
|---|---|---|---|---|---|---|---|---|---|
| 32 | 2,3-Pyrido | Benzo | 2,3-Pyrido | Benzo | Propylene | 4-Sulfoanilino | 2-Hydroxyethylamino | 1 | 1 |
| 33 | 2,3-Pyrido | Benzo | 2,3-Pyrido | Benzo | Ethylene | 3,5-Dicarboxyanilino | 2-Sulfoethylamino | 1 | 1 |
| 34 | 2,3-Pyrido | 2,3-Pyrido | Benzo | Benzo | Ethylene | 3-Sulfoanilino | 2-Sulfoethylamino | 1 | 1 |
| 35 | 2,3-Pyrido | Benzo | 2,3-Pyrido | Benzo | Ethylene | 4-Sulfoanilino | 2-Sulfoethylamino | 1 | 1 |
| 36 | 2,3-Pyrido | Benzo | 2,3-Pyrido | Benzo | Ethylene | 4-Sulfoanilino | Bis(2-carboxyethyl)amino | 1 | 1 |
| 37 | 2,3-Pyrido | Benzo | 2,3-Pyrido | Benzo | Butylene | 6-Sulfo-1-naphthylamino | 2-Sulfoethylamino | 1 | 1 |
| 38 | 2,3-Pyrido | Benzo | 2,3-Pyrido | Benzo | Ethylene | 3,8-Disulfo-1-naphthylamino | Amino | 1 | 1 |
| 39 | 2,3-Pyrido | Benzo | 2,3-Pyrido | Benzo | Ethylene | 3,6-Disulfo-1-naphthylamino | 2-Hydroxyethoxyethylamino | 1 | 1 |
| 40 | 2,3-Pyrido | 2,3-Pyrido | 2,3-Pyrido | Benzo | Ethylene | 4-Sulfoanilino | 2-Hydroxyethoxyethylamino | 0 | 1 |
| 41 | 2,3-Pyrido | 2,3-Pyrido | 2,3-Pyrido | Benzo | Ethylene | 3,8-Disulfo-1-naphthylamino | Morpholino | 0 | 1 |
| 42 | 2,3-Pyrido | 2,3-Pyrido | 2,3-Pyrido | Benzo | Ethylene | 6,8-Disulfo-2-naphthylamino | Morpholino | 0 | 1 |
| 43 | 2,3-Pyrido | 2,3-Pyrido | 2,3-Pyrido | Benzo | Ethylene | 2,5-Disulfoanilino | Morpholino | 0 | 1 |
| 44 | 2,3-Pyrido | 2,3-Pyrido | 2,3-Pyrido | Benzo | Ethylene | 2,4-Disulfoanilino | Morpholino | 0 | 1 |
| 45 | 2,3-Pyrido | 2,3-Pyrido | 2,3-Pyrido | Benzo | Ethylene | 3,5-Dicarboxyanilino | 2-Sulfoethylamino | 0 | 1 |
| 46 | 2,3-Pyrido | 2,3-Pyrido | Benzo | 2,3-Pyrido | Ethylene | 4-Sulfoanilino | 2-Hydroxyethylamino | 0 | 1 |
| 47 | 2,3-Pyrido | 2,3-Pyrido | Benzo | 2,3-Pyrido | Ethylene | 6-Sulfo-1-naphthylamino | 2-Sulfoethylamino | 0 | 1 |

TABLE 4

| No. | A | B | C | D | E | X | Y | b | c |
|---|---|---|---|---|---|---|---|---|---|
| 48 | 2,3-Pyrido | Benzo | 2,3-Pyrido | 2,3-Pyrido | Ethylene | 3,6,8-Trisulfo-1-naphthylamino | Morpholino | 0 | 1 |
| 49 | 2,3-Pyrido | Benzo | 2,3-Pyrido | 2,3-Pyrido | Ethylene | 3,6,8-Trisulfo-1-naphthylamino | 2-Sulfoethylamino | 0 | 1 |
| 50 | Benzo | 2,3-Pyrido | 2,3-Pyrido | 2,3-Pyrido | Ethylene | 3,6,8-Trisulfo-1-naphthylamino | 2-Hydroxyethylamino | 0 | 1 |
| 51 | Benzo | 2,3-Pyrido | 2,3-Pyrido | 2,3-Pyrido | Ethylene | 3,6,8-Trisulfo-1-naphthylamino | 2-Hydroxyethoxyethylamino | 0 | 1 |
| 52 | 2,3-Pyrido | Benzo | Benzo | 2,3-Pyrido | Butylene | 2,5-Disulfoanilino | 4-Ethylpiperazino | 1 | 1 |
| 53 | 2,3-Pyrido | Benzo | Benzo | 2,3-Pyrido | Butylene | 2,5-Disulfoanilino | 2-Ethylpiperidino | 1 | 1 |
| 54 | 2,3-Pyrido | Benzo | Benzo | 2,3-Pyrido | Butylene | 2,5-Disulfoanilino | 3-Methylpyrrolidino | 1 | 1 |
| 55 | 2,3-Pyrido | Benzo | Benzo | 2,3-Pyrido | Butylene | 2,5-Disulfoanilino | 2-Carboxypyrrolidino | 1 | 1 |
| 56 | 2,3-Pyrido | Benzo | Benzo | 2,3-Pyrido | Butylene | 2,5-Disulfoanilino | Pyrrolidino | 1 | 1 |
| 57 | 2,3-Pyrido | Benzo | 2,3-Pyrido | Benzo | Propylene | 2,5-Disulfoanilino | 4-Ethylpiperazino | 1 | 1 |
| 58 | 2,3-Pyrido | Benzo | 2,3-Pyrido | Benzo | Propylene | 2,5-Disulfoanilino | 2-Ethylpiperidino | 1 | 1 |

TABLE 4-continued

| No. | A | B | C | D | E | X | Y | b | c |
|---|---|---|---|---|---|---|---|---|---|
| 59 | 2,3-Pyrido | Benzo | 2,3-Pyrido | Benzo | Propylene | 2,5-Disulfoanilino | 3-Methylpyrrolidino | 1 | 1 |
| 60 | 2,3-Pyrido | Benzo | 2,3-Pyrido | Benzo | Propylene | 2,5-Disulfoanilino | 2-Carboxypyrrolidino | 1 | 1 |
| 61 | 2,3-Pyrido | Benzo | 2,3-Pyrido | Benzo | Propylene | 2,5-Disulfoanilino | Pyrrolidino | 1 | 1 |
| 62 | 2,3-Pyrido | 2,3-Pyrido | 2,3-Pyrido | Benzo | Ethylene | 2,5-Disulfoanilino | 4-Ethylpiperazino | 0 | 1 |
| 63 | 2,3-Pyrido | 2,3-Pyrido | 2,3-Pyrido | Benzo | Ethylene | 2,5-Disulfoanilino | 2-Ethylpiperidino | 0 | 1 |
| 64 | 2,3-Pyrido | Benzo | 2,3-Pyrido | 2,3-Pyrido | Ethylene | 2,5-Disulfoanilino | 3-Methylpyrrolidino | 0 | 1 |

The porphyrazine coloring matter of the present invention is usually used alone, but optionally may be used as a mixture with another coloring matter, for example, a known cyan coloring matter.

In addition, when the porphyrazine coloring matter of the present invention is used as a cyan coloring matter, it is a preferable aspect that it is used as a mixture of a compound having one nitrogen-containing heteroaromatic ring and a compound having two or three nitrogen-containing heteroaromatic rings, more preferably as a mixture of a compound having one nitrogen-containing heteroaromatic ring and a compound having two nitrogen-containing heteroaromatic rings. As for the ratio of the both in the case, the ratio of the compound having one nitrogen-containing heteroaromatic ring is 10 to 100%, preferably 50 to 95% and more preferably 60 to 93%, and the ratio of the compound having two or three nitrogen-containing heteroaromatic rings (preferably compound having two) is 0 to 90%, preferably 5 to 50% and more preferably about 7 to 40%, relative to the total of the both.

Further, when the porphyrazine coloring matter of the present invention is used as a mixture with a known cyan coloring matter, the coloring matter to be mixed is preferably a phthalocyanine coloring matter. When used as said mixture, the ratio of the porphyrazine coloring matter of the present invention and another coloring matter can be appropriately determined according to the intended use and the like. For example, the porphyrazine coloring matter of the present invention is 1 to 100%, preferably 10 to 95% and more preferably 20 to 90% relative to the mixture, and the rest is another coloring matter, for example, a phthalocyanine coloring matter.

In this connection, the above "%" means "% by weight" in any case.

The production method of the compound of the above formula (1) will be explained.

Firstly, a copper porphyrazine compound represented by the following formula (6) is synthesized.

The copper porphyrazine compound represented by the formula (6) described later is obtained by, for example, reacting said nitrogen-containing heteroaromatic dicarboxylic acid derivative with said phthalic acid derivative in the presence of a catalyst and a copper compound. By changing the molar ratio in the reaction of said nitrogen-containing heteroaromatic dicarboxylic acid derivative with said phthalic acid derivative, the number of said nitrogen-containing heteroaromatic ring and the number of the benzene ring in A, B, C and D can be controlled.

For example, when 1 to 3 of four 6-membered aromatic rings of A to D in the present invention is said nitrogen-containing heteroaromatic ring and the rest are benzene rings, the intended compound can be obtained by using said nitrogen-containing heteroaromatic dicarboxylic acid derivative and said phthalic acid derivative in such a ratio that each thereof is in the range of 0.25 to 0.75 mol and the total of the both is 1 mol according to the content ratio.

For example, when the number of said nitrogen-containing heteroaromatic ring is one and that of the benzene ring is three, said nitrogen-containing heteroaromatic dicarboxylic acid derivative can be used in the ratio of 0.25 mol and the phthalic acid derivative can be used in the ratio of 0.75 mol. In addition, when the number of said nitrogen-containing heteroaromatic ring is two and that of the benzene ring is two, the nitrogen-containing heteroaromatic dicarboxylic acid derivative can be used in the ratio of 0.5 mol and the phthalic acid derivative can be used in the ratio of 0.5 mol. Therefore, when the number of said nitrogen-containing heteroaromatic ring is 1 to 2 and that of the benzene ring is 2 to 3, said nitrogen-containing heteroaromatic dicarboxylic acid derivative can be used in a ratio of 0.25 to 0.5 mol and said phthalic acid derivative can be used in a ratio of 0.5 to 0.75 mol.

Examples of said nitrogen-containing heteroaromatic dicarboxylic acid derivative include 6-membered ring nitrogen-containing heteroaromatic dicarboxylic acid derivatives having a carboxy group or a reactive group (such as acid amide group, imide group, acid anhydride group and carbonitrile group) derived therefrom, respectively in two adjacent positions.

Specific examples thereof include dicarboxylic acid compounds such as quinolinic acid, 3,4-pyridinedicarboxylic acid, 2,3-pyrazinedicarboxylic acid; acid anhydrides such as quinolinic anhydride, 3,4-pyridinedicarboxylic anhydride, 2,3-pyrazinedicarboxylic anhydride; amide compounds such as pyridine-2,3-dicarboxamide; dicarboxylic acid monoamide compounds such as pyrazine-2,3-dicarboxylic acid monoamide; acid imide compounds such as quinolinic acid imide; and dicarbonitrile compounds such as pyridine-2,3-dicarbonitrile, pyrazine-2,3-dicarbonitrile. In addition, examples of the phthalic acid derivative include phthalic acid, phthalic anhydride, phthalamide, phthalamic acid, phthalimide, phthalonitrile, 1,3-diiminoisoindoline, 2-cyanobenzamide and the like.

The synthesis method of the copper porphyrazine compound usually includes two methods called nitrile method and Wyler method, which are different in reaction conditions and the like. The nitrile method is a method of synthesizing porphyrazine using a dicarbonitrile compound such as pyridine-2,3-dicarbonitrile, pyrazine-2,3-dicarbonitrile and phthalonitrile as a raw material.

On the other hand, Wyler method uses, as a raw material, a dicarboxylic acid compound such as phthalic acid, quinolinic acid, 3,4-pyridinedicarboxylic acid and 2,3-pyrazinedicarboxylic acid, an acid anhydride compound such as phthalic anhydride, quinolinic anhydride, 3,4-pyridinedicarboxylic anhydride and 2,3-pyrazinedicarboxylic anhydride, a dicarboxamide compound such as phthalamide and pyridine-2,3-dicarboxamide, a dicarboxylic acid monoamide compound such as phthalamic acid, pyrazine-2,3-dicarboxylic acid monoamide, and an acid imide compound such as phthalimide and quinolinic acid imide. In addition, Wyler method inevitably requires addition of urea, and the amount of urea to be used is 5 to 100 times by mole relative to the total 1 mol of the nitrogen-containing heteroaromatic dicarboxylic acid derivative and the phthalic acid derivative.

Formula (6)

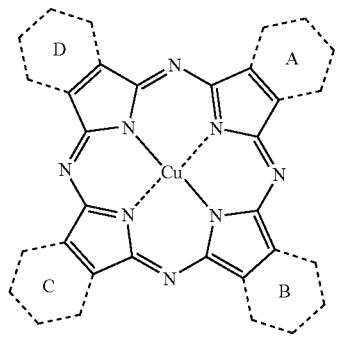

(6)

(Wherein A, B, C and D have the Same Meanings as Described Above.)

The reaction is carried out in the presence of a solvent, and as a solvent in the nitrile method, an organic solvent having a boiling point of 100° C. or more, more preferably 130° C. or more is used. Said organic solvent include, for example, n-amyl alcohol, n-hexanol, cyclohexanol, 2-methyl-1-pentanol, 1-heptanol, 1-octanol, 2-ethylhexanol, N,N-dimethylaminoethanol, benzyl alcohol, ethylene glycol, propylene glycol, trichlorobenzene, chloronaphthalene, nitrobenzene, quinoline, sulfolane, urea and the like.

In addition, as a solvent in Wyler method, an aprotic organic solvent having a boiling point of 150° C. or more, more preferably 180° C. or more is used. Examples thereof include trichlorobenzene, chloronaphthalene, nitrobenzene, quinoline, sulfolane, urea and the like.

The amount of the solvent to be used is 1 to 100 times by mass relative to the total of the nitrogen-containing heteroaromatic dicarboxylic acid derivative and the phthalic acid derivative.

As the catalyst, the followings can be used:

In the nitrile method, examples thereof include amines such as quinoline, 1,8-diazabicyclo[5,4,0]-7-undecene, tributylamine, ammonia and N,N-dimethylaminoethanol, or alkali metal alcoholates such as sodium ethoxide and sodium methoxide;

In Wyler method, examples thereof include ammonium molybdate, boric acid and the like.

The addition amount of the catalyst is 0.001 to 1 times by mole relative to the total 1 mol of the nitrogen-containing heteroaromatic dicarboxylic acid derivative and the phthalic acid derivative.

Examples of the copper compound include metal copper and halide, carboxylate, sulfate, nitrate, acetylacetonate and complexes of copper and the like, for example, copper chloride, copper bromide, copper acetate, copper acetylacetonate and the like.

When porphyrazine having a central metal other than copper is desired to be synthesized, a corresponding metal salt can be used or exchange reaction of the central metal can be carried out according to a conventional method after synthesizing the porphyrazine ring.

The amount of the copper compound to be used is 0.15 to 0.35 times by mole relative to the total 1 mol of the nitrogen-containing heteroaromatic dicarboxylic acid derivative and the phthalic acid derivative.

The reaction temperature in nitrile method is usually 100 to 200° C. and preferably 130 to 170° C.

On the other hand, the reaction temperature in Wyler method is 150 to 300° C. and preferably 170 to 220° C.

The reaction time varies depending on the reaction conditions, but is usually 1 to 40 hours. After completion of the reaction, the intended product is removed by filtration, washed and dried to obtain the copper porphyrazine coloring matter.

A compound in which two of A, B, C and D in the above formula (6) are pyridine rings and the rest two are benzene rings, namely copper dibenzobis(2,3-pyrido)porphyrazine is exemplified to explain the synthesis method more specifically.

By reacting quinolinic acid (0.5 mol), phthalic anhydride (0.5 mol), copper (II) chloride (0.25 mol), ammonium phosphomolybdate (0.004 mol) and urea (6 mol) in a sulfolane solvent at 200° C. for 5 hours, the copper dibenzobis(2,3-pyrido) porphyrazine represented by the above formula (6) in which two of A, B, C and D are pyridine rings and the rest two are benzene rings is obtained. The reactivity varies depending on the kind and amount of quinolinic acid, phthalic anhydride, metal compound, solvent, catalyst and the like to be used, and the method is not limited to the above.

In addition, in the case that the synthesis is carried out in the above synthesis method, the main component is copper dibenzobis(2,3-pyrido)porphyrazine. This compound has five kinds of isomers {the formulas (7-A) to (7-E)} each of which has different positions of the pyridine ring and the pyridine ring nitrogen atom, and they are produced all together in this synthesis method. At the same time, the copper tribenzo(2,3-pyrido)porphyrazine {the formula (8) described later} represented by the above formula (6) in which one of A to D is a pyridine ring and the rest three are benzene rings and the copper benzotris(2,3-pyrido)porphyrazine represented by the above formula (6) in which three of A to D are pyridine rings and the rest one is a benzene ring are by-produced, and further these compounds contains a positional isomer of the pyridine ring nitrogen atom {the formula (9-A) to (9-D) described later}, resulting in that they are complex mixtures. In addition, the copper tetrakis(2,3-pyrido)porphyrazine and copper phthalocyanine (copper tetrabenzoporphyrazine) are also produced, though in a small amount. Usually, it is difficult to isolate only the intended product from these mixtures. In the obtained compound, two of A to D are pyridine rings and the rest two are benzene rings as an average value, and therefore it is directly used as the copper dibenzobis(2,3-pyrido) porphyrazine in most cases.

In the above description, the copper dibenzobis(2,3-pyrido)porphyrazine in which two of A to D are pyridine rings and the rest two are benzene rings are mentioned, while in the case of the nitrogen-containing heteroaromatic ring other than pyridine, the compound in which two of A to D are said nitrogen-containing heteroaromatic rings and the rest two are benzene rings can be likewise obtained by carrying out the reaction corresponding to said nitrogen-containing heteroaromatic ring, in accordance with the above manner. Further, a mixture of a compound in which one or three of A to D are nitrogen-containing heteroaromatic rings or a compound in which one of A to D is a nitrogen-containing heteroaromatic ring and a compound in which two or/and three of A to D are nitrogen-containing heteroaromatic rings can be obtained as well, by changing the amounts of the nitrogen-containing heteroaromatic dicarboxylic acid derivatives and the phthalic acid derivatives to be used, respectively in the range of about 0.25 to 0.75 mol and in such a ratio that the total of the both is 1 mol, according to the rate of the nitrogen-containing heteroaromatic ring and the benzene ring in the intended compound.

Formula (7-A) to (7-E)

(7-A)
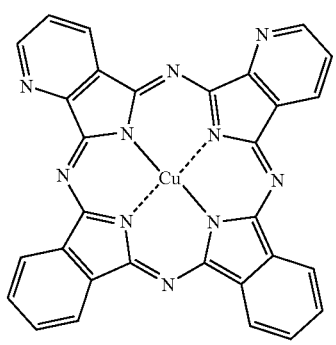

(7-B)
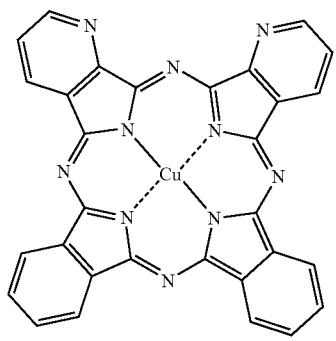

(7-C)
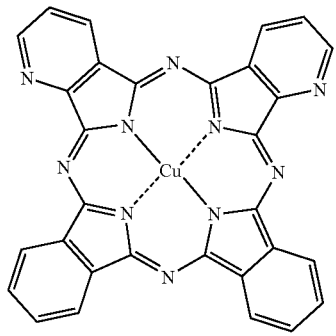

(7-D)
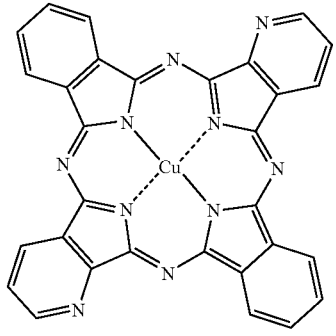

(7-E)
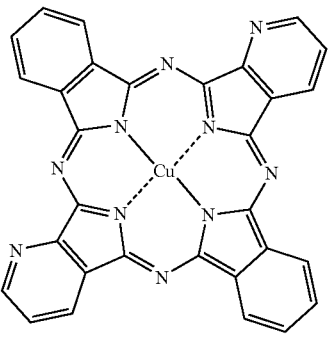

Formula (8)

(8)
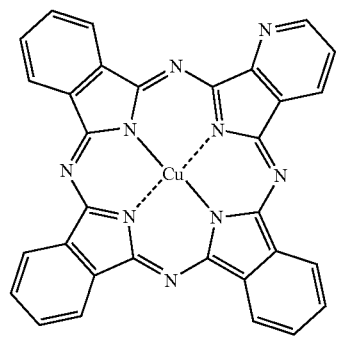

Formula (9-A) to (9-D)

(9-A)
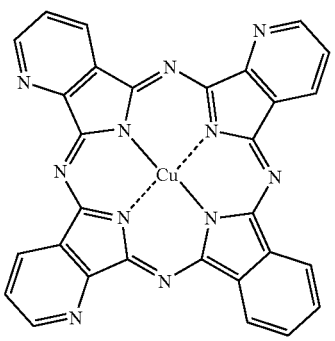

(9-B)
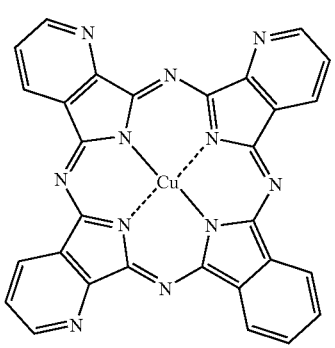

-continued (9-C)

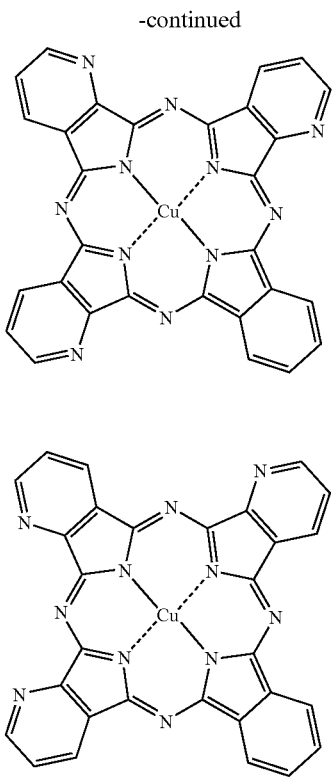

(9-D)

Next, the copper chlorosulfonyl porphyrazine compound represented by the above formula (3) can be obtained by chlorosulfonylation of the copper porphyrazine coloring matter represented by the above formula (6) in chlorosulfonic acid. In addition, it can be also obtained by sulfonation of the copper porphyrazine compound represented by the formula (6) in sulfuric acid or fuming sulfuric acid, and then by conversion of the sulfo group to a chlorosulfonyl group with a chlorination agent. In this connection, by the above chlorosulfonylation or sulfonation, the chlorosulfonyl group or the sulfo group is introduced on the benzene ring of A to D in the formula (6), not on said heteroaromatic ring. On one benzene ring, one chlorosulfonyl group or one sulfo group is usually introduced, so the number of the chlorosulfonyl group or the sulfo group which are introduced is usually within the number of the benzene ring. Therefore, the number (n) of the chlorosulfonyl group in the formula (3) is 1 to 3 corresponding to the number of the benzene ring in the compound of the formula (3).

The copper chlorosulfonyl porphyrazine compound represented by the formula (3) can be also obtained by another synthesis method. For example, by cyclocondensation of sulfo phthalic acid having one sulfo group and 6-membered nitrogen-containing heteroaromatic dicarboxylic acid such as quinolinic acid or derivatives thereof, the copper porphyrazine coloring matter having a sulfo group, which is represented by the following formula (10), is synthesized, and then by converting the sulfo group to a chlorosulfonyl group, an intended compound of the above formula (3) can be obtained.

The number (n) of the chlorosulfonyl group in the obtained compound of the formula (3) is 1 to 3 on an average as described above and preferably 2 to 3 on an average.

Formula (10)

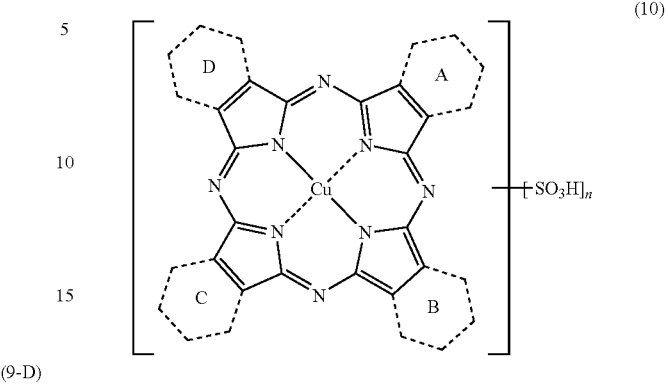

[Wherein, A, B, C, D and n have the same meanings as those in the above formula (3)]

It is preferable that chlorosulfonylation of the copper porphyrazine coloring matter represented by the above formula (6) is usually carried out with chlorosulfonic acid 3 to 20 times by weight and preferably 5 to 10 times by weight of said coloring matter, as a solvent. The reaction temperature is usually 100 to 150° C. and preferably 120 to 150° C. The reaction time varies depending on the reaction conditions such as reaction temperature, and is usually 1 to 10 hours. In this case, the substituent of the obtained copper porphyrazine compound is usually a mixture of chlorosulfonyl group and sulfo group, it is preferable in the present invention that a chlorination agent such as thionyl chloride is further added to said reaction liquid after the reaction with a chlorosulfonyl acid solvent and the reaction is further carried out for converting the sulfo group to a chlorosulfonyl group so that the substituent is all composed of chlorosulfonyl groups.

The amount of the chlorination agent to be added is approximately 0.5 to 10 equivalents and preferably 0.5 to 5 equivalents, relative to the sulfo group of the sulfo-substituted copper porphyrazine compound which is by-produced in the reaction in a chlorosulfonic acid solvent. Examples of the chlorination agent include chlorosulfonic acid, thionyl chloride, sulfuryl chloride, phosphorus trichloride, phosphorus pentachloride, phosphorus oxychloride and the like, but it is not limited thereto.

The conversion of the sulfo group of the sulfo-copper porphyrazine coloring matter represented by the above formula (10) to a chlorosulfonyl group can be carried out by reacting said coloring matter with the above chlorination agent. Examples of the solvent to be used in said chlorination reaction include sulfuric acid, fuming sulfuric acid, chlorosulfonic acid, benzene, toluene, nitrobenzene, chlorobenzene, N,N-dimethylformamide, N,N-dimethylacetoamide and the like, but it is not limited thereto.

Next, by reacting the copper chlorosulfonyl porphyrazine compound obtained above with an organic amine represented by the following formula (4) and with an aminating agent (ammonia or ammonia-producing compound) in a water solvent at about pH 8 to 10 and 5 to 70° C. for 1 to 20 hours, the intended compound of the formula (1) can be obtained. As an aminating agent to be used for the reaction, ammonia or a compound producing ammonia (ammonia-producing compound) in the above reaction can be used, and examples thereof include ammonium salts such as ammonium chloride and ammonium sulfate, urea, ammonia water, ammonia gas and the like. It is, however, not limited thereto. In this connection, the reaction of the copper chlorosulfonyl porphyrazine coloring matter with an organic amine and an aminating agent is usually carried out in a water solvent as described above.

Formula (4)

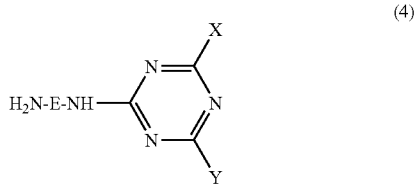

(4)

(Wherein, E, X and Y have the same meanings as described above.)

In addition, the amount of the organic amine to be used is usually 1 or more times by mole of the theoretical Value (the number of moles which is necessary in order that the value of c in the formula (1) is 0.1 to 3), relative to 1 mol of the copper chlorosulfonyl porphyrazine compound, but it varies depending on the reactivity of the organic amine and on reaction conditions and not limited thereto.

Usually, the amount of said organic amine to be used is approximately 1 to 3 times by mole and preferably 1 to 2 times by mole of the above theoretical value.

The production method of the organic amine represented by the formula (4) will be explained.

The organic amine represented by the formula (4) can be produced by a known method.

For example, 0.95 to 1.1 mol of an anilines or a naphthylamines corresponding X and 1 mol of 2,4,6-trichloro-S-triazine (cyanuric chloride) are reacted in water under the conditions of about pH 3 to 7, 5 to 40° C. and 2 to 12 hours to obtain a first condensate.

Then, in the case that Y is an amino group, a second condensate is obtained by reacting 1 mol of the obtained first condensate with 0.95 to 2.0 mol of an aminating agent (the above ammonia and the like) under the conditions of about pH 4 to 10, 5 to 80° C. and 0.5 to 12 hours.

On the other hand, in the case that Y is a hydroxy group, a second condensate is obtained by adding an alkali metal hydroxide such as sodium hydroxide to a reaction liquid of the first condensate and then by reacting under the conditions of about pH 4 to 10, 5 to 80° C. and 0.5 to 12 hours.

In addition, in the case that Y is the above alkylamino group or the above dialkylamino group, a second condensate is obtained by reacting 1 mol of the first condensate with 0.95 to 1.1 mol of an amines corresponding said amino group under the conditions of pH 4 to 10, 5 to 80° C. and 0.5 to 12 hours.

Then, by reacting 1 mol of the obtained second condensate with 1 to 50 mol of an alkylene diamines corresponding —HN-E-NH— under the conditions of about pH 9 to 12, 5 to 90° C. and 0.5 to 8 hours, a compound of the above formula (4) is obtained. Examples of a pH adjuster in the condensation usually include alkali metal hydroxides such as sodium hydroxide and potassium hydroxide, alkali metal carbonates such as sodium carbonate and potassium carbonate, or the like. In this connection, the order of condensation is appropriately determined according to the reactivity of each compound, and not limited to the above.

In addition, the copper porphyrazine coloring matters represented by the above formulas (1) and (2) can be obtained by reaction of the compounds represented by the above formula (3) and by the formula (4). This reaction does not particularly require the anhydrous condition. For this reason, it can be considered in theory that some of the chlorosulfonyl groups in the formula (3) are hydrolyzed with water which is mixed in the reaction system to by-produce a compound in which they are converted to the sulfonic acid groups, resulting in that said by-products are mixed in the intended coloring matter of the formula (1) or (2).

However, it is difficult to distinguish between unsubstituted sulfamoyl groups and sulfonic acid groups in mass spectrometry, and therefore in the present invention, the chlorosulfonyl groups in the formula (3) other than the groups which are reacted with the organic amine represented by the formula (4) are all described as converted to unsubstituted sulfamoyl groups.

As for the copper porphyrazine coloring matter represented by the above formula (1) or (2) obtained as the above, b is 0 to 2.9 and c is 0.1 to 3, and preferably b is 1 to 2.5 and c is 0.5 to 1.

In addition, in some of the copper porphyrazine coloring matters represented by the above formulas (1) and (2), impurities in which copper porphyrazine rings (Pz) form a dimer (for example, Pz-L-Pz) or a trimer via a divalent linking group (L) are by-produced, and they may occasionally come to be mixed in the reaction products. Examples of the divalent linking group represented by the above L include —SO$_2$—, —SO$_2$—NH—SO$_2$— and the like, and as for the trimer, a by-product having above two kinds of Ls in combination is also formed occasionally.

The thus obtained copper porphyrazine coloring matter of the present invention can be separated by filtration or the like after aciding out or salting out. It is preferable to carry out the salting out, for example, in the acidic to alkaline range and preferably in the range of pH 1 to 11. The temperature in the salting out is not particularly limited, but usually 40 to 80° C. and preferably 50 to 70° C. More specifically, it is preferable that a reaction liquid containing the copper porphyrazine coloring matter of the present invention is heated to the above temperature followed by addition of sodium chloride or the like, and then the pH is adjusted in the above range, for the salting out.

The copper porphyrazine coloring matter represented by the above formula (1) or the above formula (2) of the present invention which is synthesized in the above method is obtained in free acid form or its salt form. Its free acid can be obtained by, for example, aciding out. On the other hand, its salt can be obtained by salting out, and when a desired salt is not obtained by salting out, a usual salt-exchange method can be used, for example, a method in which a desired organic or inorganic base is added to its free acid.

Next, the ink of the present invention will be explained. The porphyrazine coloring matter of the above formula (1) and a salt thereof which are produced in the above method exhibit a vivid cyan color. Therefore, the ink containing these can be mainly used as a cyan ink. Said ink may be used not only as a cyan ink having a high concentration but also as a cyan ink having a low concentration of coloring matter (referred to as light cyan ink, photo cyan ink or the like) which is used for reproducing gradation part of images smoothly or for reducing granular appearance of hypochromic regions. In addition, the coloring matter of the present invention may be mixed with a yellow coloring matter and used as a green ink, while it may be mixed with a magenta coloring matter and used as a violet or blue ink. Further, the coloring matter of the present invention can be mixed with a plurality of coloring matters to make an ink, which can be used as a dark yellow, gray or black ink.

The ink of the present invention is prepared using water as a medium.

When this ink is used as an ink for inkjet, the porphyrazine coloring matter of the present invention (hereinafter, when the term "porphyrazine coloring matter of the present invention" is used, it means any form of a free porphyrazine coloring matter, a salt thereof, and a mixture of the both, unless otherwise noted) to be used for it is preferably a compound containing less amount of anion such as $Cl^-$ and $SO_4^{2-}$. The content is, only as a guide, 5% by mass or below, preferably 3% by mass or below and further preferably 1% by mass or below as the total content of $Cl^-$ and $SO_4^{2-}$ in the porphyrazine coloring matter; and 1% by mass or below, preferably 0.5% or below and further preferably 0.1% or below in the ink.

In order to produce the porphyrazine coloring matter of the present invention with less $Cl^-$ and $SO_4^{2-}$, for example, desalting treatment can be carried out by an ordinary method using a reverse osmosis membrane, by a method where the dry form or wet cake of porphyrazine coloring matter of the present invention is stirred in aqueous alcohol, and by the like method.

In the latter case, alcohol to be used is a lower alcohol having 1 to 4 carbon atoms, preferably an alcohol having 1 to 3 carbon atoms and further preferably methanol, ethanol, n-propanol or 2-propanol. The method of desalination by heating near to the boiling point of alcohol to be used and then by cooling can be employed.

The coloring matter in a dry state can be also obtained by that the porphyrazine coloring matter of the present invention subjected to desalting treatment in aqueous alcohol is removed by filtration and dried by a conventional method.

The content of $Cl^-$ and $SO_4^{2-}$ in said coloring matter is measured by, for example, an ion chromatography.

When the ink of the present invention is an ink for inkjet recording, it is preferable that the porphyrazine coloring matter to be used for it also has a less content of impurities other than the above $Cl^-$ and $SO_4^{2-}$, such as each ion of heavy metal such as zinc and iron, and calcium, silica and the like.

However, porphyrazine can form a complex having an intended central metal atom, for example, a copper complex by a ionic bond or a coordination bond, so this central metal is not regarded as impurity.

As for the content of the above impurities, for example, each ion of heavy metals such as zinc and iron, and calcium, silica and the like are preferably 500 ppm or below respectively in a dried and purified product of the porphyrazine coloring matter, only as a guide.

The ion content of heavy metal and the like can be measured by an ion chromatography, the atomic absorption method or ICP (Inductively Coupled Plasma) emission spectrometry.

The ink of the present invention contains the porphyrazine coloring matter of the formula (1) in an amount of 0.1 to 8% by mass and preferably 0.3 to 6% by mass relative to the total amount of the ink.

This ink may further contain, according to necessity, a water-soluble organic solvent within such a range that the effect of the present invention is not inhibited. The water-soluble organic solvent is used for the purpose of action of dissolving a dye, preventing drying (moistening), modifying viscosity, promoting penetration, modifying surface tension, antifoaming and the like.

Besides this, further, the ink may also contain additives, for example, an antiseptic and fungicide, a pH adjuster, a chelating agent, a rust preventive agent, an ultraviolet absorbing agent, a viscosity modifier, a dye dissolving agent, an anti-fading agent, an emulsion stabilizer, a surface tension modifier, an antifoaming agent, a dispersing agent, a dispersion stabilizer and the like, as an ink preparation agent.

Said ink may preferably contain 0 to 60% by mass, preferably 10 to 50% by mass, of a water-soluble organic solvent and 0 to 20% by mass, preferably 0 to 15% by mass, of the above ink preparation agents, relative to the total amount of the ink. Besides this, optionally, the ink may also contain approximately 0 to 10% by mass of another optional component other than the above, for example, the porphyrazine coloring matter of the formula (1). The rest is water.

The above water-soluble organic solvent include, for example, C1 to C4 alkanols such as methanol, ethanol, n-propanol, isopropanol, n-butanol, isobutanol, secondary butanol and tertiary butanol; carboxylic acid amides such as N,N-dimethylformamide or N,N-dimethylacetoamide; heterocyclic ketones such as 2-pyrrolidone, N-methyl-2-pyrrolidone, 1,3-dimethylimidazolidin-2-one or 1,3-dimethylhexahydro-pyrimid-2-one; ketones or keto alcohols such as acetone, methyl ethyl ketone, 2-methyl-2-hydroxypentan-4-one; cyclic ethers such as tetrahydrofuran and dioxane; mono-, oligo- or polyalkylene glycols or thioglycols having a (C2 to C6) alkylene unit such as ethylene glycol, 1,2- or 1,3-propylene glycol, 1,2- or 1,4-butylene glycol, 1,6-hexylene glycol, diethylene glycol, triethylene glycol, tetraethylene glycol, dipropylene glycol, thiodiglycol, polyethylene glycol and poly propylene glycol; polyols (preferably, C3 to C6 triol) such as glycerine and hexane-1,2,6-triol; (C1 to C4) monoalkyl ethers of polyhydric alcohol such as ethylene glycol monomethyl ether, ethylene glycol monoethyl ether, diethylene glycol mono methyl ether, diethylene glycol monoethyl ether, diethylene glycol monobutyl ether (butyl carbitol), triethylene glycol monomethyl ether and triethylene glycol monoethyl ether; gamma-butyrolactone, dimethylsulfoxide, and the like.

The above water-soluble organic solvent is preferably isopropanol, glycerine, mono-, di- or tri-ethylene glycol, dipropylene glycol, 2-pyrrolidone or N-methyl-2-pyrrolidone, and more preferably isopropanol, glycerine, diethylene glycol, 2-pyrrolidone or butyl carbitol.

These are used alone or as a mixture thereof.

The antiseptic and fungicide include, for example, compounds of organic sulfur-based, organic nitrogen sulfur-based, organic halogen-based, haloallylsulfone-based, iodopropargyl-based, N-haloalkylthio-based, benzothiazole-based, nitril based, pyridine-based, 8-oxyquinoline-based, isothiazoline-based, dithiol-based, pyridineoxide-based, nitropropane-based, organic tin-based, phenol-based, quaternary ammonium salt-based, triazine-based, thiadiazine-based, anilide-based, adamantane-based, dithiocarbamate-based, brominated indanone-based, benzyl bromoacetate-based, inorganic salt-based and the like.

The organic halogen-based compound includes, for example, sodium pentachlorophenol, the pyridineoxide-based compound includes, for example, sodium 2-pyridinethiol-1-oxide, and the isothiazoline-based compound includes, for example, 1,2-benzisothiazolin-3-one, 2-n-octyl-4-isothiazolin-3-one, 5-chloro-2-methyl-4-isothiazolin-3-one, 5-chloro-2-methyl-4-isothiazolin-3-one magnesium chloride, 5-chloro-2-methyl-4-isothiazolin-3-one calcium chloride, 2-methyl-4-isothiazolin-3-one calcium chloride and the like.

Examples of the other antiseptic and fungicide include sodium sorbate, sodium benzoate, sodium acetate and the like (for example, trade name: Proxel GXL(S), Proxel XL-2(S) and the like; manufactured by Avecia Corp.).

As the pH adjuster, any substance can be used as long as it can control the pH of the ink in the range of 6.0 to 11.0 for the purpose of improving the storage stability of the ink. Examples thereof include alkanolamines such as diethanolamine and triethanolamine; alkali metal hydroxides such as lithium hydroxide, sodium hydroxide, potassium hydroxide; ammonium hydroxides; or alkali metal carbonates such as lithium carbonate, sodium carbonate and potassium carbonate.

The chelating agent includes, for example, sodium ethylenediaminetetraacetate, sodium nitrilotriacetate, sodium hydroxyethylethylenediaminetriacetate, sodium diethylenetriaminepentaacetate, sodium uracil diacetate and the like. The rust preventive agent includes, for example, hydrogen sulfite salt, sodium thiosulfate, ammonium thioglycolate, diisopropylammonium nitrite, pentaerythritol tetranitrate, dicyclohexylammonium nitrite and the like.

The ultraviolet absorbing agent includes, for example, benzophenone-based compounds, benzotriazole-based compounds, cinnamic acid-based compounds, triazine-based compounds, stilbene-based compounds or the like. In addition, a so-called fluorescent brightening agent which is a compound absorbing ultraviolet rays and emitting fluorescence typified by benzoxazole-based compounds can be used.

Examples of the viscosity modifier include, in addition to water-soluble organic solvents, water-soluble polymer compounds, for example, polyvinyl alcohols, cellulose derivatives, polyamines, polyimines and the like.

The dye dissolving agent includes, for example, urea, epsilon-caprolactam, ethylene carbonate and the like.

The antifading agent is used for the purpose of improving the storage stability of images. As the antifading agent, various organic and metal complex-based antifading agents can be used. Examples of the organic antifading agent are hydroquinones, alkoxyphenols, dialkoxyphenols, phenols, anilines, amines, indanes, chromans, alkoxyanilines, heterocycle compounds and the like, and examples of the metal complex-based antifading agent are nickel complex and zinc complex.

Examples of the surface tension modifier include surfactants, for example, anionic surfactants, amphoteric surfactants, cationic surfactants, nonionic surfactants and the like.

Examples of the anionic surfactant include alkylsulfocarboxylate, alpha-olefin sulfonate, polyoxyethylene alkyl ether acetate, N-acyl amino acid and salts thereof, N-acylmethyltaurine salt, alkylsulfate polyoxyalkyl ether sulfate, alkylsulfate polyoxyethylene alkyl ether phosphate, rosin acid soap, castor oil sulfate, lauryl alcohol sulfate, alkylphenol type phosphate ester, alkyl type phosphate ester, alkylallylsulfonate, diethylsulfosuccinate, diethylhexylsulfosuccinate, dioctylsulfosuccinate and the like.

Examples of the cationic surfactant are 2-vinylpyridine derivatives, poly(4-vinylpyridine) derivatives and the like.

Examples of the amphoteric surfactant are lauryldimethylaminoacetic acid betaine, 2-alkyl-N-carboxymethyl-N-hydroxyethyl imidazolinium betaine, coconut oil fatty acid amide propyldimethylaminoacetic acid betaine, polyoctylpolyaminoethylglycine, and in addition, imidazoline derivatives and the like.

Examples of the nonionic surfactant include ethers such as polyoxyethylene nonylphenyl ether, polyoxyethylene octylphenyl ether, polyoxyethylene dodecylphenyl ether, polyoxyethylene octylphenyl ether, polyoxyethylene oleyl ether, polyoxyethylene lauryl ether and polyoxyethylene alkyl ether, esters such as polyoxyethylene oleic acid, polyoxyethylene oleate ester, polyoxyethylene distearate ester, sorbitan laurate, sorbitan monostearate, sorbitan monooleate, sorbitan sesquioleate, polyoxyethylene monooleate and polyoxyethylene stearate, acetylene glycols such as 2,4,7,9-tetramethyl-5-decyne-4,7-diol, 3,6-dimethyl-4-octyne-3,6-diol, 3,5-dimethyl-1-hexyn-3 of (for example, Surfynol 104, 82 and 465, Olfine STG and the like, manufactured by Nissin Chemical Industry Co., Ltd.).

As the antifoaming agent, highly oxidized oil-based, glycerin fatty acid ester-based, fluorine-based and silicone-based compounds are used according to necessity.

These ink preparation agents are used alone or as a mixture thereof. In this connection, the surface tension of the ink of the present invention is usually 25 to 70 mN/m and more preferably 25 to 60 mN/m. In addition, the viscosity of the ink of the present invention is preferably 30 mPa·s or below. It is more preferable that it is further controlled at 20 mPa·s or below.

In producing the ink of the present invention, the order to dissolve each agent is particularly not limited. In preparation of the ink, water to be used is preferably water with less impurity, such as ion-exchanged water or distilled water. In addition, microfiltration using a membrane filter may be performed to remove foreign substances off according to necessity, and when the ink of the present invention is used as an ink for inkjet printer, it is preferable to perform microfiltration. The pore size of a filter to perform microfiltration with is usually 1 micron to 0.1 micron and preferably 0.8 micron to 0.2 micron.

The ink of the present invention can be used not only for monochrome image formation but also for full color image formation. In order to form full color images, it is also used for an ink set of 3 primary colors together with a magenta ink and a yellow ink, and further used for an ink set of 4 colors in which a black ink is added to this. In order to further form higher resolution images, it is used for an ink set in combination of a light magenta ink, a blue ink, a green ink, an orange ink, a dark yellow ink, a gray ink and the like.

As a coloring matter of the above yellow ink, various coloring matters can be used. Examples thereof are arylazo dyes or heteroarylazo dyes having phenols, naphtholes, anilines, heterocycles such as pyrazolone and pyridone, open-chain type active methylene compounds, and the like, as the coupling component (hereinafter, referred to as coupler component); methine dyes such as benzylidene dye and mono methine oxonol dye; quinone type dyes such as naphthoquinone dye and anthraquinone dye, and examples of the dye species other than these can include quinophthalone dyes, nitro-nitroso dyes, acridine dyes, acridinone dyes and the like.

As a coloring matter of the above magenta ink, various coloring matters can be used. Examples thereof include arylazo dyes or heteroazo dyes having, for example, phenols, naphtholes, anilines and the like, as a coupler component; azomethine dyes having, for example, a pyrazolones, a pyrazolotriazoles and the like, as a coupler component; methine dyes such as, for example, arylidene dye, styryl dye, merocyanine dye, cyanine dye and oxonol dye; carbonium dyes such as diphenyl methane dye, triphenylmethane dye and xanthene dye; quinone dyes such as, for example, naphthoquinone, anthraquinone and anthrapyridone; condensed polycyclic dyes such as, for example, dioxazine dye.

Examples of a coloring matter of the above black ink can include azo dyes such as disazo, trisazo or tetraazo, and in addition, dispersions of sulfur dye or carbon black.

The ink of the present invention can be used for recording methods such as impress printing, copying, marking, writing, drafting and stamping, and is particularly suitable for use in the inkjet recording method.

In the inkjet recording method of the present invention, recording is performed by filling the ink prepared in the above into an ink container and the like, providing energy to said ink to discharge ink drops and forming images on a known image receiving material (record-receiving material), for example, plain paper, resin coated paper, inkjet special paper, glossy paper, glossy film, electrophotography paper, fiber or cloth (cellulose, nylon, wool and the like), glass, metal, ceramics, leather and the like.

In forming images, a polymer particle dispersion (also referred to as polymeric latex) may be used for the purpose of imparting glossiness and water fastness and of improving weatherability.

Polymeric latex may be contained in an image receiving material or an ink, and otherwise may be applied, as another liquid, to the image receiving material before and after recording on the image receiving material. The timing to apply polymeric latex to an image receiving material may be before or after applying, or at the same time as applying colorant.

Therefore, according to the recording method of the present invention, recording may be performed on an image receiving material containing polymeric latex with the ink of the present invention, or recording may be performed on an image receiving material with the ink of the present invention containing polymeric latex.

The colored product of the present invention is a product colored with the porphyrazine coloring matter of the present invention or with an ink (water-based ink composition) or the like containing this. The materials to be colored therewith include, for example, communication sheets such as paper and film, fiber or cloth (cellulose, nylon, wool and the like), leather, substrates for color filters, and the like.

As the communication sheet, a communication sheet subjected to surface treatment, specifically provided with an ink receiving layer on the substrate of paper, synthetic paper, film and the like. Said ink receiving layer is provided by, for example, impregnating or coating a cation polymer on the above substrate, or by coating, on the above substrate surface, inorganic particles capable of absorbing the coloring matter in an ink such as porous silica, aluminasol and special ceramics together with a hydrophilic polymer such as polyvinyl alcohol and polyvinylpyrrolidone.

Such a communication sheet provided with an ink receiving layer is usually called inkjet special paper (film), glossy paper (film) and the like. Among these, it is inkjet special paper as a kind of paper on which inorganic particles capable of absorbing the coloring matter in an ink, such as porous silica, aluminasol and special ceramics are coated on the substrate surface, that is regarded as susceptible to the affection of gasses having oxidizing effect in the air such as ozone gas.

Typical examples of the above professional paper available as a commercial product include Pictorico® (manufactured by Asahi Glass Co., Ltd.), Professional Photopaper, Super Photopaper, Matte Photopaper (all manufactured by Canon Inc.), Photo Paper CRISPIA (highly glossy), Photo Paper (glossy), Photo Matte Paper (all manufactured by Seiko-Epson Corporation), Advanced Photo Paper (glossy) Premium Glossy Film, Photo Paper (all manufactured by Hewlett Packard Japan, Ltd.), PhotoLike® QP (manufactured by KONICA Corporation), High Quality Paper, Glossy Photo Paper (all manufactured by Sony Corporation), and the like. In addition, plain paper is naturally used.

As the coloring method to obtain the above colored product of the present invention, any methods may be used. One of the preferable coloring methods is a method using an inkjet printer to color the above materials with the ink of the present invention. The materials to be colored can be the above materials or other materials and not particularly limited as long as they are articles which can be colored by an inkjet printer.

In order to perform recording on the above materials or articles by the inkjet recording method of the present invention, for example, a container containing the above ink is put in a predetermined position of an inkjet printer and recording is performed on said materials or articles by an ordinary method.

The inkjet printer includes, for example, a piezo inkjet printer utilizing mechanical vibration; a bubble jet (registered trademark) printer utilizing bubbles generated by heating; and the like.

The ink according to the present invention is far from precipitation or separation during storage. In addition, when the ink according to the present invention is used for inkjet recording, it causes no clogging of an injector (inkhead). The ink according to the present invention has no change in its physical properties even when used for recording under constant recirculation for relatively long hours by a continuous ink jet printer or used for intermittent recording by an on-demand printer.

The ink of the present invention exhibits a vivid cyan color, and by using this ink, a recorded matter excellent particularly in ozone fastness, and also in light fastness and water fastness can be obtained.

By using the dark and light cyan inks respectively, and in addition, in combination with other inks of yellow and magenta and, according to necessity, green, red, orange, blue and the like which are excellent in ozone fastness, light fastness and water fastness, color tone having a broader visible region can be also expressed.

EXAMPLES

Hereinafter, the present invention will be more specifically explained with reference to the examples. In this connection, "part(s)" and "%" in the description are based on mass unless otherwise noted.

The term "(20% to the liquid)" described herein means that a compound is added in an amount of 20% by mass relative to the total liquid volume at a certain point.

Note that the compounds of the above formula (1) synthesized in the examples are all mixtures containing isomers and the like thereof as described above. Therefore, the chemical structural formula of a principal component or the chemical structural formula of one of them is described unless otherwise noted. In addition, the range of c of each compound synthesized in the examples is 0.5 to 1.0 unless otherwise noted. In connection, each yield also contains said isomers and the like.

Example 1

(1) Synthesis of a Mixture of Copper tribenzo(2,3-pyrido)porphyrazine and Copper dibenzobis(2,3-pyrido)porphyrazine (a Mixture in which 1.5 of A, B, C and D in the Following Formula (6) is a Pyridine Ring and the Rest 2.5 are Benzene Rings, on the Average)

Formula (6)

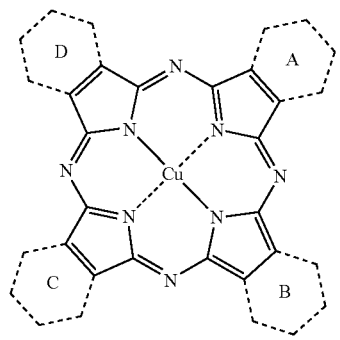

(6)

In a four-neck flask, 250 parts of sulfolane, 18.4 parts of phthalimide, 12.5 parts of quinolinic acid, 72.0 parts of urea, 8.8 parts of copper (II) chloride dihydrate (purity: 97.0%), 1.0 part of ammonium molybdate were added, the temperature was raised to 200° C. and the mixture was maintained at the same temperature for 5 hours. After completion of the reaction, the reaction liquid was cooled to 65° C., 200 parts of methanol was added thereto, and the precipitated crystals were filtered. The obtained crystals were washed with 150 parts of methanol and subsequently with 200 parts of hot water to obtain 72.2 parts of a wet cake. The whole volume of the obtained wet cake was added in 500 parts of 5% hydrochloric acid, the temperature was raised to 60° C. and the mixture was maintained at the same temperature for 1 hour. The crystals were filtered and washed with 200 parts of water. Then, the whole volume of the obtained wet cake was added into 500 parts of 10% ammonia water and maintained at 60° C. for 1 hour, and the crystals was filtered. The obtained crystals were washed with 300 parts of water and 100 parts of methanol to obtain 33.6 parts of a wet cake. The obtained wet cake was dried at 80° C. to obtain 19.8 parts of a mixture of copper tribenzo(2,3-pyrido)porphyrazine and copper dibenzobis(2,3-pyrido)porphyrazine as blue crystals.

λmax: 663.5 nm (in pyridine)

(2) Synthesis of a Mixture of Copper tribenzo(2,3-pyrido)porphyrazine Trisulfonyl Chloride and Copper dibenzobis(2,3-pyrido)porphyrazine Disulfonyl Chloride (a Mixture in which 1.5 of A, B, C and D is a Pyridine Ring and the Rest 2.5 are Benzene Ring, and n is 2.5 in the Following Formula (3))

Formula (3)

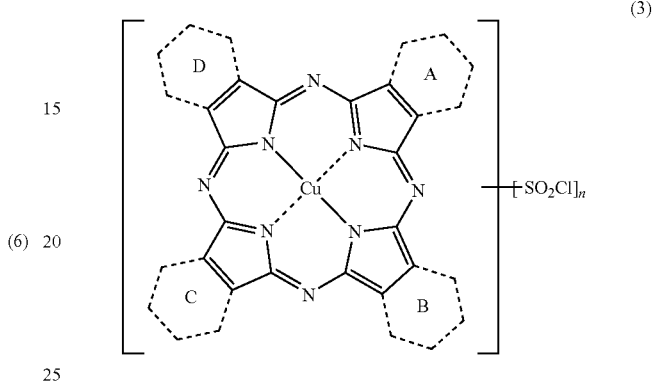

(3)

In 46.2 parts of chlorosulfonic acid, 5.8 parts of a mixture of copper tribenzo(2,3-pyrido)porphyrazine and copper dibenzobis(2,3-pyrido)porphyrazine obtained in Example 1-(1) was gradually added at 60° C. or below while stirring, and reacted at 140° C. for 4 hours. Next, the reaction liquid was cooled to 70° C., and 17.9 parts of thionyl chloride was added dropwise over 30 minutes and reacted at 70° C. for 3 hours. The reaction liquid was cooled to 30° C. or below and slowly poured into 800 parts of ice water, and the precipitated crystals were filtered and washed with 200 parts of cold water to obtain 40.0 parts of a wet cake of a mixture of copper tribenzo(2,3-pyrido)porphyrazine trisulfonyl chloride and copper dibenzobis(2,3-pyrido)porphyrazine disulfonyl chloride.

(3) Synthesis of the Following Formula (11) (a Compound in which X is 3,5-dicarboxyanilino, Y is 2-sulfoethylamino and E is Ethylene in the Formula (4))

Formula (11)

(11)

To 150 parts of ice water, 18.4 parts of cyanuric chloride and 0.2 parts of LEOCOL TD-90 (which is the trade name of a surfactant manufactured by Lion Corporation) were added, and stirred at 10° C. or below for 30 minutes. Next, 19.8 parts of 3,5-dicarboxyaniline (purity: 91.3%) was added thereto and reacted at 0 to 10° C. for 1 hour 30 minutes and at 20 to 25° C. for 1 hour 30 minutes while adjusting to pH 6.0 to 7.0 using a 10% aqueous sodium hydroxide solution. Next, to the obtained reaction liquid, 12.2 parts of 2-sulfoethylamine was added, and reacted at 30° C. for 2 hours while adjusting to pH 8.0 to 9.0 using a 10% aqueous sodium hydroxide solution. Then, 250 parts of ice was added thereto to cool to 0° C., and then 60 parts of ethylenediamine was added dropwise thereto while maintaining said liquid temperature at 5° C. or below. After that, the resulting liquid was stirred overnight at room temperature. The pH of the obtained reaction liquid was controlled at 2.0 using concentrated hydrochloric acid. In the meantime, the liquid was maintained at 10 to 15° C. while adding ice. At this time, the liquid volume was 1000 parts. To this reaction liquid, 200 parts of sodium chloride was added, and stirred for 30 minutes to precipitate crystals. The precipitated crystals were filtered to obtain 461 parts of a wet cake. The obtained wet cake was put into a beaker, 580 parts of water was added, and the pH was adjusted to pH 9.0 using a 10% aqueous sodium hydroxide solution, to dissolve the wet cake. At this time, the liquid volume was 1000 parts. To this reaction liquid, 200 parts of sodium chloride was added, the mixture was controlled at pH 4.5 using concentrated hydrochloric acid, and stirred for 30 minutes to precipitate crystals. The precipitated crystals were filtered to obtain 261 parts of a wet cake. The obtained wet cake was put into a beaker, and 470 parts of methanol and 47 parts of water were added and stirred at 50° C. for 1 hour, followed by filtration to obtain 104.8 parts of a wet cake. The obtained wet cake was dried to obtain 50.1 parts of white powder of a compound of the above formula (11).

(4) Synthesis of the Following Formula (12) (a Compound in which 1.5 of A, B, C and D is a Pyridine Ring, the Rest 2.5 are Benzene Rings, E is Ethylene, X is 3,5-dicarboxyanilino and Y is 2-sulfoethylamino in the Above Formula (1))

To 300 parts of ice water, 40.0 parts of a wet cake of a mixture of porphyrazine trisulfonyl chloride and copper dibenzobis(2,3-pyrido)porphyrazine disulfonyl chloride obtained in the above (2) of the present example were added, and suspended by stirring at 5° C. or below. Ten minutes later, in said suspension, a solution dissolving 13.2 parts of the compound of the above formula (11) in 2 parts of 28% ammonia water and 100 parts of water was added by pouring while maintaining said liquid temperature at 10° C. or below. In the meantime, 28% ammonia water was continuously added to maintain pH 9.0. With the same pH maintained, the liquid temperature was raised to 20° C. over 1 hour and the liquid was maintained at the same temperature for 8 hours. The liquid volume at this time was 650 parts. The temperature of the obtained reaction liquid was raised to 50° C., 130 parts of sodium chloride (20% to the liquid) was added thereto and stirred for 30 minutes, and then the pH of the liquid was controlled at 1.0 over 20 minutes. The precipitate was separated by filtration, washed with 100 parts of a 20% aqueous sodium chloride solution to obtain 156.0 parts of a wet cake. The obtained wet cake was dissolved in 550 parts of water by controlling the pH of said liquid at 9.5 with a 25% aqueous sodium hydroxide solution. The liquid volume at this time was 700 parts. The temperature of said dissolving liquid was raised to 60° C., 140 parts of sodium chloride (20% to the liquid) was added and stirred for 30 minutes, and then the pH of the liquid was controlled at 1.0 over 20 minutes. The precipitate was separated by filtration and washed with 100 parts of a 20% aqueous sodium chloride solution to obtain 91.2 parts of a wet cake of a compound represented by the above formula (12) as free acid. To the obtained wet cake, 600 parts of methanol and 60 parts of water were added, and stirred at 50° C. for 1 hour. Insoluble matter was separated by filtration to obtain 11.2 parts of a wet cake. The wet cake was dried to obtain 9.5 parts of a compound represented by the above formula (12) as blue powder.

λmax: 598.0 nm (in an aqueous solution)

Formula (12)

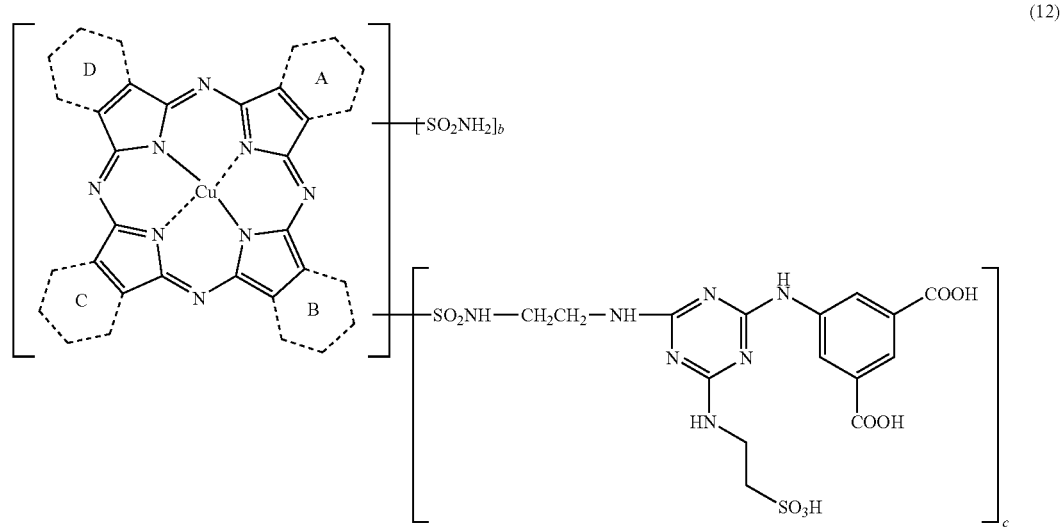

Example 2

(1) Synthesis of the Following Formula (13) (a Compound in which X is 3-sulfoanilino, Y is 2-sulfoethylamino and E is Ethylene in the Formula (4))

Formula (13)

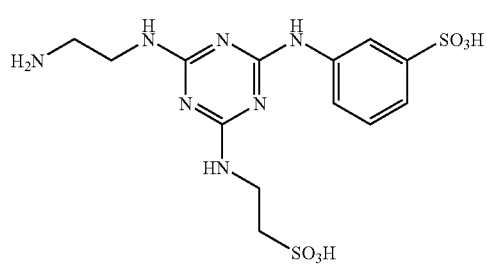

To 330 parts of ice water, 18.4 parts of cyanuric chloride and 0.2 parts of LEOCOL TD-90 (which is the trade name of a surfactant manufactured by Lion Corporation) were added, and stirred at 10° C. or below for 30 minutes. Next, 17.4 parts of 3-sulfoaniline (purity: 99.3%) was added to this and reacted at 0 to 10° C. for 1 hour 30 minutes and at 20 to 25° C. for 1 hour 30 minutes while adjusting to pH 2.0 to 2.5 using a 10% aqueous sodium hydroxide solution. Next, 12.2 parts of 2-sulfoethylamine was added to the reaction liquid and reacted:

(1) at pH 6.0 to 7.0 and 20° C. for 2 hours, (2) at pH 7.0 to 8.0 and 25° C. for 2 hours, and (3) at pH 8.0 to 9.0 and 25° C. for 2 hours, while adjusting the pH using a 10% aqueous sodium hydroxide solution.

Then, 250 parts of ice was added to the resulting reaction liquid to cool to 0° C., and then 60 parts of ethylenediamine was added dropwise while maintaining said liquid temperature at 5° C. or below. After that, said reaction liquid was stirred overnight at room temperature and then controlled at pH 1.0 using concentrated hydrochloric acid. During the control of the pH, the temperature of 10 to 15° C. was maintained while adding ice. At this time, the liquid volume was 1100 parts. To this reaction liquid, 250 parts of sodium chloride was added, and stirred for 30 minutes to precipitate crystals. The precipitated crystals were separated by filtration to obtain 110 parts of a wet cake. The obtained wet cake was put into a beaker, and 220 parts of water was added thereto and the pH was adjusted to pH 9.5 by using a 10% aqueous sodium hydroxide solution to dissolve the wet cake. At this time, the liquid volume was 500 parts. The pH of this reaction liquid was controlled at 1.0 using concentrated hydrochloric acid, and 100 parts of sodium chloride was added thereto and stirred for 30 minutes to precipitate crystals. The precipitated crystals were separated by filtration to obtain 120.1 parts of a wet cake. The obtained wet cake was put into a beaker, 220 parts of methanol and 24 parts of water were added and stirred at 50° C. for 1 hour, and then insoluble substance was separated by filtration to obtain 81.2 parts of a wet cake. The obtained wet cake was dried to obtain 47.1 parts of a compound of the above formula (13) as white powder.

(2) Synthesis of the Following Formula (14) (a Compound in which 1.5 of A, B, C and D is a Pyridine Ring, the Rest 2.5 are Benzene Rings, E is Ethylene, X is 3-Sulfoanilino and Y is 2-Sulfoethylamino in the Above Formula (1))

Formula (14)

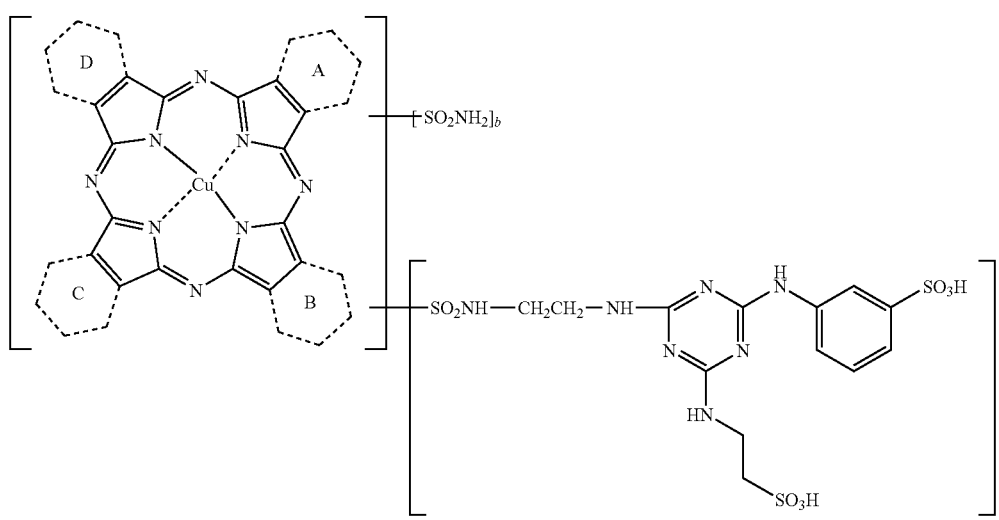

To 50 parts of ice water, 40.0 parts of a wet cake of a mixture of porphyrazine trisulfonyl chloride and copper dibenzobis(2,3-pyrido)porphyrazine disulfonyl chloride which were obtained in the same manner as in Example 1-(2) was added, and suspended by stirring at 5° C. or below. Ten minutes later, in said suspension, a solution dissolving 13.0 parts of the compound of the above formula (13) in 2 parts of 28% ammonia water and 100 parts of water was added by pouring while maintaining said liquid temperature at 10° C. or below. In the meantime, 28% ammonia water was continuously added to maintain pH 9.0. With the same pH maintained, the liquid temperature was raised to 20° C. over 1 hour and the liquid was maintained at the same temperature for 8 hours. The liquid volume at this time was 650 parts. The temperature of the reaction liquid was raised to 50° C., and 130 parts of sodium chloride (20% to the liquid) was added thereto and stirred for 30 minutes. Then, after the pH of the liquid was controlled at 1.0 over 20 minutes, the precipitate was separated by filtration and washed with 100 parts of a 20% aqueous sodium chloride solution to obtain 46.0 parts of a wet cake. The obtained wet cake was dissolved in 280 parts of water by controlling the pH at 9.0 using a 25% aqueous sodium hydroxide solution. The liquid volume at this time was 300 parts. The temperature of the dissolving liquid was raised to 50° C., and 60 parts of sodium chloride (20% to the liquid) was added thereto and stirred for 30 minutes. Then, after the pH of the liquid was controlled at 1.0 over 20 minutes, the precipitate was separated by filtration and washed with 100 parts of a 20% aqueous sodium chloride solution to obtain 43.2 parts of a wet cake of a compound represented by the following formula (14) as free acid. To the obtained wet cake, 280 parts of methanol and 28 parts of water were added, and stirred at 50° C. for 1 hour. Insoluble matter was separated by filtration to obtain 11.2 parts of a wet cake. This was dried to obtain 9.2 parts of a compound represented by the above formula (14) as blue powder.

λmax: 606.0 nm (in an aqueous solution)

Example 3

(1) Synthesis of the Following Formula (15) (a Compound in which X is 4-sulfoanilino, Y is 2-sulfoethylamino and E is Ethylene in the Formula (4))

Formula (15)

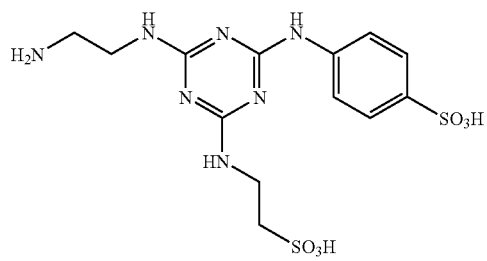

(15)

lamine was added to the resulting reaction liquid and reacted at 25° C. for 2 hours while adjusting to pH 7.0 to 8.0 using a 10% aqueous sodium hydroxide solution. Then, 250 parts of ice was added to this reaction liquid to cool to 0° C., and 60 parts of ethylenediamine was added dropwise thereto while maintaining the temperature of said reaction liquid at 5° C. or below. After that, the resulting liquid was stirred overnight at room temperature, and then the pH of said liquid was controlled at 1.0 using concentrated hydrochloric acid. During the control of the pH, the liquid temperature was maintained at 10 to 15° C. while adding ice. At this time, the liquid volume was 980 parts. To this reaction liquid, 190 parts of sodium chloride was added, and stirred for 30 minutes to precipitate crystals. The precipitated crystals were separated by filtration to obtain 70.6 parts of a wet cake. The obtained wet cake was put into a beaker, 280 parts of water was added, and the pH of the resulting suspension was adjusted to 9.0 using a 10% aqueous sodium hydroxide solution, to dissolve the wet cake. At this time, the liquid volume was 400 parts. To this reaction liquid, concentrated hydrochloric acid was added to control the pH at 1.0, and then 80 parts of sodium chloride was added and stirred for 30 minutes to precipitate crystals. The precipitated crystals were separated by filtration to obtain 110.1 parts of a wet cake. The obtained wet cake was put into a beaker, 260 parts of methanol and 26 parts of water were added thereto and stirred at 50° C. for 1 hour, and then insoluble matter was separated by filtration to obtain 89.1 parts of a wet cake. The obtained wet cake was dried to obtain 49.3 parts of a compound of the above formula (15) as white powder.

(2) Synthesis of the Following Formula (16) (a Compound in which 1.5 of A, B, C and D is a Pyridine Ring, the Rest 2.5 were Benzene Ring, E is Ethylene, X is 4-Sulfoanilino and Y is 2-Sulfoethylamino in the Above Formula (1))

Formula (16)

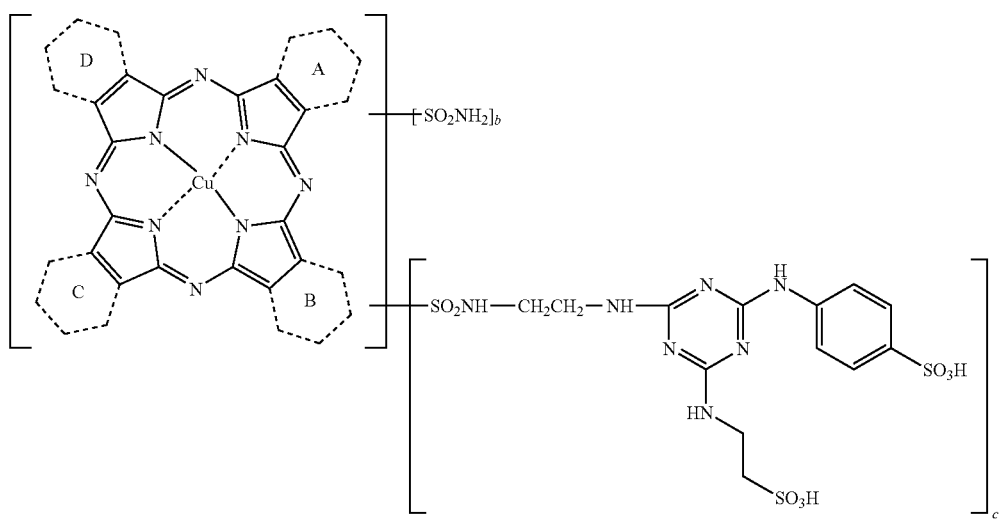

(16)

To 330 parts of ice water, 18.4 parts of cyanuric chloride and 0.2 parts of LEOCOL TD-90 (which is the trade name of a surfactant manufactured by Lion Corporation) were added, and stirred at 10° C. or below for 30 minutes. Next, 17.4 parts of 4-sulfoaniline (purity: 99.3%) was added to this and reacted at pH 2.6 to 3.0 and 0 to 5° C. for 1 hour, at pH 3.0 to 3.5 and 0 to 5° C. for 1 hour and at pH 3.0 to 3.5 and 25 to 30° C. for 1 hour while adjusting the pH using a 10% aqueous sodium hydroxide solution. Next, 12.6 parts of 2-sulfoethy- To 50 parts of ice water, 40.0 parts of a wet cake of a mixture of porphyrazine trisulfonyl chloride and copper dibenzobis(2,3-pyrido)porphyrazine disulfonyl chloride obtained in the same manner as in Example 1-(2) was added, and suspended by stirring at 5° C. or below. Ten minutes later, in said suspension, a solution dissolving 13.0 parts of the compound of the above formula (15) in 2 parts of 28% ammonia water and 100 parts of water was added by pouring while maintaining said liquid temperature at 10° C. or below. In the meantime, 28% ammonia water was continuously added to maintain pH 9.0. With the same pH maintained, the liquid temperature was raised to 20° C. over 1 hour and the liquid was maintained at the same temperature for 8 hours. The liquid volume at this time was 680 parts. The temperature of the reaction liquid was raised to 50° C., 136 parts of sodium chloride (20% to the liquid) was added thereto and stirred for 30 minutes, and then the pH of said liquid was controlled at 1.0 over 20 minutes. The precipitate was separated by filtration and washed with 100 parts of a 20% aqueous sodium chloride solution to obtain 45.0 parts of a wet cake. To the obtained wet cake, 360 parts of water was added, and the wet cake was dissolved by controlling the pH of the resulting suspension at 9.0 with a 25% aqueous sodium hydroxide solution. The liquid volume at this time was 400 parts. The temperature of the dissolving liquid was raised to 50° C., 80 parts of sodium chloride (20% to the liquid) was added thereto and stirred for 30 minutes, and then the pH of the resulting liquid was controlled at 1.0 over 20 minutes. Insoluble matter was separated by filtration and washed with 100 parts of a 20% aqueous sodium chloride solution to obtain 43.2 parts of a wet cake of a compound represented by the above formula (16) as free acid. After 360 parts of methanol and 36 parts of water were added to the obtained wet cake and stirred at 50° C. for 1 hour, insoluble matter was separated by filtration to obtain 24.4 parts of a wet cake. The wet cake was dried to obtain 9.9 parts of a compound represented by the above formula (16) as blue powder.

λmax: 605.5 nm (in an aqueous solution)

Example 4

(1) Synthesis of the Following Formula (17) (a Compound in which X is a 4-sulfoanilino Group, Y is bis(2-carboxyethyl)amino and E is Ethylene in the Formula (4))

Formula (17)

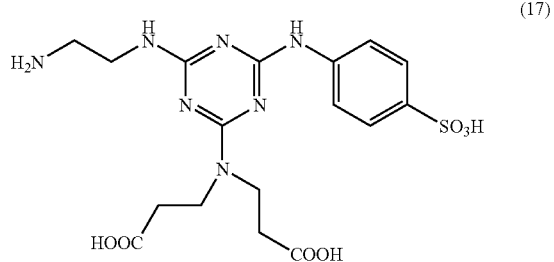

(17)

To 330 parts of ice water, 18.4 parts of cyanuric chloride and 0.2 parts of LEOCOL TD-90 (which is the trade name of a surfactant manufactured by Lion Corporation) were added, and stirred at 10° C. or below for 30 minutes. Next, 17.4 parts of 4-sulfoaniline (purity: 99.3%) was added thereto and reacted at pH 2.6 to 3.0 and 0 to 5° C. for 1 hour, at pH 3.0 to 3.5 and 0 to 5° C. for 1 hour, and at pH 3.0 to 3.5 and 25 to 30° C. for 1 hour while adjusting the pH using a 10% aqueous sodium hydroxide solution. Next, 13.7 parts of bis(2-carboxyethyl) amine was added to the reaction liquid and reacted at 25° C. for 2 hours while adjusting to pH 7.0 to 8.0 using a 10% aqueous sodium hydroxide solution. Then, 250 parts of ice was added thereto to cool to 0° C. While maintaining said liquid temperature at 5° C. or below, 60 parts of ethylenediamine was added dropwise thereto. After that, the mixture was stirred overnight at room temperature, and then controlled at pH 1.0 using concentrated hydrochloric acid. During the control of the pH, the temperature of 10 to 15° C. was maintained while adding ice. At this time, the liquid volume was 1500 parts. To this reaction liquid, 300 parts of sodium chloride was added, and stirred for 1 hour 30 minutes to precipitate crystals. The precipitated crystals were filtered to obtain 60.0 parts of a wet cake. The obtained wet cake was put into a beaker, 240 parts of water was added, and the pH of the resulting suspension was adjusted to 9.8 using a 10% aqueous sodium hydroxide solution, to dissolve the wet cake. At this time, the liquid volume was 300 parts. To this reaction liquid, concentrated hydrochloric acid was added to control at pH 1.0. Thereto, 60 parts of sodium chloride was added, and stirred for 30 minutes to precipitate crystals. The precipitated crystals were filtered to obtain 40.1 parts of a wet cake. The obtained wet cake was put into a beaker, 240 parts of methanol and 24 parts of water were added and stirred at 50° C. for 1 hour, followed by filtration to obtain 37.1 parts of a wet cake. The obtained wet cake was dried to obtain 34.2 parts of a compound of the above formula (17) as white powder.

(2) Synthesis of the Following Formula (18) (a Compound in which 1.5 of A, B, C and D is a Pyridine Ring and the Rest 2.5 are Benzene Rings, E is Ethylene, X is 4-sulfoanilino and Y is bis(2-carboxyethyl) amino in the Above Formula (1))

Formula (18)

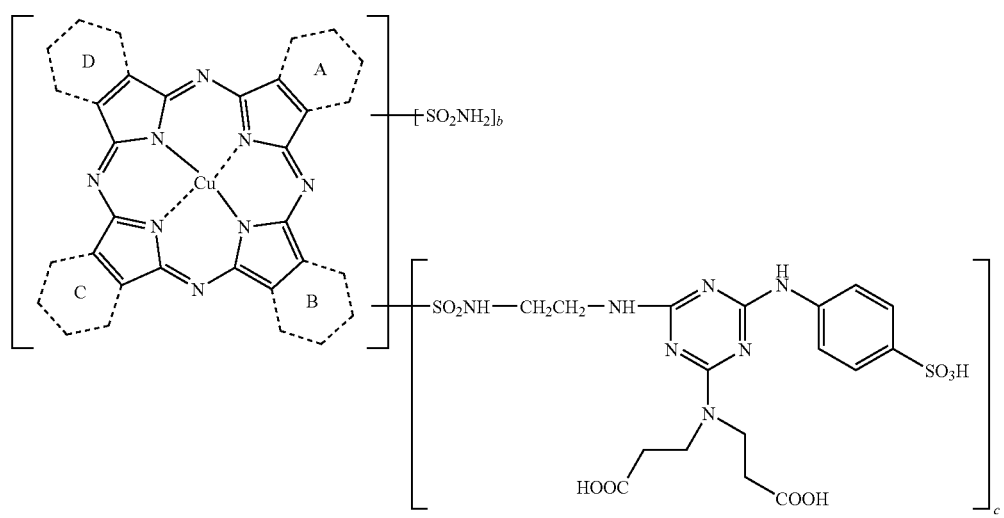

(18)

To 50 parts of ice water, 40.0 parts of a wet cake of a mixture of porphyrazine trisulfonyl chloride and copper dibenzobis(2,3-pyrido)porphyrazine disulfonyl chloride obtained in the same manner as in Example 1-(2) was added, and suspended by stirring at 5° C. or below. Ten minutes later, in said suspension, a solution dissolving 14.3 parts of the compound of the above formula (17) in 2 parts of 28% ammonia water and 100 parts of water was added by pouring while maintaining said liquid temperature at 10° C. or below. In the meantime, 28% ammonia water was continuously added to maintain pH 9.0. With the same pH maintained, the temperature of said liquid was raised to 20° C. over 1 hour and the liquid was maintained at the same temperature for 8 hours. The liquid volume at this time was 600 parts. The temperature of the reaction liquid was raised to 50° C., 120 parts of sodium chloride (20% to the liquid) was added and stirred for 30 minutes, and then the pH of the liquid was controlled at 1.0 over 20 minutes. The precipitated crystals were separated by filtration and washed with 100 parts of a 20% aqueous sodium chloride solution to obtain 182.0 parts of a wet cake. To the obtained wet cake, 400 parts of water was added, and the pH of the resulting suspension was controlled at 9.0 using a 25% aqueous sodium hydroxide solution, to dissolve the wet cake. The liquid volume at this time was 600 parts. The temperature of the dissolving liquid was raised to 50° C., and 120 parts of sodium chloride (20% to the liquid) was added and stirred for 30 minutes. After the pH of said liquid was controlled at 1.0 over 20 minutes, the precipitated crystals were separated by filtration and washed with 100 parts of a 20% aqueous sodium chloride solution to obtain 84.3 parts of a wet cake. To the obtained wet cake, 700 parts of methanol and 70 parts of water were added, and stirred at 50° C. for 1 hour, followed by filtration to obtain 10.9 parts of a wet cake. The wet cake was dried to obtain 9.2 parts of a compound represented by the above formula (18) of the free acid as blue powder.

λmax: 593.0 nm (in an aqueous solution)

Example 5

(1) Synthesis of the Following Formula (19) (a Compound in which X is 4-sulfoanilino, Y is 2-hydroxyethylamino and E is Ethylene in the Formula (4))

Formula (19)

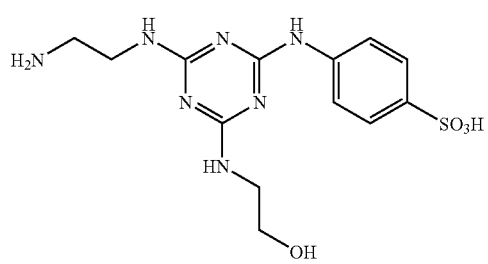

(19)

To 330 parts of ice water, 18.4 parts of cyanuric chloride and 0.2 parts of LEOCOL TD-90 (which is the trade name of a surfactant manufactured by Lion Corporation) were added, and stirred at 10° C. or below for 30 minutes. Next, 17.4 parts of 4-sulfoaniline (purity: 99.3%) was added and reacted at pH 2.6 to 3.0 and 0 to 5° C. for 1 hour, at pH 3.0 to 3.5 and 0 to 5° C. for 1 hour and at pH 3.0 to 3.5 and 25 to 30° C. for 1 hour while controlling the pH using a 10% aqueous sodium hydroxide solution. Next, 6.17 parts of 2-hydroxyethylamine was added to the reaction liquid and reacted at 25° C. for 3 hours 30 minutes while adjusting to pH 8.0 to 9.0 using a 10% aqueous sodium hydroxide solution. Then, 210 parts of ice was added thereto to cool to 0° C. While maintaining said liquid temperature at 5° C. or below, 60 parts of ethylenediamine was added dropwise to said liquid. After that, the liquid was stirred overnight at room temperature, and then the pH was controlled at 1.0 using concentrated hydrochloric acid. During the control of the pH, the temperature of 10 to 15° C. was maintained while adding ice. At this time, the liquid volume was 1000 parts. To this reaction liquid, 200 parts of sodium chloride was added, and stirred for 30 minutes to precipitate crystals. The precipitated crystals were filtered to obtain 257 parts of a wet cake. The obtained wet cake was put into a beaker and 580 parts of water was added. The pH of the resulting suspension was controlled at 9.0 using a 10% aqueous sodium hydroxide solution, to dissolve the wet cake. At this time, the liquid volume was 850 parts. To this reaction liquid, concentrated hydrochloric acid was added to control the pH at 1.0. Thereto, 170 parts of sodium chloride was added, and stirred for 30 minutes to precipitate crystals. The precipitated crystals were filtered to obtain 212.1 parts of a wet cake. The obtained wet cake was put into a beaker, and 560 parts of methanol and 56 parts of water were added and stirred at 50° C. for 1 hour. The mixture was filtered to obtain 48.1 parts of a wet cake. The obtained wet cake was dried to obtain 28.2 parts of a compound of the above formula (19) as white powder.

(2) Synthesis of the Following Formula (20) (a Compound in which 1.5 of A, B, C and D is a Pyridine Ring, the Rest 2.5 are Benzene Rings, E is Ethylene, X is 4-Sulfoanilino and Y is 2-hydroxyethylamino in the Above Formula (1))

Formula (20)

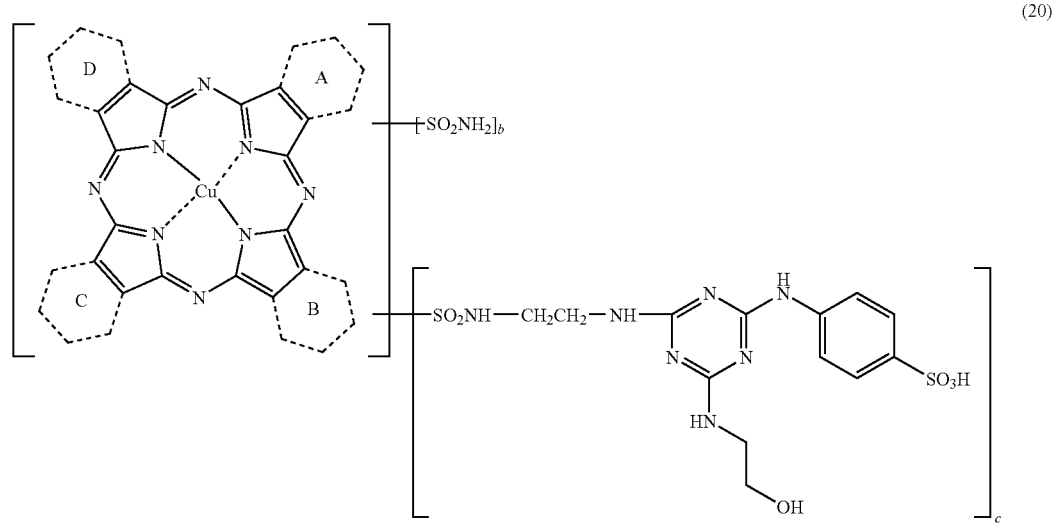

To 50 parts of ice water, 40.0 parts of a wet cake of a mixture of porphyrazine trisulfonyl chloride and copper dibenzobis(2,3-pyrido) porphyrazine disulfonyl chloride obtained in the same manner as in Example 1-(2) was added, and suspended by stirring at 5° C. or below. Ten minutes later, in said suspension, a solution dissolving 11.1 parts of the compound of the above formula (19) in 2 parts of 28% ammonia water and 100 parts of water was added by pouring while maintaining said liquid temperature at 10° C. or below. In the meantime, 28% ammonia water was continuously added to maintain pH 9.0. With the same pH maintained, the liquid temperature was raised to 20° C. over 1 hour and the liquid was maintained at the same temperature for 8 hours. The liquid volume at this time was 700 parts. The temperature of the reaction liquid was raised to 50° C., 140 parts of sodium chloride (20% to the liquid) was added and stirred for 30 minutes, and then the pH was controlled at 1.0 over 20 minutes. The precipitated crystals were separated by filtration and washed with 100 parts of a 20% aqueous sodium chloride solution to obtain 213.0 parts of a wet cake. To the obtained wet cake, 380 parts of water was added, and the pH of the resulting suspension was controlled at 9.0 using a 25% aqueous sodium hydroxide solution, to dissolve the wet cake. The liquid volume at this time was 600 parts. The temperature of the dissolving liquid was raised to 50° C., 120 parts of sodium chloride (20% to the liquid) was added and stirred for 30 minutes, and then the pH of the liquid was controlled at 1.0 over 20 minutes. The precipitated crystals were separated by filtration and washed with 100 parts of a 20% aqueous sodium chloride solution to obtain 55.8 parts of a wet cake. To the obtained wet cake, 360 parts of methanol and 36 parts of water were added, and stirred at 50° C. for 1 hour, followed by filtration to obtain 34.2 parts of a wet cake. The wet cake was dried to obtain 11.6 parts of a compound represented by the above formula (20) of the free acid as blue powder.

Example 6

(1) Synthesis of the Following Formula (21) (a Compound in which X is 6-sulfo-1-naphthylamino, Y is 2-sulfoethylamino and E is Ethylene in the Formula (4))

Formula (21)

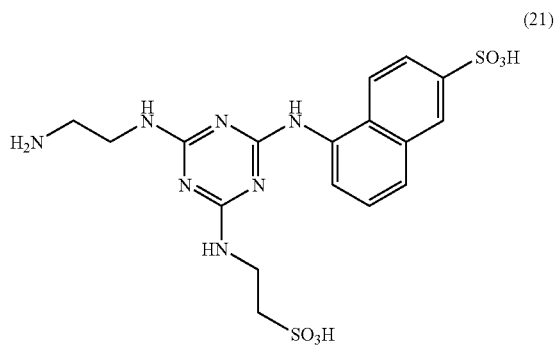

To 330 parts of ice water, 18.4 parts of cyanuric chloride and 0.2 parts of LEOCOL TD-90 (which is the trade name of a surfactant manufactured by Lion Corporation) were added, and stirred at 10° C. or below for 30 minutes. Next, 42.0 parts of 6-sulfo-1-naphthylamine (purity: 55.3%) was added thereto and reacted at 0 to 5° C. for 1 hour and at 25 to 30° C. for 1 hour while controlling at pH 5.5 to 6.0 using a 10% aqueous sodium hydroxide solution. Next, 12.5 parts of 2-sulfoethylamine was added to the reaction liquid and reacted at 45° C. for 30 minutes and at 50 to 55° C. for 1 hour while controlling at pH 8.0 to 9.0 using a 10% aqueous sodium hydroxide solution. Then, 570 parts of ice was added to said reaction liquid to cool to 0° C. Thereto, 60 parts of ethylenediamine was added dropwise while maintaining said liquid temperature at 5° C. or below. After that, the liquid was stirred overnight at room temperature, and then the pH of the resulting liquid was controlled at 1.0 using concentrated hydrochloric acid. During the control of the pH, the liquid temperature was maintained at 10 to 15° C. while adding ice. At this time, the liquid volume was 1750 parts. To this reaction liquid, 350 parts of sodium chloride was added, and stirred for 30 minutes to precipitate crystals. The precipitated crystals were filtered to obtain 40.0 parts of a wet cake. The obtained wet cake was put into a beaker, 800 parts of water was added, and the pH of the resulting suspension was adjusted to 9.0 using a 10% aqueous sodium hydroxide solution. At this time, the liquid volume was 900 parts. To this reaction liquid, concentrated hydrochloric acid was added to control at pH 1.0, and then 180 parts of sodium chloride was added and stirred for 30 minutes to precipitate crystals. The precipitated crystals were filtered to obtain 40.2 parts of a wet cake. The obtained wet cake was put into a beaker, and 300 parts of methanol and 30 parts of water were added and stirred at 50° C. for 1 hour, followed by filtration to obtain 36.2 parts of a wet cake. The obtained wet cake was dried to obtain 18.9 parts of a compound of the above formula (21) as white powder.

(2) Synthesis of the Following Formula (22) (a Compound in which 1.5 of A, B, C and D is a Pyridine Ring, the Rest 2.5 are Benzene Rings, E is Ethylene, X is 6-sulfo-1-naphthylamino and Y is 2-sulfoethylamino in the Above Formula (1))

To 50 parts of ice water, 40.0 parts of a wet cake of a mixture of porphyrazine trisulfonyl chloride and copper dibenzobis(2,3-pyrido) porphyrazine disulfonyl chloride obtained in the same manner as in Example 1-(2) was added, and suspended by stirring at 5° C. or below. Ten minutes later, in said suspension, a solution dissolving 14.5 parts of the compound of the above formula (21) in 2 parts of 28% ammonia water and 100 parts of water was added by pouring while maintaining said liquid temperature at 10° C. or below. In the meantime, 28% ammonia water was continuously added to maintain pH 9.0. With the same pH maintained, the temperature of said liquid was raised to 20° C. over 1 hour and the liquid maintained at the same temperature for 8 hours. The liquid volume at this time was 700 parts. The temperature of the resulting reaction liquid was raised to 50° C., and 140 parts of sodium chloride (20% to the liquid) was added thereto and stirred for 30 minutes. After the pH of said liquid was controlled at 1.0 over 20 minutes, the precipitated crystals were separated by filtration and washed with 100 parts of a 20% aqueous sodium chloride solution to obtain 94.0 parts of a wet cake. To the obtained wet cake, 370 parts of water was added, and the pH of the resulting suspension was controlled at 10.0 using a 25% aqueous sodium hydroxide solution, to dissolve a wet cake. The liquid volume at this time was 450 parts. The temperature of the dissolving liquid was raised to 50° C. and 90 parts of sodium chloride (20% to the liquid) was added and stirred for 30 minutes. After the pH of said liquid was controlled at 1.0 over 20 minutes, the precipitated crystals were separated by filtration and washed with 100 parts of a 20% aqueous sodium chloride solution to obtain 92.2 parts of a wet cake. To the obtained wet cake, 300 parts of methanol and 50 parts of water were added, and stirred at 50° C. for 1 hour, followed by filtration to obtain 76.2 parts of a wet cake.

Formula (22)

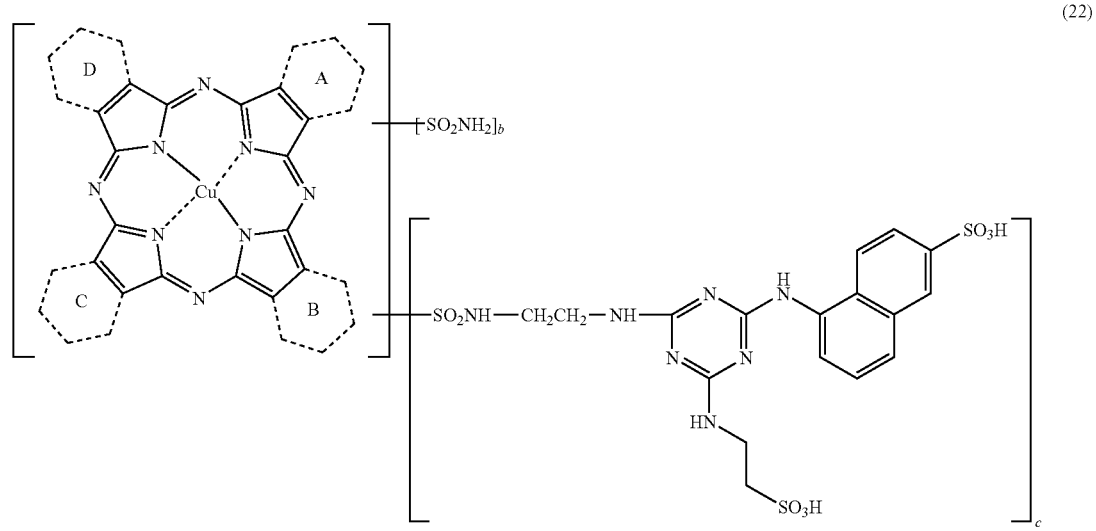

(22)

The wet cake was dried to obtain 23.2 parts of a compound represented by the above formula (22) as the free acid as blue powder.

Example 7

(1) Synthesis of the Following Formula (23) (a Compound in which X is 3,8-disulfo-1-naphthylamino, Y is Amino and E is Ethylene in the Formula (4))

Formula (23)

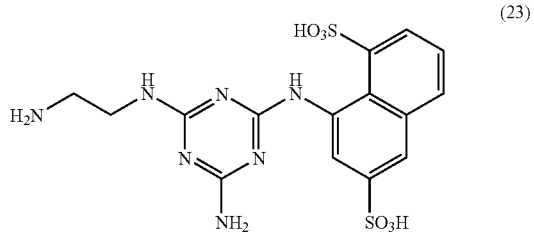

(2) Synthesis of the Following Formula (24) (a Compound in which 1.5 of A, B, C and D is a Pyridine Ring, the Rest 2.5 are Benzene Rings, E is Ethylene, X is 3,8-disulfo-1-naphthylamino and Y is Amino in the Above Formula (1))

Formula (24)

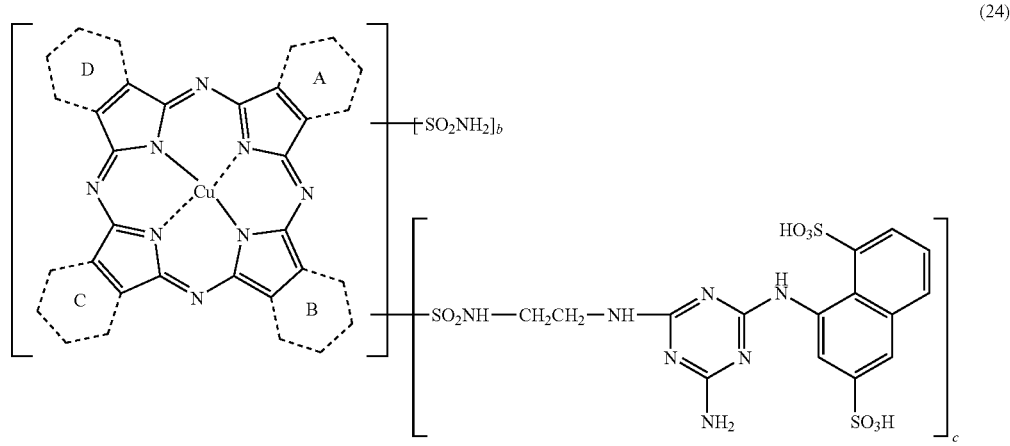

To 330 parts of ice water, 18.4 parts of cyanuric chloride and 0.2 parts of LEOCOL TD-90 (which is the trade name of a surfactant manufactured by Lion Corporation) were added, and stirred at 10° C. or below for 30 minutes. Next, 38.3 parts of 3,8-disulfo-1-naphthylamine (purity: 80.0%) was added and reacted at 0 to 5° C. for 1 hour and at 25 to 30° C. for 2 hours while adjusting the pH to 3.0 to 4.0 using a 10% aqueous sodium hydroxide solution. Next, 5.61 parts of ammonium chloride was added to the reaction liquid and reacted at pH 7.0 to 8.0 and 20° C. for 2 hours 30 minutes and at pH 9.0 and 20° C. for 2 hours while adjusting the pH using a 10% aqueous sodium hydroxide solution. Then, 200 parts of ice was added thereto to cool to 0° C., and then 60 parts of ethylenediamine was added dropwise thereto while maintaining said liquid temperature at 5° C. or below. After that, the liquid was stirred overnight at room temperature, and then the pH of the resulting reaction liquid was controlled at 1.0 using concentrated hydrochloric acid. During the control of the pH, the temperature of 10 to 15° C. was maintained while adding ice to said reaction liquid. At this time, the liquid volume was 1750 parts. To this reaction liquid, 350 parts of sodium chloride was added, and stirred for 30 minutes to precipitate crystals. The precipitated crystals were filtered to obtain 72.6 parts of a wet cake. The obtained wet cake was put into a beaker, 700 parts of water was added, and the pH of the resulting suspension was adjusted to 9.0 using a 10% aqueous sodium hydroxide solution. At this time, the liquid volume was 830 parts. To this reaction liquid, concentrated hydrochloric acid was added to control at pH 1.0, and then 166 parts of sodium chloride was added and stirred for 30 minutes to precipitate crystals. The precipitated crystals were filtered to obtain 60.1 parts of a wet cake. The obtained wet cake was put into a beaker, and 300 parts of methanol and 30 parts of water were added and stirred at 50° C. for 1 hour, followed by filtration to obtain 55.6 parts of a wet cake. The obtained wet cake was dried to obtain 44.3 parts of a compound of the above formula (23) as white powder.

To 50 parts of ice water, 40.0 parts of a wet cake of a mixture of porphyrazine trisulfonyl chloride and copper dibenzobis(2,3-pyrido) porphyrazine disulfonyl chloride obtained in the same manner as in Example 1-(2) was added, and suspended by stirring at 5° C. or below. Ten minutes later, in said suspension, a solution dissolving 13.6 parts of the compound of the formula (23) in 2 parts of 28% ammonia water and 100 parts of water was added by pouring while maintaining said liquid temperature at 10° C. or below. In the meantime, 28% ammonia water was continuously added to maintain pH 9.0. With the same pH maintained, the liquid temperature was raised to 20° C. over 1 hour and the liquid was maintained at the same temperature for 8 hours. The liquid volume at this time was 600 parts. The temperature of the reaction liquid was raised to 50° C., 120 parts of sodium chloride (20% to the liquid) was added and stirred for 30 minutes, and then the pH of the liquid was controlled at 1.0 over 20 minutes. The precipitated crystals were separated by filtration and washed with 100 parts of a 20% aqueous sodium chloride solution to obtain 62.4 parts of a wet cake. To the obtained wet cake, 330 parts of water was added, and the pH of the resulting suspension was controlled at 9.0 using a 25% aqueous sodium hydroxide solution, to dissolve the wet cake. The liquid volume at this time was 400 parts. The temperature of the dissolving liquid was raised to 50° C., 80 parts of sodium chloride (20% to the liquid) was added and stirred for 30 minutes, and then the pH of the liquid was controlled at 1.0 over 20 minutes. The precipitated crystals were separated by filtration and washed with 100 parts of a 20% aqueous sodium chloride solution to obtain 59.2 parts of a wet cake. To the obtained wet cake, 600 parts of methanol and 60 parts of water were added, and stirred at 50° C. for 1 hour, followed by filtration to obtain 30.5 parts of a wet cake. The wet cake was dried to obtain 10.7 parts of a compound represented by the above formula (24) of the free acid as blue powder.

Example 8

(1) Synthesis of the Following Formula (25) (a Compound in which X is 3,6-disulfo-1-naphthylamino, Y is 2-hydroxyethoxyethylamino and E is Ethylene in the Formula (4))

Formula (25)

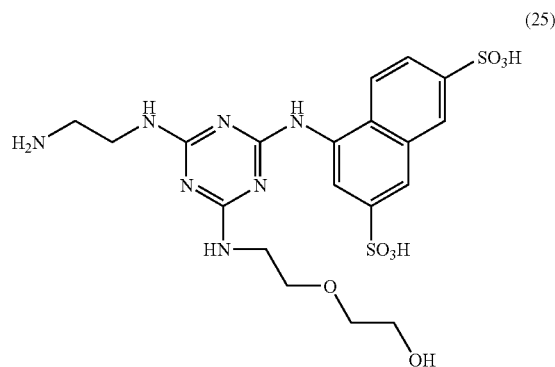

(25)

To 330 parts of ice water, 18.4 parts of cyanuric chloride and 0.2 parts of LEOCOL TD-90 (which is the trade name of a surfactant manufactured by Lion Corporation) were added and stirred at 10° C. or below for 30 minutes. Next, 38.3 parts of 3,6-disulfo-1-naphthylamine (purity: 80.0%) was added and reacted at 0 to 5° C. for 1 hour and at 25 to 30° C. for 2 hours while adjusting to pH 2.0 to 3.0 using a 10% aqueous sodium hydroxide solution. Next, 10.6 parts of aminoethoxyethanol was added to the reaction liquid, and reacted at pH 8.0 to 9.0 and 25° C. for 1 hour and at pH 7.5 to 8.0 and 25° C. for 30 minutes while adjusting the pH using a 10% aqueous sodium hydroxide solution. Then, 270 parts of ice was added to cool to 0° C. and 60 parts of ethylenediamine was added dropwise to said reaction liquid while maintaining said liquid temperature at 5° C. or below. After that, the liquid was stirred overnight at room temperature. At this time, the liquid volume was 1250 parts. To this reaction liquid, 250 parts of sodium chloride was added, and stirred for 30 minutes to precipitate crystals. The precipitated crystals were filtered to obtain 258.2 parts of a wet cake. The obtained wet cake was put into a beaker, 450 parts of water was added, and the pH was adjusted to pH 5.0 using a 10% aqueous sodium hydroxide solution. At this time, the liquid volume was 700 parts. To this reaction liquid, concentrated hydrochloric acid was added to control to pH 1.0, and 140 parts of sodium chloride was added and stirred for 30 minutes to precipitate crystals. The precipitated crystals were filtered to obtain 212.2 parts of a wet cake. The obtained wet cake was put into a beaker, and 1250 parts of methanol and 125 parts of water were added and stirred at 50° C. for 1 hour, followed by filtration to 90.8 parts of a wet cake. The obtained wet cake was dried to obtain 31.2 parts of a compound of the above formula (25) as white powder.

(2) Synthesis of the Following Formula (26) (a Compound in which 1.5 of A, B, C and D is a Pyridine Ring, the Rest 2.5 are Benzene Rings, E is Ethylene, X is 3,6-disulfo-1-naphthylamino and Y is 2-hydroxyethoxyethylamino in the Above Formula (1))

Formula (26)

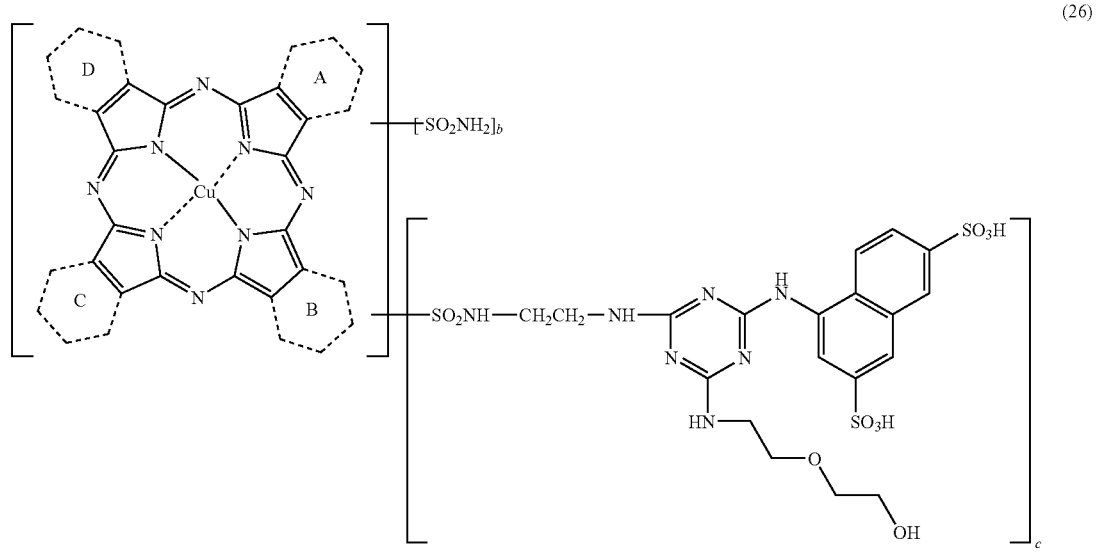

(26)

To 50 parts of ice water, 40.0 parts of a wet cake of a mixture of porphyrazine trisulfonyl chloride and copper dibenzobis(2,3-pyrido)porphyrazine disulfonyl chloride obtained in the same manner as in Example 1-(2) was added, and suspended by stirring at 5° C. or below. Ten minutes later, in said suspension, a solution dissolving 16.7 parts of the compound of the above formula (25) in 2 parts of 28% ammonia water and 100 parts of water was added by pouring while maintaining said liquid temperature at 10° C. or below. In the meantime, 28% ammonia water was continuously added to maintain pH 9.0. With the same pH maintained, the liquid temperature was raised to 20° C. over 1 hour and the liquid was maintained at the same temperature for 8 hours. The liquid volume at this time was 720 parts. The temperature of the reaction liquid was raised to 50° C., 144 parts of sodium chloride (20% to the liquid) was added and stirred for 30 minutes, and then the pH of the liquid was controlled at 1.0 over 20 minutes. The precipitated crystals were separated by filtration and washed with 100 parts of a 20% aqueous sodium chloride solution to obtain 66.2 parts of a wet cake. To the obtained wet cake, 720 parts of water was added, and the pH of the resulting suspension was controlled at 9.0 using a 25% aqueous sodium hydroxide solution, to dissolve the wet cake. The liquid volume at this time was 600 parts. The temperature of the dissolving liquid was raised to 50° C., 160 parts of sodium chloride (20% to the liquid) was added and stirred for 30 minutes, and then the pH of the liquid was controlled at 1.0 over 20 minutes. The precipitated crystals were separated by filtration and washed with 100 parts of a 20% aqueous sodium chloride solution to obtain 49.2 parts of a wet cake. To the obtained wet cake, 420 parts of methanol and 80 parts of water were added, and stirred at 50° C. for 1 hour, followed by filtration to obtain 31.8 parts of a wet cake. The wet cake was dried to obtain 11.2 parts of a compound represented by the above formula (26) of the free acid as blue powder.

λmax: 601.0 nm (in an aqueous solution)

Example 9

(1) Synthesis of the Following Formula (27) (a Compound in which X is 4-sulfoanilino, Y is 2-hydroxyethoxyethylamino and E is Ethylene in the Formula (4))

Formula (27)

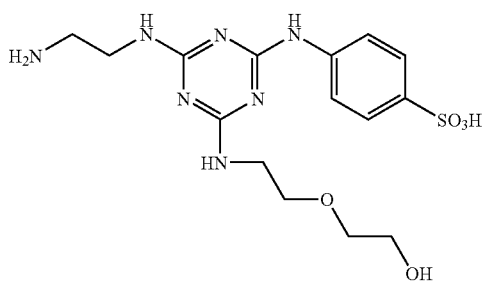

To 330 parts of ice water, 18.4 parts of cyanuric chloride and 0.2 parts of LEOCOL TD-90 (which is the trade name of a surfactant manufactured by Lion Corporation) were added, and stirred at 10° C. or below for 30 minutes. Next, 17.4 parts of 4-sulfoaniline (purity: 99.3%) was added, and reacted at 0 to 5° C. for 1 hour and at 25 to 30° C. for 1 hour while adjusting to pH 5.5 to 6.0 using a 10% aqueous sodium hydroxide solution. Next, 10.6 parts of aminoethoxyethanol was added to the reaction liquid and reacted at 45° C. for 30 minutes and at 50 to 55° C. for 1 hour while adjusting to pH 8.0 to 9.0 using a 10% aqueous sodium hydroxide solution. Then, 570 parts of ice was added to said reaction liquid to cool to 0° C. and then 60 parts of ethylenediamine was added dropwise while maintaining said liquid temperature at 5° C. or below. After that, the liquid was stirred overnight at room temperature. The pH of the resulting reaction liquid was controlled at 1.0 using concentrated hydrochloric acid. In the meantime, the temperature of 10 to 15° C. was maintained while adding ice. At this time, the liquid volume was 1750 parts. To this reaction liquid, 350 parts of sodium chloride was added, and stirred for 30 minutes to precipitate crystals. The precipitated crystals were filtered to obtain 40.0 parts of a wet cake. The obtained wet cake was put into a beaker, 800 parts of water was added, and the pH was adjusted to pH 9.0 using a 10% aqueous sodium hydroxide solution. At this time, the liquid volume was 900 parts. This reaction liquid was controlled at pH 1.0 using concentrated hydrochloric acid and 180 parts of sodium chloride was added and stirred for 30 minutes to precipitate crystals. The precipitated crystals were filtered to obtain 40.2 parts of a wet cake. The obtained wet cake was put into a beaker, and 300 parts of methanol and 30 parts of water were added and stirred at 50° C. for 1 hour, followed by filtration to obtain 36.2 parts of a wet cake. The obtained wet cake was dried to obtain 18.9 parts of white powder.

(2) Synthesis of the Following Formula (28) (a Compound in which 1.5 of A, B, C and D is a Pyridine Ring, the Rest 2.5 are Benzene Rings, E is Ethylene, X is 4-sulfoanilino, Y is 2-hydroxyethyl-2-ethoxy Amino, b is 1.7 and c is 0.8 in the Above Formula (1))

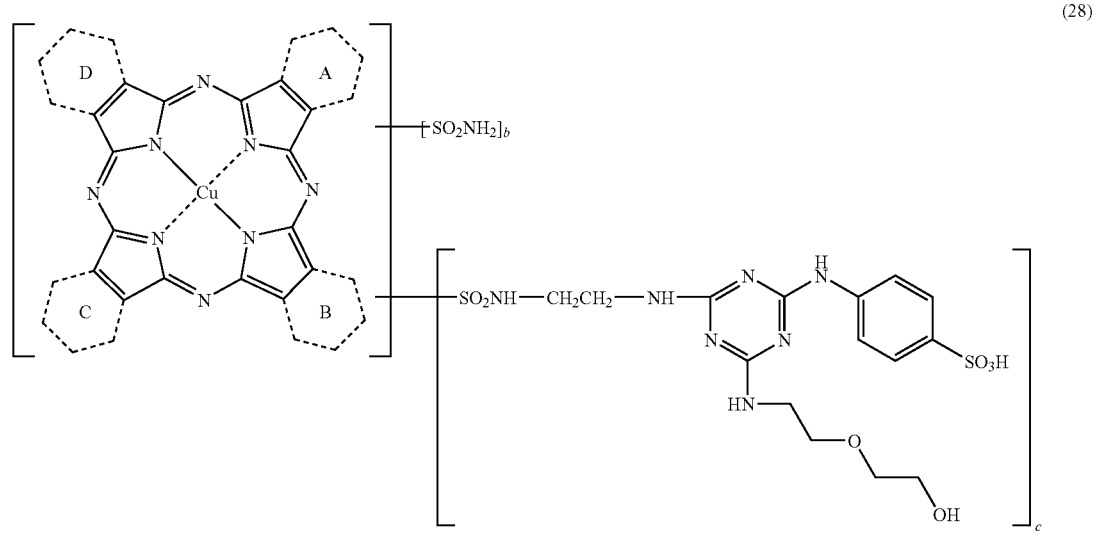

(28)

To 50 parts of ice water, 40.0 parts of a wet cake of a mixture of porphyrazine trisulfonyl chloride and copper dibenzobis(2,3-pyrido) porphyrazine disulfonyl chloride obtained in the same manner as in Example 1-(2) was added, and suspended by stirring at 5° C. or below. Ten minutes later, in said suspension, a solution dissolving 14.5 parts of the compound of the above formula (27) in 2 parts of 28% ammonia water and 100 parts of water was added by pouring while maintaining said liquid temperature at 10° C. or below. In the meantime, 28% ammonia water was continuously added to maintain pH 9.0. With the same pH maintained, the liquid temperature was raised to 20° C. over 1 hour and the liquid was maintained at the same temperature for 8 hours. The liquid volume at this time was 700 parts. The temperature of the reaction liquid was raised to 50° C., 140 parts of sodium chloride (20% to the liquid) was added and stirred for 30 minutes, and then the pH of the liquid was controlled at 1.0 over 20 minutes. The precipitated crystals were separated by filtration and washed with 100 parts of a 20% aqueous sodium chloride solution to obtain 94.0 parts of a wet cake. The obtained wet cake was dissolved in 370 parts of water by controlling at pH 10.0 using a 25% aqueous sodium hydroxide solution. The liquid volume at this time was 450 parts. The temperature of the dissolving liquid was raised to 50° C., 90 parts of sodium chloride (20% to the liquid) was added and stirred for 30 minutes, and then the pH of the liquid was controlled at 1.0 over 20 minutes. The precipitated crystals were separated by filtration and washed with 100 parts of a 20% aqueous sodium chloride solution to obtain 92.2 parts of a wet cake. To the obtained wet cake, 300 parts of methanol and 50 parts of water were added, and stirred at 50° C. for 1 hour, followed by filtration to obtain 76.2 parts of a wet cake. The wet cake was dried to obtain 23.2 parts of a compound (a compound in which b is 1.7 and c is 0.8) represented by the above formula (28) of the free acid as blue powder.

Example 10

(1) Synthesis of the Following Formula (29) (a Compound in which X is 2,5-disulfoanilino, Y is morpholino and E is Ethylene in the Formula (4))

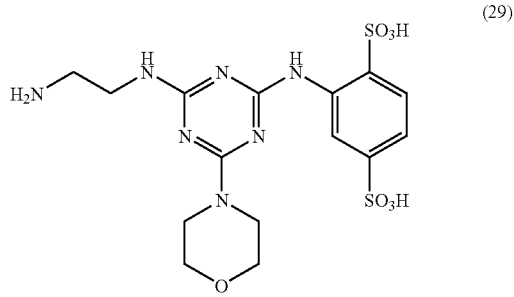

(29)

To 1300 parts of ice water, 115 parts of cyanuric chloride and 11 parts of LEOCOL TD-90 (which is the trade name of a surfactant manufactured by Lion Corporation) were added, and stirred at 10° C. or below for 30 minutes. Next, 199.5 parts of 2,5-disulfoaniline (purity: 90.2%) was added and reacted at 0 to 10° C. for 1 hour 30 minutes and at 20 to 25° C. for 1 hour 30 minutes while adjusting to pH 3.0 using a 10% aqueous sodium hydroxide solution. Next, 55 parts of morpholine was added to the reaction liquid and reacted at 30° C. for 2 hours while adjusting pH 6.0 to 7.0 using a 10% aqueous sodium hydroxide solution. Then, 1000 parts of ice was added to the resulting reaction liquid to cool to 0° C., and then 375 parts of ethylenediamine was added dropwise while maintaining said liquid temperature at 5° C. or below. After that, the liquid was stirred overnight at room temperature, and then controlled at pH 1.0 using concentrated hydrochloric acid. During this control of the pH, the temperature of 10 to 15° C. was maintained while adding ice. At this time, the liquid volume was 10000 parts. To this reaction liquid, 2000 parts of sodium chloride was added, and stirred for 30 minutes to precipitate crystals. The precipitated crystals were filtered to obtain 965 parts of a wet cake. The obtained wet cake was put into a beaker, 3850 parts of water was added, and the pH of the resulting liquid was adjusted to 9.0 using a 10% aqueous sodium hydroxide solution, to dissolve the wet cake. At this time, the liquid volume was 8000 parts. To this reaction liquid, 1600 parts of sodium chloride was added, and the mixture was controlled at pH 1.0 using concentrated hydrochloric acid and stirred for 30 minutes to precipitate crystals. The precipitated crystals were filtered to obtain 728 parts of a wet cake. The obtained wet cake was put into a beaker, and 1600 parts of methanol and 160 parts of water were added and stirred at 50° C. for 1 hour, followed by filtration to obtain 505.0 parts of a wet cake. The obtained wet cake was dried to obtain 269.1 parts of a compound of the above formula (29) as white powder.

(2) Synthesis of the Following Formula (30) (A Compound of 1.5 of A, B, C and D is a Pyridine Ring, the Rest 2.5 are Benzene Rings, E is Ethylene, X is 2,5-disulfoanilino and Y is Morpholino in the Above Formula (1))

To 50 parts of ice water, 40.0 parts of a wet cake of a mixture of porphyrazine trisulfonyl chloride and copper dibenzobis(2,3-pyrido) porphyrazine disulfonyl chloride obtained in the same manner as in Example 1-(2) was added, and suspended by stirring at 5° C. or below. Ten minutes later, in said suspension, a solution dissolving 14.3 parts of the compound of the above formula (29) in 2 parts of 28% ammonia water and 100 parts of water was added by pouring while maintaining said liquid temperature at 10° C. or below. In the meantime, 28% ammonia water was continuously added to maintain pH 9.0. With the same pH maintained, the liquid temperature was raised to 20° C. over 1 hour and the liquid was maintained at the same temperature for 8 hours. The liquid volume at this time was 650 parts. The temperature of the reaction liquid was raised to 50° C., 130 parts of sodium chloride (20% to the liquid) was added and stirred for 30 minutes, and then the pH of the liquid was controlled at 1.0 over 20 minutes. The precipitated crystals were separated by filtration and washed with 100 parts of a 20% aqueous sodium chloride solution to obtain 62.0 parts of a wet cake. To the obtained wet cake, 350 parts of water was added, and the pH of the resulting suspension was controlled at 9.5 using a 25% aqueous sodium hydroxide solution, to dissolve the wet cake. The liquid volume at this time was 450 parts. The temperature of the dissolving liquid was raised to 60° C., 90 parts of sodium chloride (20% to the liquid) was added and stirred for 30 minutes, and then the pH of the liquid was controlled at 1.0 over 20 minutes. The precipitated crystals were separated by filtration and washed with 100 parts of a 20% aqueous sodium chloride solution to obtain 58.8 parts of a wet cake. To the obtained wet cake, 470 parts of methanol and 118 parts of water were added, and stirred at 50° C. for 1 hour, followed by filtration to obtain 32.8 parts of a wet cake. The wet cake was dried to obtain 9.5 parts of a compound represented by the above formula (30) of the free acid as blue powder.

Formula (30)

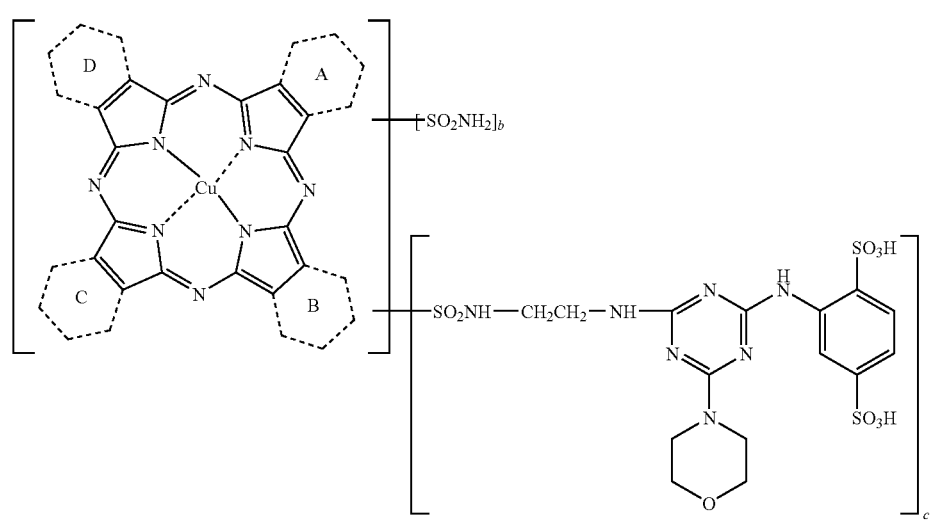

(30)

Example 11

(1) Synthesis of the Following Formula (31) (a Compound in which X is 2,4-disulfoanilino, Y is Morpholino and E is Ethylene in the Formula (4))

Formula (31)

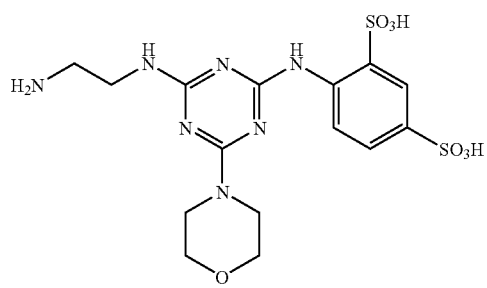

(31)

To 150 parts of ice water, 18.4 parts of cyanuric chloride and 0.2 parts of LEOCOL TD-90 (which is the trade name of a surfactant manufactured by Lion Corporation) were added, and stirred at 10° C. or below for 30 minutes. Next, 34.3 parts of 2,4-disulfoaniline (purity: 76.0%) was dissolved in 70 parts of water, and the mixture was added dropwise over 30 minutes to the stirred liquid obtained above. After that, the mixture was reacted at 20° C. or below for 30 minutes, and then adjusted to pH 3.0 using a 10% aqueous sodium hydroxide solution and reacted at 20° C. for 2 hours and at 30° C. for 2 hours. Next, 8.71 parts of morpholine was added dropwise over 15 minutes to the reaction liquid, the pH was controlled at 4.5, and reaction was conducted at 30° C. for 1.5 hours. Then, 250 parts of ice was added to said reaction liquid to cool to 0° C., and then 60 parts of ethylenediamine was added dropwise while maintaining said liquid temperature at 5° C. or below. After that, the liquid was stirred overnight at room temperature, and then concentrated hydrochloric acid was added to the resulting reaction liquid to control to pH 1.0. Thereto, 200 parts of ice was added to cool to 3° C. in order to precipitate crystals. The precipitated crystals were separated by filtration and the crystals were washed with methanol. In 300 parts of water, 58 parts of the obtained wet cake was added, and dissolved by adjusting the pH of the resulting suspension to 6.0 with a 10% aqueous sodium hydroxide solution. After that, concentrated hydrochloric acid was added to the obtained liquid to adjust the pH to 1.0, and 100 parts of ice was added to cool to 6° C. in order to precipitate crystals. The precipitated crystals were separated by filtration and washed with methanol to obtain 49.3 parts of a wet cake. The obtained wet cake was dried to obtain a compound of the above formula (31) as 33.7 parts of white powder.

(2) Synthesis of the Following Formula (32) (a Compound in which 1.5 of A, B, C and D is a Pyridine Ring, the Rest 2.5 are Benzene Rings, E is Ethylene, X is 2,4-disulfoanilino and Y is Morpholino in the Above Formula (1))

Formula (32)

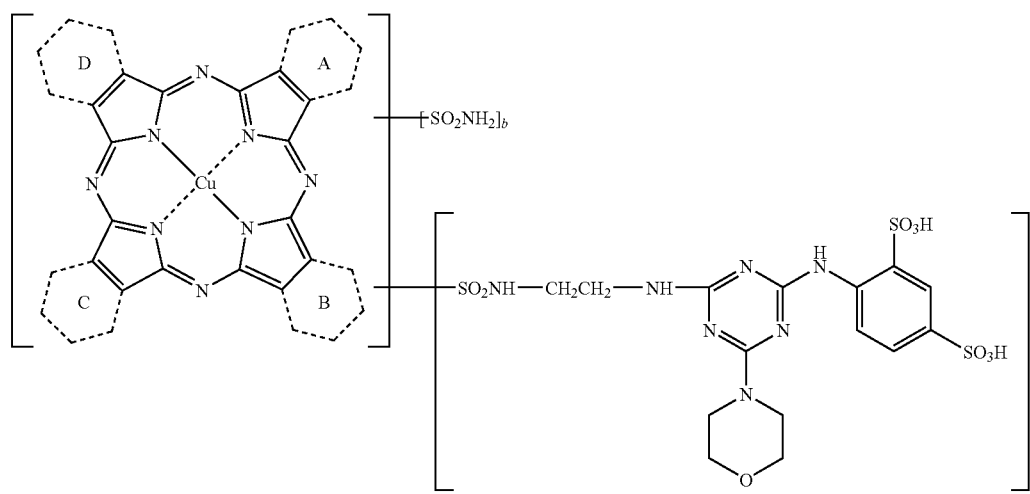

(32)

To 50 parts of ice water, 40.0 parts of a wet cake of a mixture of porphyrazine trisulfonyl chloride and copper dibenzobis(2,3-pyrido) porphyrazine disulfonyl chloride obtained in the same manner as in Example 1-(2) was added, and suspended by stirring at 5° C. or below. Ten minutes later, in said suspension, a solution dissolving 17.5 parts of a compound (purity: 89.4%) of the above formula (31) in 2 parts of 28% ammonia water and 100 parts of water was added by pouring while maintaining said liquid temperature at 10° C. or below. In the meantime, 28% ammonia water was continuously added to maintain pH 9.0. With the same pH maintained, the liquid temperature was raised to 20° C. over 1 hour and the liquid was maintained at the same temperature for 8 hours. The liquid volume at this time was 600 parts. The temperature of the reaction liquid was raised to 50° C., 120 parts of sodium chloride (20% to the liquid) was added and stirred for 30 minutes, and then the pH of the liquid was controlled at 1.0 over 20 minutes. The precipitated crystals were separated by filtration and washed with 100 parts of a 20% aqueous sodium chloride solution to obtain 64.3 parts of a wet cake. To the obtained wet cake, 400 parts of water was added, and the pH of said liquid was controlled at 9.5 using a 25% aqueous sodium hydroxide solution, to dissolve the wet cake. The liquid volume at this time was 450 parts. The temperature of the dissolving liquid was raised to 60° C., 90 parts of sodium chloride (20% to the liquid) was added and stirred for 30 minutes, and then the pH of the liquid was controlled at 1.0 over 20 minutes. The precipitated crystals were separated by filtration and washed with 100 parts of a 20% aqueous sodium chloride solution to obtain 89.1 parts of a wet cake. To the obtained wet cake, 802 parts of methanol and 89 parts of water were added, and stirred at 50° C. for 1 hour, followed by filtration to obtain 47.1 parts of a wet cake. The wet cake was dried to obtain 10.4 parts of a compound represented by the above formula (32) of the free acid as blue powder.

Example 12

(1) Synthesis of the Following Formula (33) (a Compound in which X is 3,8-disulfo-1-naphthylamino, Y is Morpholino and E is Ethylene in the Formula (4))

Formula (33)

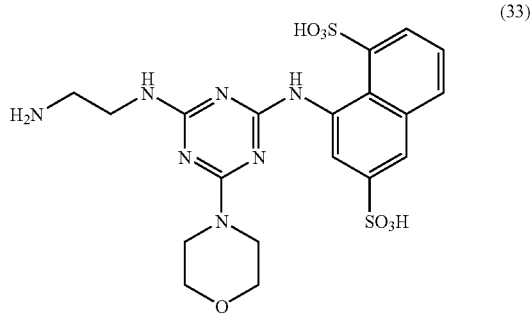

To 330 parts of ice water, 18.4 parts of cyanuric chloride and 0.2 parts of LEOCOL TD-90 (which is the trade name of a surfactant manufactured by Lion Corporation) were added, and stirred at 10° C. or below for 30 minutes. Next, 38.3 parts of 3,8-disulfo-1-naphthylamine (purity: 80.0%) was added to the stirred liquid obtained and reacted at 0 to 5° C. for 1 hour and at 25 to 30° C. for 2 hours while adjusting to pH 3.0 to 4.0 using a 10% aqueous sodium hydroxide solution. Next, 8.79 parts of morpholine was added to the reaction liquid, and reacted at pH 6.0 to 7.0 and 25° C. for 1 hour and at pH 7.5 to 8.0 and 25° C. for 30 minutes while adjusting the pH using a 10% aqueous sodium hydroxide solution. Then, 270 parts of ice was added to the resulting reaction liquid to cool to 0° C., and then 60 parts of ethylenediamine was added dropwise while maintaining said liquid temperature at 5° C. or below. After that, the liquid was stirred overnight at room temperature, and then controlled at pH 1.0 using concentrated hydrochloric acid. During this control of the pH, the temperature of 10 to 15° C. was maintained while adding ice. At this time, the liquid volume was 1750 parts. To this reaction liquid, 350 parts of sodium chloride was added, and stirred for 30 minutes to precipitate crystals. The precipitated crystals were filtered to obtain 75.0 parts of a wet cake. The obtained wet cake was put into a beaker, 450 parts of water was added, and the pH of the obtained liquid was adjusted to 9.0 using a 10% aqueous sodium hydroxide solution. At this time, the liquid volume was 700 parts. To this reaction liquid, concentrated hydrochloric acid was added to control the pH at 1.0, and then 140 parts of sodium chloride was added and stirred for 30 minutes to precipitate crystals. The precipitated crystals were filtered to obtain 42.1 parts of a wet cake. The obtained wet cake was put into a beaker, 300 parts of methanol and 30 parts of water were added and stirred at 50° C. for 1 hour, followed by filtration to obtain 35.4 parts of a wet cake. The obtained wet cake was dried to obtain 29.1 parts of a compound Formula (33) as white powder.

(2) Synthesis of the Following Formula (34) (a Compound in which 1.5 of A, B, C and D is a Pyridine Ring, the Rest 2.5 are Benzene Rings, E is Ethylene, X is 3,8-disulfo-1-naphthylamino and Y is Morpholino in the Above Formula (1))

Formula (34)

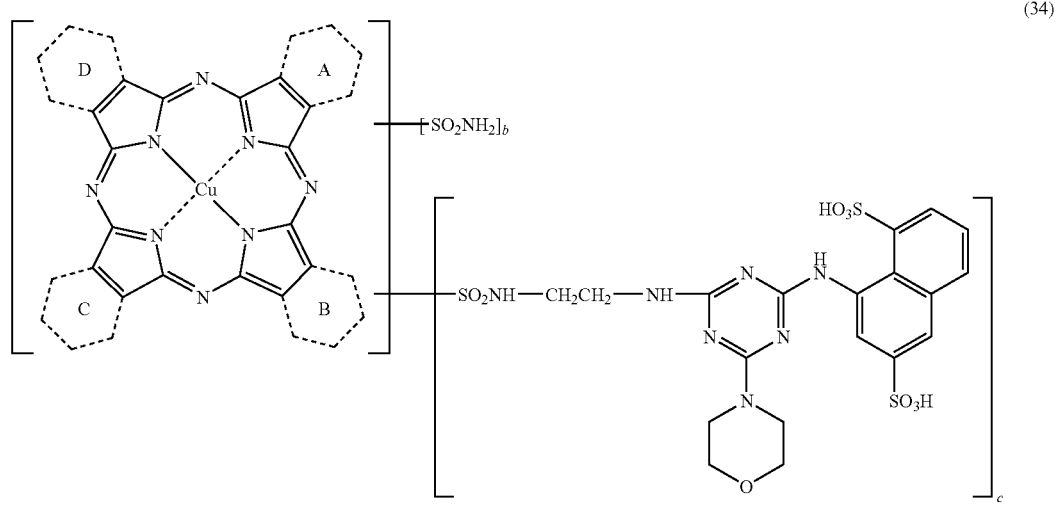

To 50 parts of ice water, 40.0 parts of a wet cake of a mixture of porphyrazine trisulfonyl chloride and copper dibenzobis(2,3-pyrido)porphyrazine disulfonyl chloride obtained in the same manner as in Example 1-(2) was added, and suspended by stirring at 5° C. or below. Ten minutes later, in said suspension, a solution dissolving 15.8 parts of a compound of the above formula (33) in 2 parts of 28% ammonia water and 100 parts of water was added by pouring while maintaining said liquid temperature at 10° C. or below. In the meantime, 28% ammonia water was continuously added to maintain pH 9.0. With the same pH maintained, the liquid temperature was raised to 20° C. over 1 hour and the liquid was maintained at the same temperature for 8 hours. The liquid volume at this time was 600 parts. The temperature of the reaction liquid was raised to 50° C., 120 parts of sodium chloride (20% to the liquid) was added and stirred for 30 minutes, and then the pH of the liquid was controlled at 1.0 over 20 minutes. The precipitated crystals were separated by filtration and washed with 100 parts of a 20% aqueous sodium chloride solution to obtain 64.2 parts of a wet cake. To the obtained wet cake, 410 parts of water was added, and the pH of the resulting suspension was controlled at 9.0 using a 25% aqueous sodium hydroxide solution, to dissolve the wet cake. The liquid volume at this time was 480 parts. The temperature of the dissolving liquid was raised to 50° C., 96 parts of sodium chloride (20% to the liquid) was added and stirred for 30 minutes, and then the pH of the liquid was controlled at 1.0 over 20 minutes. The precipitated crystals were separated by filtration and washed with 100 parts of a 20% aqueous sodium chloride solution to obtain 56.2 parts of a wet cake. To the obtained wet cake, 600 parts of methanol and 60 parts of water were added, and stirred at 50° C. for 1 hour, followed by filtration to obtain 32.5 parts of a wet cake. The wet cake was dried to obtain 11.9 parts of a compound represented by the above formula (34) of the free acid as blue powder.

λmax: 604.0 nm (in an aqueous solution)

Example 13

(1) Synthesis of the Following Formula (35) (a Compound in which X is 6,8-disulfo-2-naphthylamino, Y is Morpholino and E is Ethylene in the Formula (4))

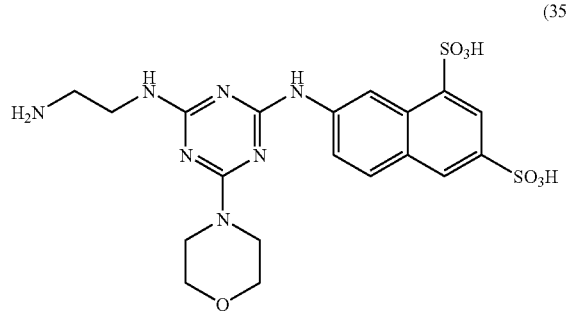

(35)

To 150 parts of ice water, 18.4 parts of cyanuric chloride and 0.2 parts of LEOCOL TD-90 (which is the trade name of a surfactant manufactured by Lion Corporation) were added, and stirred at 10° C. or below for 30 minutes. Next, 38.8 parts of 6,8-disulfo-2-naphthylamine (purity: 80.4%) was added and reacted at 6 to 8° C. for 3 hours and at 14 to 30° C. for 30 minutes while adjusting the pH of the obtained liquid to 2.0 to 3.0 using a 10% aqueous sodium hydroxide solution. Next, 8.71 parts of morpholine was added dropwise to the reaction liquid over 5 minutes and reacted at 30° C. for 2.5 hours while raising the pH to 4 to 6 using 10% sodium hydroxide. Then, 250 parts of ice was added to cool to 0° C., and then 60 parts of ethylenediamine was added dropwise while maintaining said liquid temperature at 5° C. or below. The liquid was stirred overnight at room temperature. The pH of the obtained reaction liquid was controlled at 2.0 using concentrated hydrochloric acid. In the meantime, the temperature of 10 to 15° C. was maintained while adding ice. At this time, the liquid volume was 600 parts. To this reaction liquid, 120 parts of sodium chloride was added, and stirred for 30 minutes to precipitate crystals. The precipitated crystals were filtered to obtain 374 parts of a wet cake. The obtained wet cake was put into a beaker, 400 parts of water was added, and the pH of the obtained liquid was adjusted to 9.0 using a 10% aqueous sodium hydroxide solution, to dissolve the wet cake. At this time, the liquid volume was 800 parts. To this reaction liquid, 160 parts of sodium chloride was added, and the pH was controlled at pH 1.1 using concentrated hydrochloric acid and the liquid was stirred for 30 minutes to precipitate crystals. The precipitated crystals were filtered to obtain 157 parts of a wet cake. The obtained wet cake was put into a beaker, 1413 parts of methanol and 157 parts of water were added and stirred at 50° C. for 1 hour, followed by filtration to obtain 145.2 parts of a wet cake. The obtained wet cake was dried to obtain 43.7 parts of a compound of the above formula (35) as white powder.

(2) Synthesis of the Following Formula (36) (a Compound in which 1.5 of A, B, C and D is a Pyridine Ring, the Rest 2.5 are Benzene Rings, E is Ethylene, X is 6,8-disulfo-2-naphthylamino and Y is Morpholino in the Above Formula (1))

Formula (36)

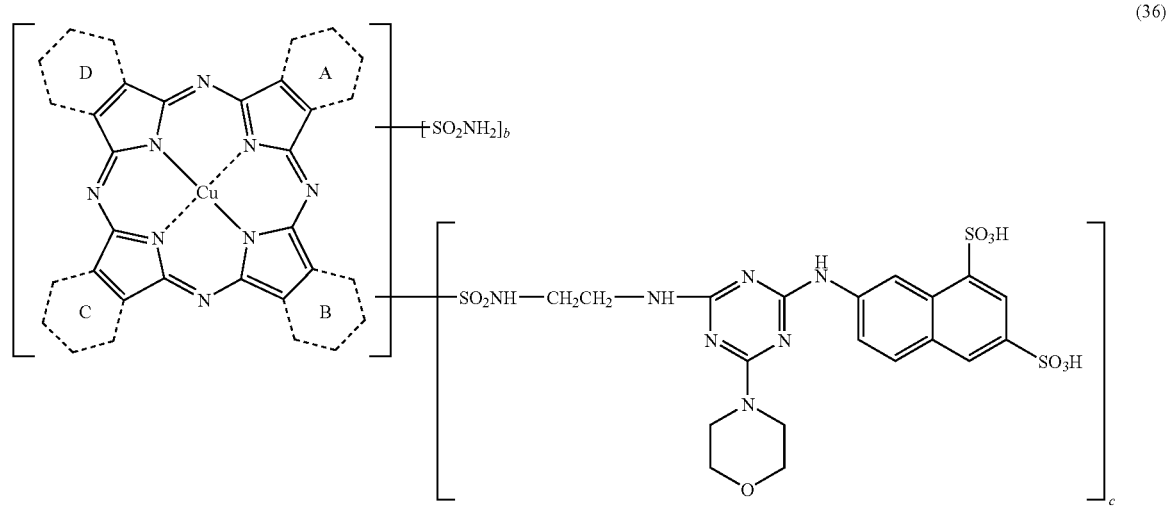

To 50 parts of ice water, 40.0 parts of a wet cake of a mixture of porphyrazine trisulfonyl chloride and copper dibenzobis(2,3-pyrido)porphyrazine disulfonyl chloride obtained in the same manner as in Example 1-(2) was added, and suspended by stirring 5° C. or below. Ten minutes later, in said suspension, a solution dissolving 19.6 parts (purity: 80.5%) of the compound of the above formula (35) in 2 parts of 28% ammonia water and 100 parts of water was added by pouring while maintaining said liquid temperature at 10° C. or below. In the meantime, 28% ammonia water was continuously added to maintain pH 9.0. With the same pH maintained, the liquid temperature was raised to 20° C. over 1 hour and the liquid was maintained at the same temperature for 8 hours. The liquid volume at this time was 850 parts. The temperature of the reaction liquid was raised to 50° C., 170 parts of sodium chloride (20% to the liquid) was added and stirred for 30 minutes, and then the pH of the liquid was controlled at 1.0 over 20 minutes. The precipitated crystals were separated by filtration and washed with 100 parts of a 20% aqueous sodium chloride solution to obtain 130 parts of a wet cake. To the obtained wet cake, 400 parts of water was added, and the pH of the obtained liquid was controlled at 9.5 using a 25% aqueous sodium hydroxide solution, to dissolve the wet cake. The liquid volume at this time was 580 parts. The temperature of the dissolving liquid was raised to 60° C., 116 parts of sodium chloride (20% to the liquid) was added and stirred for 30 minutes, and then the pH of the liquid was controlled at 1.0 over 20 minutes. The precipitated crystals were separated by filtration and washed with 100 parts of a 20% aqueous sodium chloride solution to obtain 130 parts of a wet cake. To the obtained wet cake, 1040 parts of methanol and 260 parts of water were added, and stirred at 50° C. for 1 hour, followed by filtration to obtain 72.4 parts of a wet cake. The wet cake was dried to obtain 19.7 parts of a compound represented by the above formula (36) of the free acid as blue powder.

λmax: 602.0 nm (in an aqueous solution)

Example 14

(1) Synthesis of the Following Formula (37) (a Compound in which X is 2,5-disulfoanilino, Y is piperidino and E is Ethylene in the Formula (4))

Formula (37)

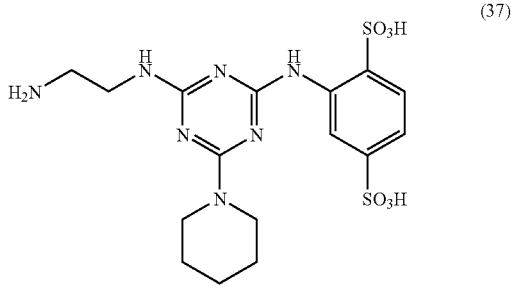

To 1300 parts of ice water, 18.4 parts of cyanuric chloride and 11 parts of LEOCOL TD-90 (which is the trade name of a surfactant manufactured by Lion Corporation) were added, and stirred at 10° C. or below for 30 minutes. Next, 31.3 parts of 2,5-disulfoaniline (purity: 90.2%) was added thereto, and reacted at 0 to 10° C. for 1 hour 30 minutes and at 20 to 25° C. for 1 hour 30 minutes while adjusting the pH of the obtained liquid to 3.0 using a 10% aqueous sodium hydroxide solution. Next, 8.52 parts of piperidine was added to the reaction liquid, and reacted at 30° C. for 2 hours while adjusting pH 6.0 to 7.0 using a 10% aqueous sodium hydroxide solution. Then, 100 parts of ice was added to the resulting reaction liquid to cool to 0° C., and then 60.2 parts of ethylenediamine was added dropwise while maintaining said liquid temperature at 5° C. or below. After that, the liquid was stirred overnight at room temperature, and then concentrated hydrochloric acid was added to the reaction liquid to control at pH 1.0. During this control of the pH, the temperature of 10 to 15° C. was maintained while adding ice. At this time, the liquid volume was 800 parts. To this reaction liquid, 160 parts of sodium chloride was added, and stirred for 30 minutes to precipitate crystals. The precipitated crystals were filtered to obtain 57.2 parts of a wet cake. The obtained wet cake was put into a beaker, 200 parts of water was added, and the pH was adjusted to 9.0 using a 10% aqueous sodium hydroxide solution, to dissolve the wet cake. At this time, the liquid volume was 300 parts. To this reaction liquid, 60 parts of sodium chloride was added, and the liquid was controlled at pH 1.0 using concentrated hydrochloric acid and stirred for 30 minutes to precipitate crystals. The precipitated crystals were filtered to obtain 51.2 parts of a wet cake. The obtained wet cake was put into a beaker, 200 parts of methanol and 100 parts of water were added and stirred at 50° C. for 1 hour, followed by filtration to obtain 48.2 parts of a wet cake. The obtained wet cake was dried to obtain 36.8 parts of the formula (37) as white powder.

(2) Synthesis of the Following Formula (38) (a Compound in which 1.5 of A, B, C and D is a Pyridine Ring, the Rest 2.5 are Benzene Rings, E is Ethylene, X is 2,5-disulfoanilino and Y is Piperidino in the Above Formula (1))

To 50 parts of ice water, 40.0 parts of a wet cake of a mixture of porphyrazine trisulfonyl chloride and copper dibenzobis(2,3-pyrido)porphyrazine disulfonyl chloride obtained in the same manner as in Example 1-(2) was added, and suspended by stirring at 5° C. or below. Ten minutes later, in said suspension, a solution dissolving 14.3 parts of the compound of the above formula (37) in 2 parts of 28% ammonia water and 100 parts of water was added by pouring while maintaining said liquid temperature at 10° C. or below. In the meantime, 28% ammonia water was continuously added to maintain pH 9.0. With the same pH maintained, the liquid temperature was raised to 20° C. over 1 hour and the liquid was maintained at the same temperature for 8 hours. The liquid volume at this time was 650 parts. The temperature of the reaction liquid was raised to 50° C., 130 parts of sodium chloride (20% to the liquid) was added and stirred for 30 minutes, and then the pH of the liquid was controlled at 1.0 over 20 minutes. The precipitated crystals were separated by filtration and washed with 100 parts of a 20% aqueous sodium chloride solution to obtain 62.0 parts of a wet cake. The obtained wet cake was dissolved in 350 parts of water by controlling at pH 9.5 using a 25% aqueous sodium hydroxide solution. The liquid volume at this time was 450 parts. The temperature of the dissolving liquid was raised to 60° C., 90 parts of sodium chloride (20% to the liquid) was added and stirred for 30 minutes, and the pH of the liquid was controlled at 1.0 over 20 minutes. The precipitated crystals were separated by filtration and washed with 100 parts of a 20% aqueous sodium chloride solution to obtain 58.8 parts of a wet cake. To the obtained wet cake, 470 parts of methanol and 118 parts of water were added, and stirred at 50° C. for 1 hour, followed by filtration to obtain 32.8 parts of a wet cake. The wet cake was dried to obtain 9.5 parts of a compound represented by the above formula (38) as the free acid, as blue powder.

λmax: 603.5 nm (in an aqueous solution)

Formula (38)

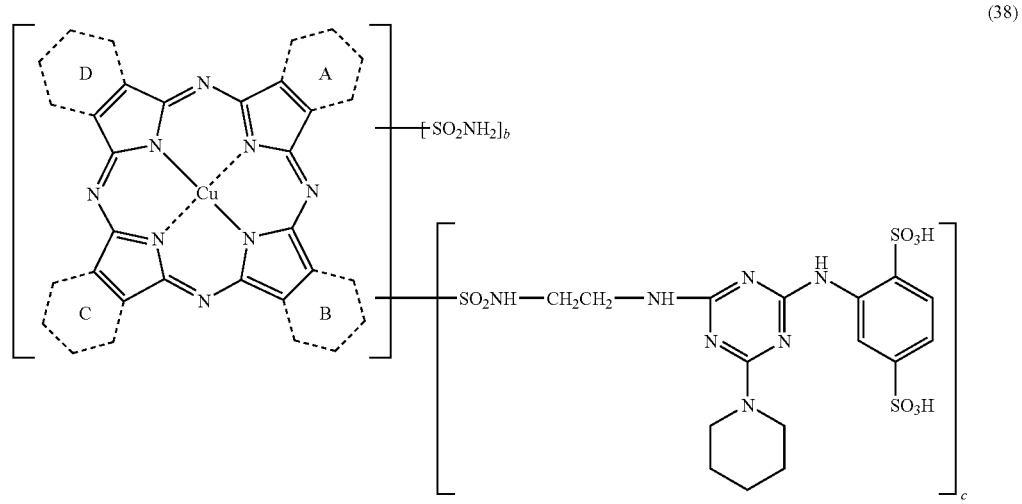

(38)

Example 15

(1) Synthesis of the Following Formula (39) (a Compound in which X is 2,5-disulfoanilino, Y is Pyrrolidine and E is Ethylene in the Formula (4))

Formula (39)

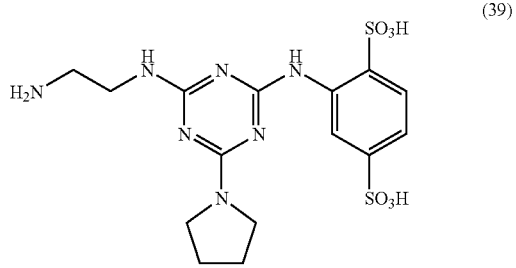

(39)

To 1300 parts of ice water, 18.4 parts of cyanuric chloride and 11 parts of LEOCOL TD-90 (which is the trade name of a surfactant manufactured by Lion Corporation) were added, and stirred at 10° C. or below for 30 minutes. Next, 31.3 parts of 2,5-disulfoaniline (purity: 90.2%) was added thereto and reacted 0 to 10° C. for 1 hour 30 minutes and at 20 to 25° C. for 1 hour 30 minutes while adjusting to pH 3.0 using a 10% aqueous sodium hydroxide solution. Next, 7.2 parts of pyrrolidine was added to the reaction liquid and reacted at 30° C. for 2 hours while adjusting to pH 6.0 to 7.0 using a 10% aqueous sodium hydroxide solution. To the obtained reaction liquid, 100 parts of ice was added to cool to 0° C., and then 60.2 parts of ethylenediamine was added dropwise to said reaction liquid while maintaining said liquid temperature at 5° C. or below. After that, the liquid was stirred overnight at room temperature. The pH of the obtained reaction liquid was controlled at 1.0 using concentrated hydrochloric acid. In the meantime, the temperature of 10 to 15° C. was maintained while adding ice. At this time, the liquid volume was 800 parts. To this reaction liquid, 160 parts of sodium chloride was added and stirred for 30 minutes to precipitate crystals. The precipitated crystals were filtered to obtain 88.2 parts of a wet cake. The obtained wet cake was put into a beaker, 400 parts of water was added, and the pH of said liquid was adjusted to 9.0 using a 10% aqueous sodium hydroxide solution, to dissolve the wet cake. At this time, the liquid volume was 300 parts. To this solution, 80 parts of sodium chloride was added, and then the pH was controlled at 1.0 using concentrated hydrochloric acid, followed by stirring for 30 minutes to precipitate crystals. The precipitated crystals were filtered to obtain 85.2 parts of a wet cake. The obtained wet cake was put into a beaker, 200 parts of methanol and 100 parts of water were added and stirred at 50° C. for 1 hour, followed by filtration to obtain 65.3 parts of a wet cake. The obtained wet cake was dried to obtain 31.0 parts of a compound of the above formula (39) as white powder.

(2) Synthesis of the Following Formula (40) (a Compound in which 1.5 of A, B, C and D is a Pyridine Ring, the Rest 2.5 are Benzene Rings, E is Ethylene, X is 2,5-disulfoanilino and Y is Pyrrolidine in the Above Formula (1))

Formula (40)

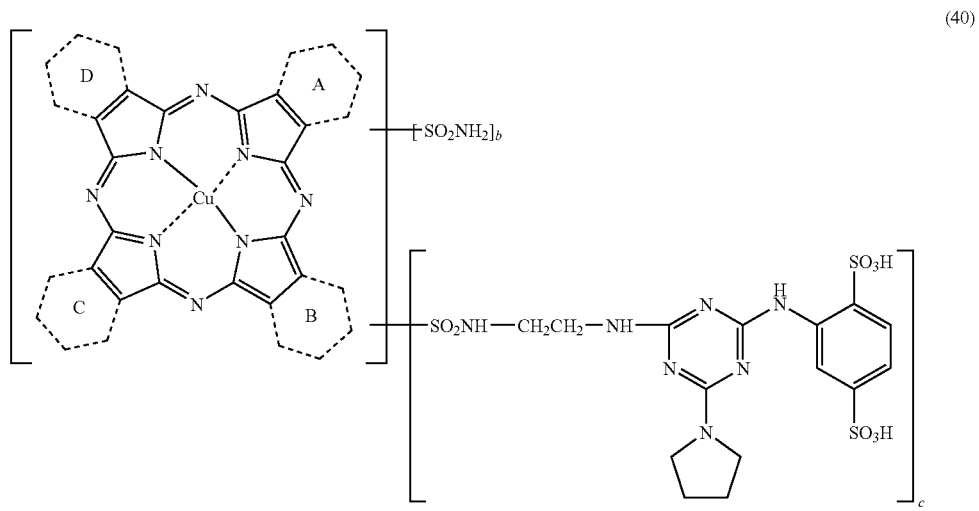

(40)

To 400 parts of ice water, 43.1 parts of a wet cake of a mixture of porphyrazine trisulfonyl chloride and copper dibenzobis(2,3-pyrido)porphyrazine disulfonyl chloride obtained in the same manner as in Example 1-(2) was added, and suspended by stirring at 5° C. or below. Ten minutes later, in said suspension, a solution dissolving 13.3 parts (purity: 94.8%) of a compound of the above formula (39) in 2 parts of 28% ammonia water and 100 parts of water was added by pouring while maintaining said liquid temperature at 10° C. or below. In the meantime, 28% ammonia water was continuously added to maintain pH 9.0. With the same pH maintained, the liquid temperature was raised to 20° C. over 1 hour and the liquid was maintained at the same temperature for 6 hours. The liquid volume at this time was 600 parts. The temperature of the reaction liquid was raised to 50° C., 120 parts of sodium chloride (20% to the liquid) was added thereto and stirred for 30 minutes, and then the pH of the liquid was controlled at 1.0 over 20 minutes. The precipitated crystals were separated by filtration and washed with 100 parts of a 20% aqueous sodium chloride solution to obtain 51.4 parts of a wet cake. To the obtained wet cake, 400 parts of water was added, and the pH was controlled at 8.3 using a 25% aqueous sodium hydroxide solution, to dissolve the wet cake. The liquid volume at this time was 450 parts. The temperature of the dissolving liquid was raised to 60° C., 90 parts of sodium chloride (20% to the liquid) was added and stirred for 30 minutes, and then the pH of the liquid was controlled at 1.0 over 20 minutes. The precipitated crystals were separated by filtration and washed with 100 parts of a 20% aqueous sodium chloride solution to obtain 50.9 parts of a wet cake. To the obtained wet cake, 407.2 parts of methanol and 101.8 parts of water were added, and stirred at 50° C. for 1 hour, followed by filtration to obtain 29.2 parts of a wet cake. The wet cake was dried to obtain 10.4 parts of a compound represented by the above formula (40) of the free acid as blue powder.

λmax: 604.5 nm (in an aqueous solution)

Example 16

(1) Synthesis of the Following Formula (41) (a Compound in which X is 2,5-disulfoanilino, Y is 2-carboxypyrrolidino and E is Ethylene in the Formula (4))

Formula (41)

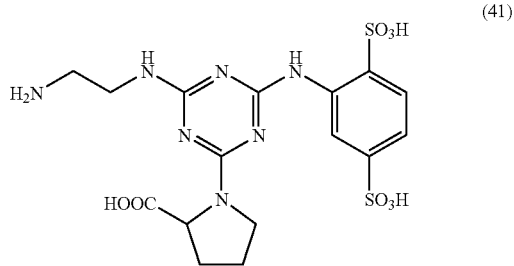

(41)

To 1300 parts of ice water, 18.4 parts of cyanuric chloride and 0.1 part of LEOCOL TD-90 (which is the trade name of a surfactant manufactured by Lion Corporation) were added, and stirred at 10° C. or below for 30 minutes. Next, 31.3 parts of 2,5-disulfoaniline (purity: 90.2%) was added and reacted at 0 to 10° C. for 1 hour 30 minutes and at 20 to 25° C. for 1 hour 30 minutes while adjusting the pH to 3.0 using a 10% aqueous sodium hydroxide solution. Next, 11.5 parts of 2-carboxy pyrrolidine was added to the reaction liquid and reacted at 30° C. for 2 hours while adjusting the pH to 6.0 to 7.0 using a 10% aqueous sodium hydroxide solution. Then, 100 parts of ice was added to the obtained reaction liquid to cool to 0° C., and then 60.2 parts of ethylenediamine was added dropwise while maintaining said liquid temperature at 5° C. or below. After that, the liquid was stirred overnight at room temperature. The pH of the resulting reaction liquid was controlled at 1.0 using concentrated hydrochloric acid. In the meantime, the temperature of 10 to 15° C. was maintained while adding ice. At this time, the liquid volume was 800 parts. To this reaction liquid, 160 parts of sodium chloride was added, and stirred for 30 minutes to precipitate crystals. The precipitated crystals were filtered to obtain 149.5 parts of a wet cake. The obtained wet cake was put into a beaker, 300 parts of water was added, and the pH was adjusted to 9.0 using a 10% aqueous sodium hydroxide solution, to dissolve the wet cake. At this time, the liquid volume was 450 parts. To this solution, 90 parts of sodium chloride was added, and then the pH was controlled at 1.0 using concentrated hydrochloric acid, followed by stirring for 30 minutes to precipitate crystals. The precipitated crystals were filtered to obtain 213.2 parts of a wet cake. The obtained wet cake was put into a beaker, and 300 parts of methanol and 200 parts of water were further added and stirred at 50° C. for 1 hour, followed by filtration to obtain 117.2 parts of a wet cake. The obtained wet cake was dried to obtain 30.7 parts of a compound of the above formula (41) as white powder.

(2) Synthesis of the Following Formula (42) (a Compound in which 1.5 of A, B, C and D is a Pyridine Ring, the Rest 2.5 are Benzene Rings, E is Ethylene, X is 2,5-disulfoanilino and Y is 2-carboxypyrrolidino in the Above Formula (1))

Formula (42)

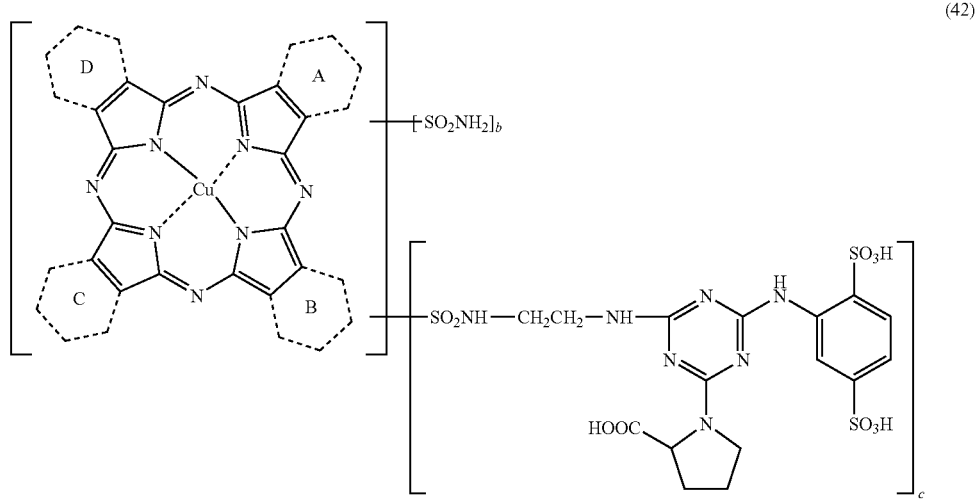

(42)

To 50 parts of ice water, 40.0 parts of a wet cake of a mixture of copper porphyrazine trisulfonyl chloride and copper dibenzobis(2,3-pyrido)porphyrazine disulfonyl chloride obtained in the same manner as in Example 1-(2) was added, and suspended by stirring at 5° C. or below. Ten minutes later, in said suspension, a solution dissolving 15.9 parts of the compound of the above formula (41) in 2 parts of 28% ammonia water and 100 parts of water was added by pouring while maintaining said liquid temperature at 10° C. or below. In the meantime, 28% ammonia water was continuously added to maintain pH 9.0. With the same pH maintained, the liquid temperature was raised to 20° C. over 1 hour and the liquid was maintained at the same temperature for 8 hours. The liquid volume at this time was 650 parts. The temperature of the reaction liquid was raised to 50° C., 130 parts of sodium chloride (20% to the liquid) was added and stirred for 30 minutes, and then the pH of the liquid was controlled at 1.0 over 20 minutes. The precipitated crystals were separated by filtration and washed with 100 parts of a 20% aqueous sodium chloride solution to obtain 114 parts of a wet cake. To the obtained wet cake, 600 parts of water was added, and the pH of the resulting liquid was controlled at 9.5 using a 25% aqueous sodium hydroxide solution, to dissolve the wet cake. The liquid volume at this time was 750 parts. The temperature of the dissolving liquid obtained was raised to 60° C., 90 parts of sodium chloride (20% to the liquid) was added and stirred for 30 minutes, and then the pH of the liquid was controlled at 1.0 over 20 minutes. The precipitated crystals were separated by filtration and washed with 150 parts of a 20% aqueous sodium chloride solution to obtain 58.2 parts of a wet cake. To the obtained wet cake, 320 parts of methanol and 80 parts of water were added, and stirred at 50° C. for 1 hour, followed by filtration to obtain 31.5 parts of a wet cake. The wet cake was dried to obtain 7.6 parts of a compound represented by the above formula (42) of the free acid as blue powder.

λmax: 591.0 nm (in an aqueous solution)

Example 17

(1) Synthesis of the Following Formula (43) (a Compound in which X is 2,5-disulfoanilino, Y is 1-ethylpiperazino and E is Ethylene in the Formula (4))

Formula (43)

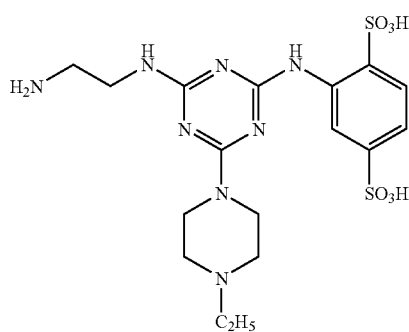

To 150 parts of ice water, 18.4 parts of cyanuric chloride and 0.2 parts of LEOCOL TD-90 (which is the trade name of a surfactant manufactured by Lion Corporation) were added, and stirred at 10° C. or below for 30 minutes. Next, 31.3 parts of 2,5-disulfoaniline (purity: 90.5%) was added thereto and reacted at 0 to 25° C. for 4 hours while adjusting the pH to 3.0 using a 10% aqueous sodium hydroxide solution. Next, 11.4 parts of 1-ethylpiperazine was made into a 10% solution with water, which was then added dropwise over 1 hour to the reaction liquid maintained at 30° C., and after that, reaction was conducted for 2 hours. The liquid temperature was controlled at 50° C., 60.1 parts of ethylenediamine was added to the resulting reaction liquid and stirred overnight at room temperature, and then the liquid temperature was controlled at 50° C. The liquid volume at that time was 600 parts. After 120 parts of sodium chloride was added to this reaction liquid and dissolved, the pH was adjusted to 1.0 with concentrated hydrochloric acid and the liquid was stirred for 30 minutes to precipitate crystals. The precipitated crystals were filtered to obtain 89.4 parts of a wet cake. The obtained wet cake was put into a beaker, 200 parts of water was added, and the pH was adjusted to 7.0 using a 10% aqueous sodium hydroxide solution, to dissolve the wet cake. At this time, the liquid volume was 250 parts. To this reaction liquid, 50 parts of sodium chloride was added, the pH was controlled at 1.0 using concentrated hydrochloric acid, and the liquid was stirred for 30 minutes to precipitate crystals. The precipitated crystals were filtered to obtain 100 parts of a wet cake. The obtained wet cake was put into a beaker, and 800 parts of methanol and 200 parts of water were further added and stirred at 50° C. for 1 hour, followed by filtration to obtain 80.1 parts of a wet cake. The obtained wet cake was dried to obtain 39.6 parts of a compound of the formula (43) as white powder.

(2) Synthesis of the Following Formula (44) (a Compound in which 1.5 of A, B, C and D is a Pyridine Ring, the Rest 2.5 are Benzene Rings, X is 2,5-disulfoanilino, Y is 1-ethylpiperadino, E is Ethylene, b is 1.7 and c is 0.8 in the Above Formula (1))

Formula (44)

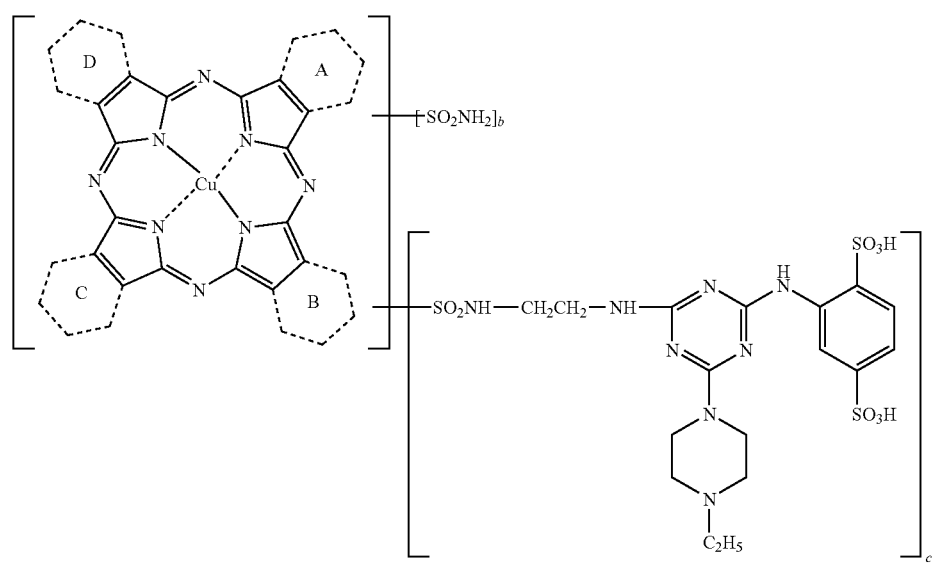

To 50 parts of ice water, 43.2 parts of a wet cake of a mixture of copper porphyrazine trisulfonyl chloride and copper dibenzobis(2,3-pyrido)porphyrazine disulfonyl chloride obtained in the same manner as in Example 1-(2) was added, and suspended by stirring at 5° C. or below. Ten minutes later, in said suspension, a solution dissolving 16.7 parts (purity: 90.3%) of the compound of the above formula (43) in 2 parts of 28% ammonia water and 100 parts of water was added by pouring while maintaining said liquid temperature at 10° C. or below. In the meantime, 28% ammonia water was continuously added to maintain pH 9.0. With the same pH maintained, the liquid temperature was raised to 20° C. over 1 hour and the liquid was maintained at the same temperature for 8 hours. The liquid volume at this time was 650 parts. The temperature of the reaction liquid was raised to 50° C., 130 parts of sodium chloride (20% to the liquid) was added and stirred for 30 minutes, and then the pH of the liquid was controlled at 1.0 over 20 minutes. The precipitated crystals were separated by filtration and washed with 100 parts of a 20% aqueous sodium chloride solution to obtain 60.4 parts of a wet cake. To the obtained wet cake, 400 parts of water was added, and the pH of the resulting suspension was controlled at 9.0 using a 25% aqueous sodium hydroxide solution, to dissolve the wet cake. The liquid volume at this time was 450 parts. The temperature of the dissolving liquid was raised to 60° C., 90 parts of sodium chloride (20% to the liquid) was added and stirred for 30 minutes, and then the pH of the liquid was controlled at 1.0 over 20 minutes. The precipitated crystals were separated by filtration and washed with 100 parts of a 20% aqueous sodium chloride solution to obtain 83.2 parts of a wet cake. To the obtained wet cake, 666 parts of methanol and 166 parts of water were added, and stirred at 50° C. for 1 hour, followed by filtration to obtain 53.3 parts of a wet cake. The wet cake was dried to obtain 12.1 parts of a compound represented by the above formula (44) of the free acid as blue powder.

λmax: 602.5 nm (in an aqueous solution)

Example 18

(1) Synthesis of the Following Formula (45) (a Compound in which X is 2,5-disulfoanilino, Y is 2-ethylpiperidino and E is Ethylene in the Formula (4))

Formula (45)

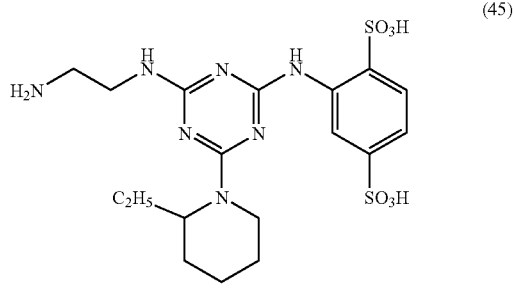

To 300 parts of ice water, 18.4 parts of cyanuric chloride and 0.2 parts of LEOCOL TD-90 (which is the trade name of a surfactant manufactured by Lion Corporation) were added, and stirred at 10° C. or below for 30 minutes. Next, 31.3 parts of 2,5-disulfoaniline (purity: 90.5%) was added thereto and reacted at 0 to 10° C. for 1 hour 30 minutes and at 20 to 25° C. for 1 hour 30 minutes while adjusting the pH to 3.0 using a 10% aqueous sodium hydroxide solution. Next, 11.3 parts of 2-ethylpiperidine was added dropwise over 40 minutes to the reaction liquid maintained at 25° C. in such a way that pH 8.5 to 8.7 could be maintained. The reaction was conducted at 30° C. for 3 hours while adjusting the pH of the resulting liquid to 9.0 using a 10% aqueous sodium hydroxide solution. Then, the temperature of said liquid was raised to 50° C., and then 60.1 parts of ethylenediamine was added and stirred overnight at room temperature. And the pH of the resulting reaction liquid was adjusted to 1.0 using concentrated hydrochloric acid. The liquid volume when the temperature of the reaction liquid was raised to 50° C. was 500 parts. To this reaction liquid, 100 parts of sodium chloride was added, and stirred for 30 minutes to precipitate crystals. The precipitated crystals were filtered to obtain 72.3 parts of a wet cake. The obtained wet cake was put into a beaker, and 651 parts of methanol and 72.3 parts of water were further added and stirred at 50° C. for 1 hour. The resulting suspension was filtered to obtain 52.1 parts of a wet cake. Said wet cake was dried to obtain 31.2 parts of a compound of the above formula (45) as white powder.

(2) Synthesis of the Following Formula (46) (a Compound in which 1.5 of A, B, C and D is a Pyridine Ring, the Rest 2.5 are Benzene Rings, E is Ethylene, X is 2,5-disulfoanilino and Y is 2-ethylpiperidino in the Above Formula (1))

To 400 parts of ice water, 43.2 parts of a wet cake of a mixture of porphyrazine trisulfonyl chloride and copper dibenzobis(2,3-pyrido)porphyrazine disulfonyl chloride obtained in the same manner as in Example 1-(2) was added, and suspended by stirring at 5° C. or below. Ten minutes later, in said suspension, a solution dissolving 16.7 parts (purity: 90%) of a compound of the above formula (45) in 2 parts of 28% ammonia water and 100 parts of water was added by pouring while maintaining said liquid temperature at 10° C. or below. In the meantime, 28% ammonia water was continuously added to maintain pH 9.0. With the same pH maintained, the liquid temperature was raised to 20° C. over 1 hour and the liquid was maintained at the same temperature for 7 hours. The liquid volume at this time was 600 parts. The temperature of the reaction liquid was raised to 50° C., and 120 parts of sodium chloride (20% to the liquid) was added thereto and stirred for 30 minutes. Then, the pH of the liquid was controlled at 1.0 over 20 minutes. The precipitated crystals were separated by filtration and washed with 100 parts of a 20% aqueous sodium chloride solution to obtain 86.4 parts of a wet cake. To the obtained wet cake, 350 parts of water was added, and the pH of the resulting suspension was controlled at 9.0 using a 25% aqueous sodium hydroxide solution, to dissolve said wet cake. The liquid volume at this time was 400 parts. The temperature of the dissolving liquid was raised to 60° C., and 80 parts of sodium chloride (20% to the liquid) was added thereto and stirred for 30 minutes. And the pH of the liquid was controlled at 1.0 over 20 minutes. The precipitated crystals were separated by filtration and washed with 100 parts of a 20% aqueous sodium chloride solution to obtain 104 parts of a wet cake. To the obtained wet cake, 832 parts of methanol and 208 parts of water were added, and stirred at 50° C. for 1 hour, followed by filtration to obtain 44.7 parts of a wet cake. The wet cake was dried to obtain 9.3 parts of a compound represented by the above formula (46) of the free acid as blue powder.

λmax: 601.0 nm (in an aqueous solution)

Formula (46)

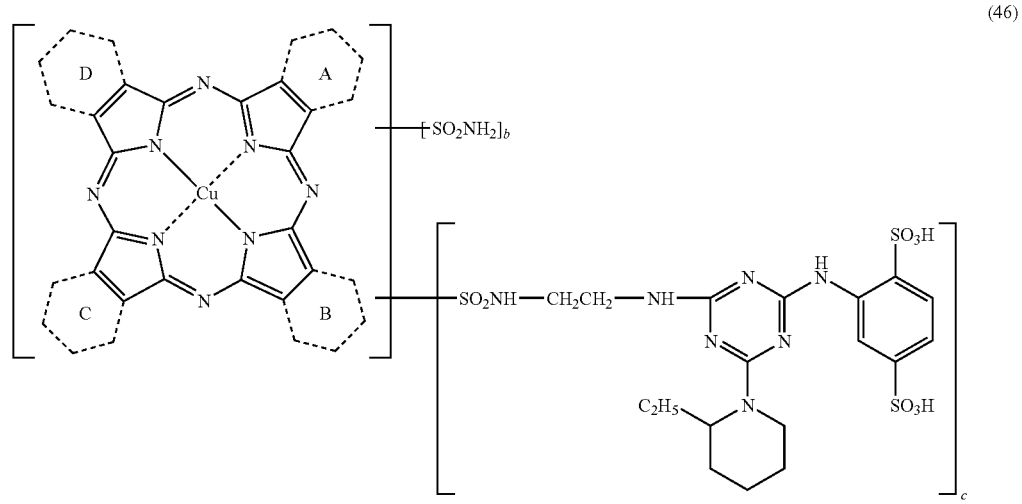

(46)

Example 19

(1) Synthesis of the Following Formula (47) (a Compound in which X is 2,5-disulfoanilino, Y is 3-methylpiperidino Pyrrolidinyl and E is Ethylene in the Formula (4))

Formula (47)

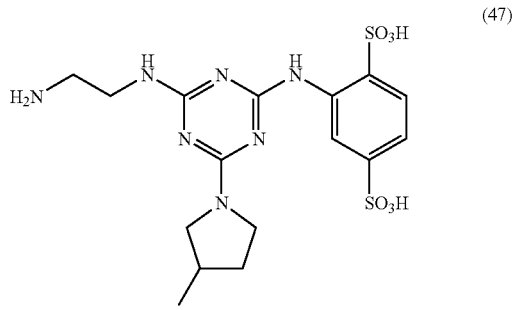

(47)

temperature was controlled at 50° C. The liquid volume at that time was 620 parts. To this reaction liquid, 124 parts of sodium chloride was added, and dissolved, and then the pH was adjusted to 1.0 with concentrated hydrochloric acid, followed by stirring for 30 minutes to precipitate crystals. The precipitated crystals were filtered to obtain 68.1 parts of a wet cake. The obtained wet cake was put into a beaker, 340 parts of water was further added, and the pH of the resulting suspension was adjusted to 9.0 using a 10% aqueous sodium hydroxide solution, to dissolve the wet cake. At this time, the liquid volume was 420 parts. To this solution, 84 parts of sodium chloride was added, and then the pH of the liquid was controlled at 1.0 using concentrated hydrochloric acid, followed by stirring for 30 minutes to precipitate crystals. The precipitated crystals were filtered to obtain 100 parts of a wet cake. The obtained wet cake was put into a beaker, 300 parts of methanol and 200 parts of water were further added and stirred at 50° C. for 1 hour. The resulting suspension was filtered to obtain 37.1 parts of a wet cake. The obtained wet cake was dried to obtain 30.1 parts of a compound of the above formula (47) as white powder.

(2) Synthesis of the Following Formula (48) (a Compound in which 1.5 of A, B, C and D is a Pyridine Ring, the Rest 2.5 are Benzene Rings, E is Ethylene, X is 2,5-disulfoanilino and Y is 3-methylpyrrolidinyl in the Above Formula (1))

Formula (48)

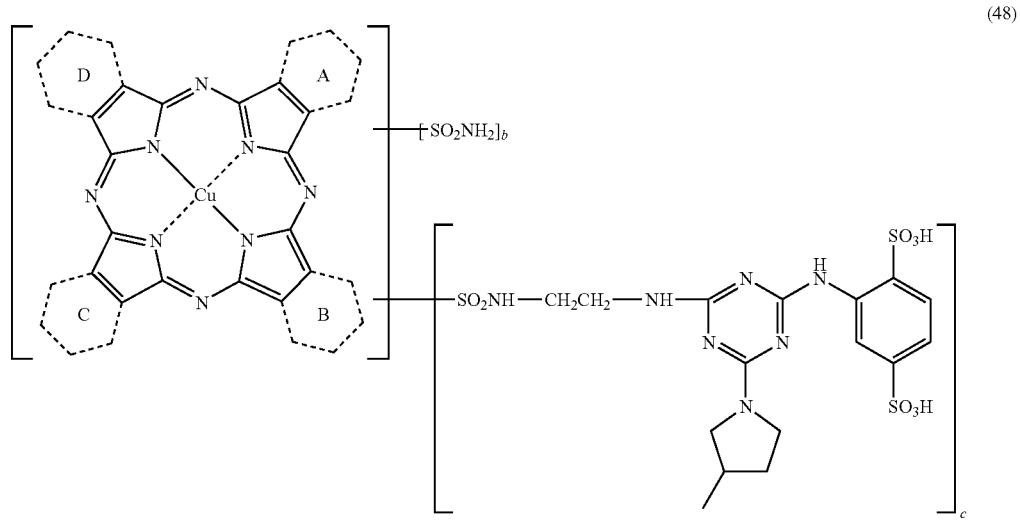

(48)

To 150 parts of ice water, 18.4 parts of cyanuric chloride and 0.2 parts of LEOCOL TD-90 (which is the trade name of a surfactant manufactured by Lion Corporation) were added, and stirred at 10° C. or below for 30 minutes. Next, 31.3 parts of 2,5-disulfoaniline (purity: 90.5%) was added thereto, and reacted at 0 to 25° C. for 4 hours while adjusting the pH of the resulting liquid to 3.0 using a 10% aqueous sodium hydroxide solution. Next, 10.9 parts of 3-methylpyrrolidine was added dropwise to the reaction liquid, and after that, reaction was conducted for 2 hours. The liquid temperature was controlled at 50° C., 60.1 parts of ethylenediamine was added thereto and stirred overnight at room temperature, and then the liquid To 400 parts of ice water, 44.6 parts of a wet cake of a mixture of porphyrazine trisulfonyl chloride and copper dibenzobis(2,3-pyrido)porphyrazine disulfonyl chloride obtained in the same manner as in Example 1-(2) was added, and suspended by stirring at 5° C. or below. Ten minutes later, in said suspension, a solution dissolving 14.2 parts of a compound of the above formula (47) in 2 parts of 28% ammonia water and 100 parts of water was added by pouring while maintaining said liquid temperature at 10° C. or below. In the meantime, 28% ammonia water was continuously added to maintain pH 9.0. With the same pH maintained, the liquid temperature was raised to 20° C. over 1 hour and the liquid was maintained at the same temperature for 8 hours. The liquid volume at this time was 600 parts. The temperature of the reaction liquid was raised to 50° C., 120 parts of sodium chloride (20% to the liquid) was added and stirred for 30 minutes, and then the pH of the liquid was controlled at 1.0 over 20 minutes. The precipitated crystals were separated by filtration and washed with 100 parts of a 20% aqueous sodium chloride solution to obtain 71.0 parts of a wet cake. To the obtained wet cake, 400 parts of water was added, and the pH of the resulting suspension was controlled at 8.1 using a 25% aqueous sodium hydroxide solution, to dissolve the wet cake. The liquid volume at this time was 450 parts. The temperature of the dissolving liquid was raised to 60° C., 90 parts of sodium chloride (20% to the liquid) was added and stirred for 30 minutes, and then the pH of the liquid was controlled at 1.0 over 20 minutes. The precipitated crystals were separated by filtration and washed with 100 parts of a 20% aqueous sodium chloride solution to obtain 79.3 parts of a wet cake. To the obtained wet cake, 634 parts of methanol and 158 parts of water were added, and stirred at 50° C. for 1 hour, followed by filtration to obtain 45.2 parts of a wet cake. The wet cake was dried to obtain 9.8 parts of a compound represented by the above formula (48) of the free acid as blue powder.

λmax: 602.5 nm (in an aqueous solution)

Example 20

(1) Synthesis of Copper tribenzo(2,3-pyrido)porphyrazine (the Above Formula (8): a Mixture in which 1.0 of A, B, C and D is a Pyridine Ring and the rest 3.0 are Benzene Rings in the Following Formula (6))

Formula (6)

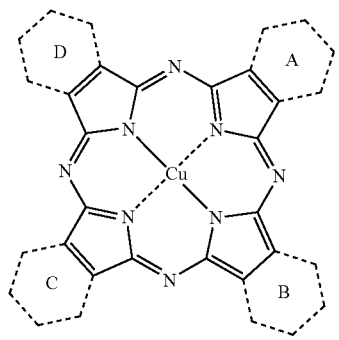

(6)

To a four-neck flask, 250 parts of sulfolane, 12.3 parts of phthalimide, 15.0 parts of quinolinic acid, 72.0 parts of urea, 8.8 parts of copper (II) chloride dihydrate (purity: 97.0%) and 1.0 part of ammonium molybdate were added, the temperature of the resulting mixed liquid was raised to 200° C., and the liquid was maintained at the same temperature for 5 hours. After completion of the reaction, the liquid was cooled to 65° C., 200 parts of methanol was added, and the precipitated crystals were filtered. The obtained crystals were washed with 150 parts of methanol and subsequently with 200 parts of hot water to obtain 72.2 parts of a wet cake. The whole volume of the obtained wet cake was added in 500 parts of 5% hydrochloric acid, the temperature of the mixture was raised to 60° C. and the mixture was maintained at the same temperature for 1 hour. The precipitated crystals were filtered and washed with 200 parts of water. Then, the whole volume of the obtained wet cake was added in 500 parts of 10% ammonia water and maintained at 60° C. for 1 hour, and the precipitated crystals were filtered and then washed sequentially with 300 parts of water and 100 parts of methanol to obtain 33.6 parts of a wet cake. The obtained wet cake was dried at 80° C. to obtain 20.0 parts of copper tribenzo(2,3-pyrido) porphyrazine as blue crystals.

λmax: 655.0 nm (in pyridine)

(2) Synthesis of Copper tribenzo(2,3-pyrido)porphyrazine Trisulfonyl Chloride (a Mixture in which 1.0 of A, B, C and D is a Pyridine Ring and the Rest 3.0 are Benzene Rings, and n is 3.0 in the Following Formula (3))

Formula (3)

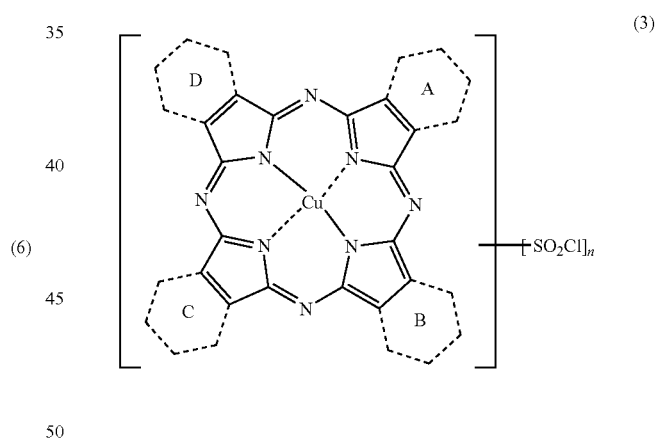

(3)

In 46.2 parts of chlorosulfonic acid, 5.8 parts of copper tribenzo(2,3-pyrido) porphyrazine obtained in the above (1) was gradually added at 60° C. or below while stirring, and reacted at 140° C. for 4 hours. Next, the reaction liquid was cooled to 70° C., and 17.9 parts of thionyl chloride was added dropwise over 30 minutes and reacted at 70° C. for 3 hours. The reaction liquid was cooled to 30° C. or below and slowly poured into 800 parts of ice water, and the precipitated crystals were filtered and washed with 200 parts of cold water to obtain 40.1 parts of a wet cake of copper tribenzo(2,3-pyrido) porphyrazine trisulfonyl chloride.

(3) Synthesis of the Following Formula (16) (a Compound in which 1.0 of A, B, C and D is a Pyridine Ring, the Rest 3.0 are Benzene Rings, E is Ethylene, X is 3-sulfoanilino, and Y is 2-sulfoethylamino in the Above Formula (1))

Formula (16)

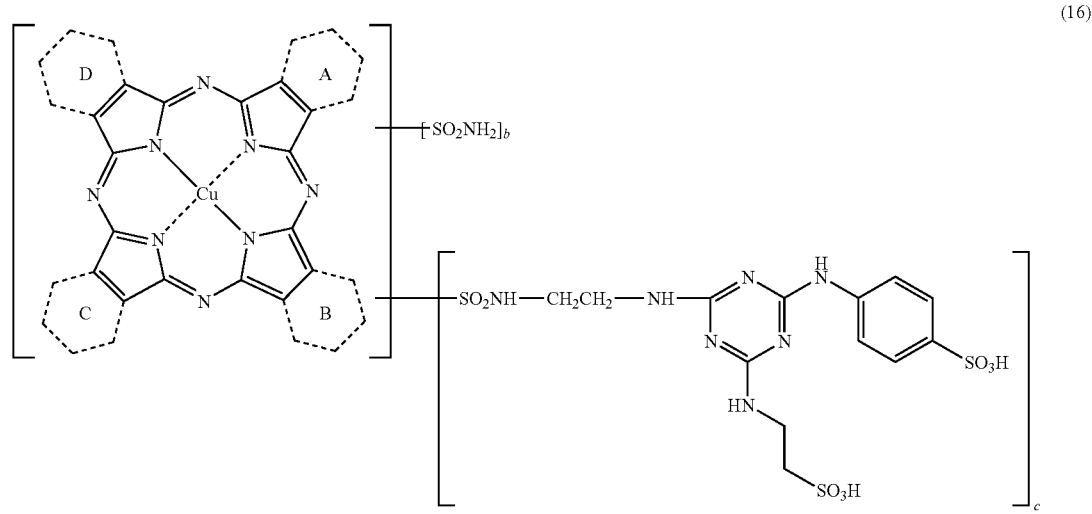

To 50 parts of ice water, 40.1 parts of the wet cake of copper tribenzo(2,3-pyrido)porphyrazine trisulfonyl chloride obtained in the above (2) was added, and suspended by stirring at 5° C. or below. Ten minutes later, in said suspension, a solution dissolving 3.0 parts of a compound of the formula (15) in 2 parts of 28% ammonia water and 60 parts of water was added by pouring while maintaining said liquid temperature at 10° C. or below. In the meantime, 28% ammonia water was continuously added to maintain pH 9.0. With the same pH maintained, the liquid temperature was raised to 20° C. over 1 hour and the liquid was maintained at the same temperature for 8 hours. The liquid volume at this time was 620 parts. The temperature of the reaction liquid was raised to 50° C., 93 parts of sodium chloride (15% to the liquid) was added thereto and stirred for 30 minutes, and then the pH of the liquid was controlled at 2.0 over 20 minutes. The precipitated crystals were separated by filtration and washed with 100 parts of a 10% aqueous sodium chloride solution to obtain 42.1 parts of a wet cake. To the obtained wet cake, 360 parts of water was added, and the pH of the resulting suspension was controlled at 9.0 using a 25% aqueous sodium hydroxide solution, to dissolve said wet cake. The liquid volume at this time was 400 parts. The temperature of the dissolving liquid was raised to 50° C., 60 parts of sodium chloride (15% to the liquid) was added and stirred for 30 minutes, and then the pH of the liquid was controlled at 1.0 over 20 minutes. The precipitated crystals were separated by filtration and washed with 100 parts of a 10% aqueous sodium chloride solution to obtain 41.2 parts of a wet cake. To the obtained wet cake, 255 parts of methanol and 45 parts of water were added, and stirred at 50° C. for 1 hour, followed by filtration to obtain 21.2 parts of a wet cake. The wet cake was dried to obtain 10.1 parts of a compound (a compound in which b is 2.36 and c is 0.64) represented by the above formula (16) of the free acid as blue powder. The copper and inorganic part of this compound was determined, and the average molecular weight was calculated to be 1082.8.

λmax: 602.7 nm (in an aqueous solution)

Example 21

Ink Evaluation (A) Preparation of Ink

The components described in the following table 5 were dissolved by mixing and filtered using a 0.45 μm membrane filter (manufactured by Advantec Co. Ltd) to obtain an ink. In this connection, ion-exchanged water was used as water. In order that the pH of the ink is pH=8 to 10 and the total amount of the ink is 100 parts, water and caustic soda (pH adjuster) were added. The compounds used for evaluation were Example 2, 7, 8, 9, 10, 11 and 13, the ink using the compound of Example 2 is C-2, the ink using the compound of Example 7 is C-7, and also the inks using the compounds of Examples 8 to 11 and 13 are respectively C-8 to C-11 and C-13 corresponding each number.

TABLE 5

| | |
|---|---|
| The compound obtained in the above Example | 3.0 parts |
| Water + caustic soda | 77.9 parts |
| Glycerine | 5.0 parts |
| Urea | 5.0 parts |
| N-methyl-2-pyrrolidone | 4.0 parts |
| IPA (isopropylalcohol) | 3.0 parts |
| Butyl carbitol | 2.0 parts |
| Surfynol 104PG50 (manufactured by Nissin Chemical Industry Co., Ltd.) | 0.1 part |
| Total | 100.0 parts |

As a comparative example, Project Cyan 1 (which is a product name; manufactured by Avecia Corp.: Comparative Example 1) which is a coloring matter for inkjet recording usually used as Direct Blue 199, and a mixture of coloring matter (Comparative Example 2) synthesized and purified by the method described in the example 1 of Patent Literature 8, and a coloring matter compound (Comparative Example 3) synthesized and purified by the method described in the example 3 of Patent Literature 12 were prepared in the same manner as in Examples so that the print density in printing was the same as that of the ink of Examples in Table 5. The ink using the product of Comparative Example 1 is C-A, the ink using the compound of Comparative Example 2 is C-B, and the ink using the product of Comparative Example 3 is C-C.

The structural formulas of the compounds of Comparative Example 2 (101) and Comparative Example 3 (102) are shown below.

Formula (101)

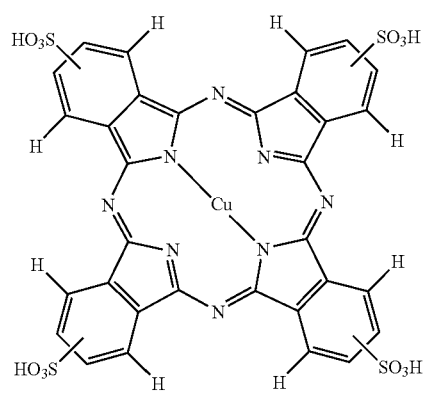

(101)

Formula (102)

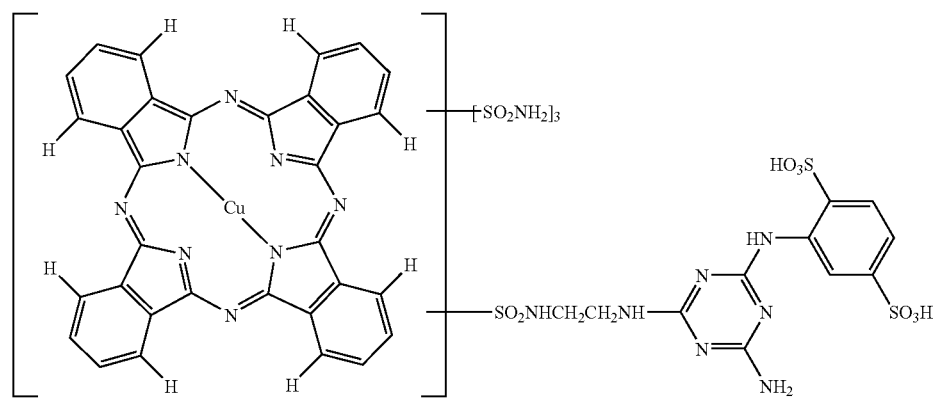

(102)

(B) Inkjet Printing

Using an inkjet printer (trade name: PIXUS ip4100, manufactured by Canon Inc.), inkjet recording was performed on the two kinds of papers, glossy paper A (Advanced Photo Paper (glossy) □7871A, manufactured by Hewlett Packard Japan, Ltd.) and glossy paper B (PMPhoto Paper KA420PSK, manufactured by Seiko-Epson Corporation).

In printing, an image pattern was made so as to obtain 6 gradations of reflection density of 100%, 85%, 70%, 55%, 40% and 25%, and a printed paper with a halftone was obtained. In light fastness test and ozone fastness test, measurement was conducted using the gradation part where the reflection density, D value, of the printed paper before the tests is the nearest to 1.0.

(C) Evaluation of Recorded Image

1. Hue Evaluation

Each hue of the recorded images of the recorded papers was measured using a colorimetric system (SectroEye: manufactured by GretagMacbeth), and $a^*$ and $b^*$ values when $L^*$ of each printed matter was in the range of 40 to 80 were measured. Preferable $a^*$ value is defined as −60 to −20 and preferable $b^*$ value is defined as −60 to −20, and evaluation was conducted on a 3 grade scale.

○: Both $a^*$ and $b^*$ values are within the preferable region.

Δ: Either of $a^*$ or $b^*$ value is within the preferable region.

X: Both $a^*$ and $b^*$ values are out of the preferable region.

2. Light Fastness Test

Using a xenon weatherometer (model Ci4000, manufactured by ATLAS), each test piece of the recorded images was irradiated for 50 hours under the conditions of an illuminance of 0.36 W/m$^2$, a chamber temperature of 24° C. and a humidity of 60% RH. After the test, using a colorimetric system, the reflection densities before and after the test were measured in the range of the reflection density (D value) of 0.70 to 0.85. After the measurement, the residual rate of the coloring matter was calculated according to (reflection density after the test/reflection density before the test)×100(%) and evaluated on a 3 grade scale.

○: Residual rate is 70% or more.

Δ: Residual rate is less than 70 and 50% or more.

X: Residual rate is less than 50%.

3. Ozone Fastness Test

Using an ozone weatherometer (model OMS-H, manufactured by Suga Test Instruments Co., Ltd.), each test piece of the recorded images was left for 8 hours at an ozone concentration of 12 ppm, a chamber temperature of 24° C. and a humidity of 60% RH. After the test, the reflection densities before and after the test were measured in the range of the reflection density (D value) of 0.70 to 0.85 using a colorimetric system. After the measurement, the residual rate of the coloring matter was calculated according to (reflection density after the test/reflection density before the test)×100(%) and evaluated on a 4 grade scale.

⊚: residual rate is 85% or more.

○: Residual rate is less than 85% and 70% or more.

Δ: Residual rate is less than 70% and 50% or more.

X: Residual rate is less than 50%.

4. Moisture Fastness Test

Using a thermo-hygrostat (manufactured by Ohken Co., Ltd), each test piece of the recorded images was left for 3 days at a chamber temperature of 50° C. and a humidity of 90% RH. After the test, the bleeding on each test piece was evaluated on a 3 grade scale, by visual observation.

○: Bleeding is not observed.

Δ: Bleeding is slightly observed.

X: Bleeding is significantly observed.

5. Bronzing Evaluation

Evaluation of bronzing was conducted by visual observation on the gradation where bronzing occurred, among 6 gradations of print density of 100% density, 85% density, 70% density, 55% density, 40% density and 25% density. In regard that bronzing did not occur, OK was described; while in regard that bronzing occurred, the lowest density, of the above 6 gradations, among the print densities where bronzing occurred was described.

The results of hue evaluation, light fastness test, ozone fastness test, moisture fastness test and bronzing resistance evaluation of images recorded with the ink obtained in the above example 8 were shown in the table 6 (glossy paper A) and the table 7 (glossy paper B).

TABLE 6

Evaluation results of the inks: glossy paper A

| Ink number | Hue | Light fastness | Ozone fastness | Moisture fastness | Bronzing resistance |
|---|---|---|---|---|---|
| C-2 | ○ | ○ | ⊚ | ○ | OK |
| C-7 | ○ | ○ | ⊚ | ○ | OK |
| C-8 | ○ | ○ | ⊚ | ○ | OK |
| C-9 | ○ | ○ | ⊚ | ○ | OK |
| C-10 | ○ | ○ | ⊚ | ○ | OK |
| C-11 | ○ | ○ | ⊚ | ○ | OK |
| C-13 | ○ | ○ | ⊚ | ○ | OK |
| C-A | ○ | ○ | X | ○ | OK |
| C-B | ○ | ○ | X | ○ | OK |
| C-C | ○ | ○ | ○ | ○ | OK |

TABLE 7

Evaluation results of the inks: glossy paper B

| Ink number | Hue | Light fastness | Ozone fastness | Moisture fastness | Bronzing resistance |
|---|---|---|---|---|---|
| C-2 | ○ | ○ | ⊚ | ○ | OK |
| C-7 | ○ | ○ | ⊚ | ○ | OK |
| C-8 | ○ | ○ | ⊚ | ○ | OK |
| C-9 | ○ | ○ | ⊚ | ○ | OK |
| C-10 | ○ | ○ | ⊚ | ○ | OK |
| C-11 | ○ | ○ | ⊚ | ○ | OK |
| C-13 | ○ | ○ | ⊚ | ○ | OK |
| C-A | ○ | ○ | X | ○ | OK |
| C-B | ○ | ○ | X | ○ | OK |
| C-C | ○ | ○ | ○ | ○ | OK |

As is clear from Tables 6 and 7, the cyan ink using the compound of the present invention has an excellent hue and is good in light fastness, ozone fastness and moisture fastness, particularly excellent in ozone fastness.

Specifically, even when any of glossy papers A and B was used, Comparative Examples 1 and 2 had a residual rate of coloring matter of less than 50% in the ozone fastness test, showing that it is clearly poor in ozone fastness, and likewise Comparative Example 3 had a residual rate of coloring matter of 70% or more and less than 85%.

However, when C2 to C13 as the inks of the present invention were used, all the residual rates of coloring matter were 85% or more, and it is found that C2 to C13 are more excellent than Comparative Examples C-A to C-C in regard to ozone fastness.

The invention claimed is:

1. A porphyrazine coloring matter represented by the following formula (1) or a salt thereof:

(1)

wherein,
each of the rings A to D independently represents a benzene ring or a 6-membered nitrogen-containing heteroaromatic ring, at least one or more thereof is a benzene ring and at least one of the rest is a nitrogen-containing heteroaromatic ring, E represents alkylene, X is an anilino group or a naphthylamino group, having at least one sulfo, carboxy or phosphono group, as a substituent, said anilino group or said naphthylamino group may be further substituted by one or more kinds of substituents selected from the group consisting of a sulfo group, a carboxy group, a phosphono group, a sulfamoyl group, a carbamoyl group, a hydroxy group, an alkoxy group, an amino group, a mono- or di-alkylamino group, a mono- or di-arylamino group, an acetylamino group, an ureide group, an alkyl group, a nitro group, a cyano group, a halogen atom, an alkylsulfonyl group and an alkylthio group, Y represents an amino group; a hydroxy group; a mono- or di-alkylamino group or a nitrogen-containing heterocyclic group, which may have one or more kinds of substituents selected from the group consisting of a sulfo group, a carboxy group, a phosphono group, a sulfamoyl group, a carbamoyl group, a hydroxy group, an alkoxy group, an amino group, a mono- or di-alkylamino group, a mono- or di-arylamino group, an acetylamino group, an ureide group, an alkyl group, a nitro group, a cyano group, a halogen atom, an alkylsulfonyl group and an alkylthio group; however, excepting for the combination in which Y is an amino group or a hydroxy group and X is a substituted anilino group, b is from 0 to 2.9, c is from 0.1 to 3, and the sum of b and c is from 1 to 3.

2. The porphyrazine coloring matter or a salt thereof according to claim 1, wherein the 6-membered nitrogen-containing heteroaromatic ring represented by the rings A to D is a pyridine ring or a pyrazine ring.

3. The porphyrazine coloring matter or a salt thereof according to claim 1 or 2, which is obtained by reacting a porphyrazine compound represented by the following formula (3) with an organic amine represented by the following formula (4) in the presence of ammonia:

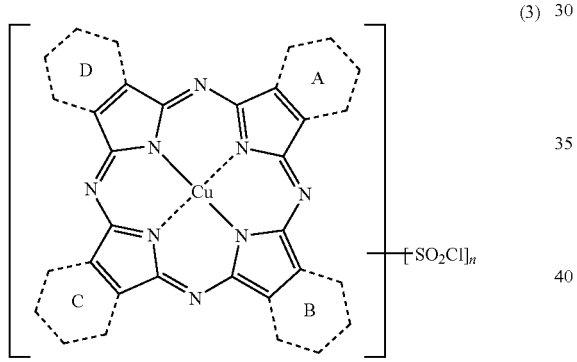

(3)

wherein, the rings A to D have the same meanings as those described in claim 1, and n is from 1 to 3,

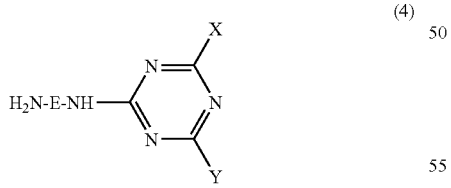

(4)

wherein, E, X and Y have the same meanings as those described in claim 1.

4. The porphyrazine coloring matter or a salt thereof according to claim 2, wherein,
among the rings A to D, 1 to 3 rings is a pyridine ring or a pyrazine ring,
E represents C2 to C4 alkylene,
X is an anilino group or a naphthylamino group, having at least one sulfo or carboxy group, as a substituent; or a phosphono-substituted anilino group,
said substituted anilino and naphthylamino groups may further have 0 to 3 substituents of one or more kinds of substituents selected from the group consisting of a sulfo group, a carboxy group, a phosphono group, a hydroxy group, an alkoxy group, an ureide group, an acetylamino group, a nitro group and a chlorine atom,
Y is an amino group; a hydroxy group; a mono- or di-alkylamino group or a nitrogen-containing heteroaromatic ring group, which may be substituted by a hydroxy group, a sulfo group, a carboxy group or a phosphono group; however, excepting for the combination in which Y is an amino group or a hydroxy group and X is a substituted anilino group,
b is from 0 to 2.9, c is from 0.1 to 3, and the sum of b and c is from 1 to 3.

5. The porphyrazine coloring matter or a salt thereof according to claim 4, wherein,
E represents ethylene or propylene,
X is a sulfo-substituted anilino group; a carboxy-substituted anilino group; or a sulfo-substituted naphthylamino group,
Y is an amino group; a hydroxy group; or a mono- or di-alkylamino group or a nitrogen-containing heteroaromatic ring group, which may be substituted by a hydroxy group, a sulfo group, a carboxy group; however, excepting for the combination in which Y is an amino group or a hydroxy group and X is a substituted anilino group,
b is from 0 to 2.9, c is from 0.1 to 3, and the sum of b and c is from 1 to 3.

6. The porphyrazine coloring matter or a salt thereof according to claim 1, wherein,
the ring A is a pyridine ring fused at the 2-position and the 3-position or at the 3-position and the 4-position, or a pyrazine ring fused at the 2-position and the 3-position,
the ring B is a pyridine ring fused at the 2-position and the 3-position or at the 3-position and the 4-position, or a pyrazine ring fused at the 2-position and the 3-position, or a benzene ring,
the ring C is a pyridine ring fused at the 2-position and the 3-position or at the 3-position and the 4-position, or a pyrazine ring fused at the 2-position and the 3-position, or a benzene ring,
the ring D is a benzene ring,
E is C2 to C4 alkylene,
X is an anilino group or a naphthylamino group, having 1 to 3 substituents selected from the group consisting of a sulfo group, a carboxy group, a methoxy group, a nitro group, a chlorine atom and a hydroxyl group,
Y is an amino group; a hydroxy group; a mono- or di-C1 to C4 alkylamino group or a 5 to 7-membered nitrogen-containing heterocyclic group, which may be substituted by a hydroxy group, a sulfo group or a carboxy group; however, excepting for the combination in which Y is an amino group or a hydroxy group and X is a substituted anilino group,
b is from 0 to 2.9 and c is from 0.1 to 3.

7. The porphyrazine coloring matter or a salt thereof according to claim 1 or 2, which is represented by the following formula (2):

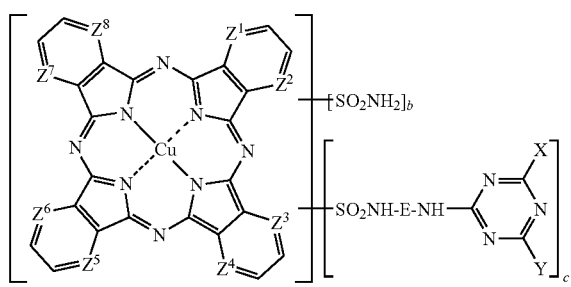

(2)

wherein,
each of $Z^1$ to $Z^8$ independently represents a nitrogen atom or a carbon atom, at least one among the combinations of $Z^1$ and $Z^2$, $Z^3$ and $Z^4$, $Z^5$ and $Z^6$, and $Z^7$ and $Z^8$ is a combination of carbon atoms, and E, X, Y, b and c have the same meanings as those described in claim 1.

8. The porphyrazine coloring matter according to claim 7 or salt thereof, which is obtained by reacting a porphyrazine coloring matter represented by the following formula (5):

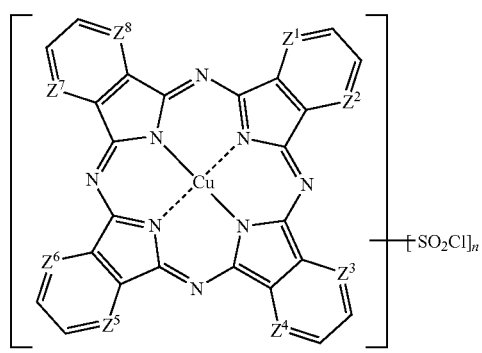

(3)

wherein $Z^1$ to $Z^8$ have the same meanings as those described in claim 7 and n is from 1 to 3,
with an organic amine represented by the formula (4):

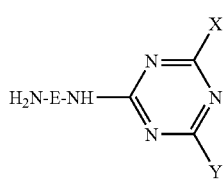

(4)

wherein E, X and Y have the same meanings as described in claim 7
in the presence of ammonia.

9. The porphyrazine coloring matter or a salt thereof according to claim 1, which is a mixture of a porphyrazine coloring matter in which one of the rings A to D is a nitrogen-containing heteroaromatic ring and the other three are benzene rings and a porphyrazine coloring matter in which two of the rings A to D are nitrogen-containing heteroaromatic rings and the other two are benzene rings.

10. The porphyrazine coloring matter or a salt thereof according to claim 9 wherein the nitrogen-containing heteroaromatic ring is a pyridine ring.

11. A mixture of coloring matters containing the porphyrazine coloring matter or a salt thereof according to claim 1 or 2.

12. A mixture of coloring matter of the porphyrazine coloring matter or a salt thereof according to claim 1 or 2 and a phthalocyanine coloring matter.

13. An ink comprising at least one kind of the porphyrazine coloring matter or a salt thereof according to claim 1 as a coloring matter component.

14. The ink according to claim 13, containing an organic solvent together with the porphyrazine coloring matter.

15. The ink according to claim 13 or 14, which is for inkjet recording.

16. An inkjet recording method comprising discharging ink droplets of the ink according to claim 13 responding to a recording signal to carry out recording on a record-receiving material.

17. The inkjet recording method according to claim 16, wherein the record-receiving material is a communication sheet.

18. The inkjet recording method according to claim 17, wherein the communication sheet is a sheet subjected to surface treatment and has an ink image receiving layer containing white inorganic pigment particles on a support thereof.

19. A container containing the ink according to any one of claims 13 to 14.

20. An inkjet printer having the container according to claim 19.

21. A colored product colored with the ink according to claim 13 or 14.

22. The porphyrazine coloring matter or a salt thereof according to claim 1, wherein,
among the rings A to D, 1 to 2 rings is a pyridine ring or a pyrazine ring and the rest are benzene rings, as an average value,
E represents C2 to C4 alkylene, and
(i) X is a mono- or disulfo-substituted anilino group; a dicarboxy-substituted anilino group; or a mono- or disulfo-substituted naphthylamino group, Y is a mono- or di(C1 to C4 alkyl)amino group having a group selected from the group consisting of a hydroxy group, a sulfo group, a carboxy group and a C1 to C4 alkoxy group which may be substituted with a hydroxy group as a substituent; or a 5 to 7-membered nitrogen-containing heterocyclic group which may have a group selected from the group consisting of methyl, ethyl, sulfo, carboxy group and hydroxy group as a substituent, or
(ii) X is a sulfo-substituted naphthylamino group and Y is an amino group.

23. The porphyrazine coloring matter or a salt thereof according to claim 1, wherein Y is 2-sulfoethylamino, 2-carboxyethylamino, carboxymethylamino, 2-hydroxyethylamino, 2-ethoxy-2-ethylamino, 1-hydroxy-butylamino, 5-carboxy-pentylamino, 2-methoxy-ethylamino, 2-ethoxyethylamino, (2-hydroxy)ethoxyethylamino, di(2-hydroxyethyl)amino or di(2-carboxyethyl)amino.

24. The porphyrazine coloring matter or a salt thereof according to claim 1, wherein Y is 2-sulfoethylamino, bis(2-carboxyethyl)amino, 2-hydroxyethylamino, 2-hydroxyethoxyethylamino, morpholinyl, piperidinyl, pyrrolidinyl, 2-carboxypyrrolidinyl, 4-ethylpiperazinyl, 2-ethylpiperidinyl and 3-methylpyrrolidinyl.

25. A container containing the ink according to claim 15.

* * * * *